(12) United States Patent
Ramharter et al.

(10) Patent No.: US 10,919,913 B2
(45) Date of Patent: Feb. 16, 2021

(54) SPIRO[3H-INDOLE-3,2'-PYRROLIDIN]-2(1H)-ONE COMPOUNDS AND DERIVATIVES AS MDM2-P53 INHIBITORS

(71) Applicant: Boehringer Ingelheim International GmbH, Ingelheim am Rhein (DE)

(72) Inventors: Juergen Ramharter, Vienna (AT); Joachim Broeker, Moedling (AT); Annika Gille, Ulm (DE); Andreas Gollner, Vienna (AT); Manuel Henry, Schemmerhofen (DE); Nina Kerres, Vienna (AT); Harald Weinstabl, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/272,482

(22) Filed: Feb. 11, 2019

(65) Prior Publication Data

US 2019/0169209 A1 Jun. 6, 2019

Related U.S. Application Data

(62) Division of application No. 15/503,754, filed as application No. PCT/EP2015/069174 on Aug. 20, 2015, now Pat. No. 10,246,467.

(30) Foreign Application Priority Data

Aug. 21, 2014 (EP) .................................... 14181746

(51) Int. Cl.

| | |
|---|---|
| *A61K 31/553* | (2006.01) |
| *A61P 29/00* | (2006.01) |
| *A61P 31/00* | (2006.01) |
| *A61P 35/00* | (2006.01) |
| *C07D 498/22* | (2006.01) |
| *C07D 498/20* | (2006.01) |
| *C07D 487/20* | (2006.01) |
| *A61K 31/5365* | (2006.01) |
| *C07D 471/20* | (2006.01) |
| *C07D 487/10* | (2006.01) |
| *A61K 31/438* | (2006.01) |
| *A61K 45/06* | (2006.01) |
| *C07D 471/22* | (2006.01) |
| *C08K 3/18* | (2006.01) |

(52) U.S. Cl.
CPC .......... *C07D 498/20* (2013.01); *A61K 31/438* (2013.01); *A61K 31/5365* (2013.01); *A61K 31/553* (2013.01); *A61K 45/06* (2013.01); *C07D 471/20* (2013.01); *C07D 471/22* (2013.01); *C07D 487/10* (2013.01); *C07D 487/20* (2013.01); *C07D 498/22* (2013.01); *C08K 3/18* (2013.01)

(58) Field of Classification Search
CPC ..... A61K 31/553; C07D 498/22; A61P 29/00; A61P 31/00; A61P 35/00
See application file for complete search history.

(56) References Cited

U.S. PATENT DOCUMENTS

| | | | |
|---|---|---|---|
| 8,119,623 B2 | 2/2012 | Burdack et al. | |
| 9,045,414 B2 | 6/2015 | Burdack et al. | |
| 10,138,251 B2 | 11/2018 | Gollner et al. | |
| 10,144,739 B2 | 12/2018 | Gollner et al. | |
| 10,246,467 B2 | 4/2019 | Ramharter et al. | |
| 2010/0075949 A1 | 3/2010 | Burdack et al. | |
| 2011/0319378 A1 | 12/2011 | Bartberger et al. | |
| 2012/0071499 A1 | 3/2012 | Chu et al. | |
| 2012/0122839 A1 | 5/2012 | Burdack et al. | |
| 2015/0291611 A1 | 10/2015 | Gollner et al. | |
| 2016/0000764 A1 | 1/2016 | Weinstabl et al. | |

(Continued)

FOREIGN PATENT DOCUMENTS

| | | |
|---|---|---|
| CN | 102443004 A | 5/2012 |
| CN | 103910746 A | 7/2014 |

(Continued)

OTHER PUBLICATIONS

Abstract in English for CN102443004, May 9, 2012.
Kaur et al., "Synthesis and biological activity of 4-aryl-3-bezoyl-5-phenylspiro [pyrrolidine-2.3'-indolin]-2'-one derivatives as novel potent inhibitors of advanced glycation end product", European Journal of Chemistry, 2014, vol. 79, pp. 282-289.
Abstract in English for NPL: Li, B. et al., "Molecular Docking, QSAR and Molecular Dynamics Simulation on Spiro-oxindoles as MDM2 Inhibitors." Acta Chimica Sinica, 2013, vol. 71, No. 10, p. 1396.

(Continued)

*Primary Examiner* — Brenda L Coleman
(74) *Attorney, Agent, or Firm* — Philip I. Datlow

(57) ABSTRACT

The present invention encompasses compounds of formula (I) wherein the groups $R^1$ to $R^7$, A, V, W, X, Y, n, r and q are defined in claim 1, their use as inhibitors of MDM2-p53 interaction, pharmaceutical compositions which contain compounds of this kind, their use as medicaments, especially as agents for treatment and/or prevention of oncological diseases, and synthetic intermediates.

(I)

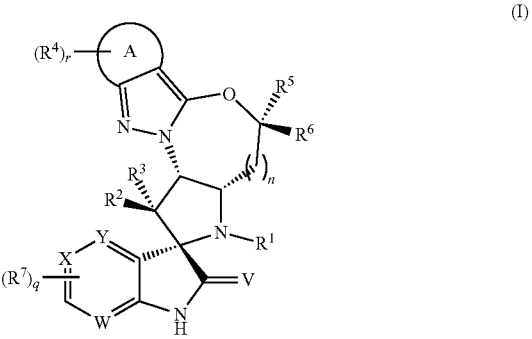

18 Claims, No Drawings

(56) References Cited

U.S. PATENT DOCUMENTS

| | | |
|---|---|---|
| 2016/0052938 A1 | 2/2016 | Ramharter et al. |
| 2017/0174695 A1 | 6/2017 | Gollner et al. |
| 2017/0247394 A1 | 8/2017 | Ramharter et al. |
| 2018/0273541 A1 | 9/2018 | Gollner et al. |
| 2018/0291030 A1 | 10/2018 | Gollner et al. |

FOREIGN PATENT DOCUMENTS

| | | |
|---|---|---|
| JP | 2008531504 A | 8/2008 |
| JP | 2008531542 A | 8/2008 |
| JP | 2012502887 A | 2/2012 |
| JP | 2012162550 A | 8/2012 |
| JP | 2012524745 A | 10/2012 |
| JP | 2013530958 A | 8/2013 |
| WO | 9912904 A1 | 3/1999 |
| WO | 2006090261 A1 | 8/2006 |
| WO | 2006090646 A1 | 8/2006 |
| WO | 2006091646 A3 | 11/2006 |
| WO | 2010028862 A1 | 3/2010 |
| WO | 2010121995 A1 | 10/2010 |
| WO | 2012038307 A1 | 3/2012 |
| WO | 2012116989 A1 | 9/2012 |
| WO | 2015155332 A1 | 10/2015 |
| WO | 2016001376 A1 | 1/2016 |
| WO | 2016027195 A1 | 2/2016 |

OTHER PUBLICATIONS

Cecil Textbook of Medicine, edited by Bennet, J.C., 20th Edition, vol. 1, 1004-1010, 1996.
Chemical Abstracts Service, 2006, Accession No. 897585-13-6.
Chemical Abstracts Service, 2006, Accession No. 897585-15-8.
Chemical Abstracts Service, 2006, Accession No. 897585-17-0.
Chen, G. et al., "Spiro[pyrrolidine-2,3'-oxindole] derivatives synthesized by novel regionselective 1,3-dipolar cycloadditions." Molecular Diversity, 2011, vol. 16, No. 1, pp. 151-156.
Dandia, Reaction of Indole-2,3-Diones with 3-aminopropanol, Organic Preparations and Procedures, International, the New Journal for Organic Synthesis, 2003, vol. 35, No. 4, p. 433-438.
Dermer, Another Anniversary for the war on Cancer, Bio/Technology, 1994, vol. 12, p. 320-328.
Ding et al., Structure-Based Design of Spiro-oxindoles as Potent, Specific Small-Molecule Inhibitors of the MDM2-p53 Interaction, J. Med. Chem, 2006, 49, pp. 3432-3435.
European Search Report for EP 14175620.5 dated Aug. 8, 2014.
Freshney, Culture of Animal Cells, A Manual of Basic Technique, Liss, Inc., 1983, p. 4.
Golub, Molecular Classification of Cancer: Class Discovery and Class Prediction by Gene Expression Monitoring, Science, vol. 286, 1999, p. 531-537.
International Search Report and Written Opinion for PCT/EP2015/069174 dated Sep. 22, 2015.
Kojima, Pharmacological activation of wild-type p53 in the therapy of leukemia, Exp. Hematol. 2016, p. 791-798.
Li, B. et al., "Molecular Docking, QSAR and Molecular Dynamics Simulation on Spiro-oxindoles as MDM2 Inhibitors." Acta Chimica Sinica, 2013, vol. 71, No. 10, pp. 1396-1403.
Marx, M. et al., "Synthetic Design for Combinatorial Chemistry. Solution and Polymer-Supported Synthesis of Polycyclic Lactams by Intramolecular Cyclization of Azomethine Ylides." Journal of the American Chemical Society, 1997, vol. 119, No. 26, pp. 6153-6167.
Tisato, MDM2/X inhibitors under clinical evaluation: perpspectives for the mamagement of hematological malignancies and pediatric cancer, Journal of Hematology and Oncology, 2017, vol. 10, p. 1-17.
U.S. Appl. No. 15/287,958, filed Oct. 7, 2016, Andreas Gollner.
U.S. Appl. No. 12/560,051, filed Sep. 15, 2009, Christoph Burdack.
U.S. Appl. No. 13/351,914, filed Jan. 17, 2012, Christoph Burdack.
U.S. Appl. No. 14/683,173, filed Apr. 10, 2015, Andreas Gollner.
U.S. Appl. No. 14/790,032, filed Jul. 2, 2015, Harald Weinstabl.
U.S. Appl. No. 14/831,241, filed Aug. 20, 2015, Juergen Ramharter.
U.S. Appl. No. 15/503,754, filed Feb. 14, 2017, Juergen Ramharter.
U.S. Appl. No. 61/096,964, filed Sep. 15, 2008, Christoph Burdack.
U.S. Appl. No. 16/003,232, filed Jun. 8, 2018. Inventor: Andreas Gollner.
U.S. Appl. No. 16/005,316, filed Jun. 11, 2018. Inventor: Andreas Gollner.
Waite, Reductive Amination of Substituted Indole-2,3-diones, J. Chem. Soc, 1970. p. 550-552.
Zak, Krzysztof et al. Mdm2 and MdmX inhibitors for the treatment of cancer: a patent review (2011-present), (2013) Expert Opinion on Therapeutic Patents, 23:4, 425-448.

SPIRO[3H-INDOLE-3,2'-PYRROLIDIN]-2(1H)-ONE COMPOUNDS AND DERIVATIVES AS MDM2-P53 INHIBITORS

The present invention relates to new spiro[3H-indole-3,2'-pyrrolidin]-2(1H)-one compounds and derivatives of formula (I)

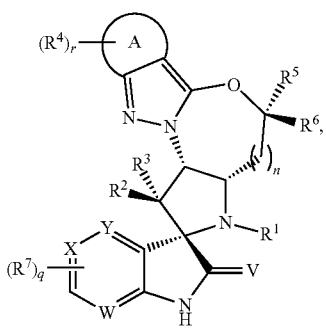

wherein the groups $R^1$ to $R^7$, A, V, W, X, Y, n, r and q have the meanings given in the claims and specification, their use as inhibitors of MDM2-p53 interaction, pharmaceutical compositions which contain compounds of this kind, their use as medicaments, especially as agents for treatment and/or prevention of oncological diseases and synthetic intermediates.

BACKGROUND OF THE INVENTION

The tumor suppressor protein p53 is a sequence specific transcription factor and plays a central role in the regulation of several cellular processes, including cell cycle and growth arrest, apoptosis, DNA repair, senescence, angiogenesis, and innate immunity. The Mouse Double Minute 2 (MDM2) protein (or its human homolog also known as HDM2) acts to down-regulate p53 activity in an auto-regulatory manner, and under normal cellular conditions (absence of stress), the MDM2 protein serves to maintain p53 activity at low levels. MDM2 directly inhibits the transactivation function of p53, exports p53 out of the nucleus, and promotes proteasome-mediated degradation of p53 through its E3 ubiquitin ligase activity.

Deregulation of the MDM2/p53 balance by overexpression of MDM2 or by p53 mutation or loss leads to malignant transformation of normal cells. Presently p53 is known to play a key role in practically all types of human cancers, and the mutation or loss of the p53 gene can be identified in more than 50% of all human cancers worldwide. Analysis of 28 different types of human cancers in nearly 4,000 human tumor samples showed that MDM2 is amplified in 7% of human cancers and that MDM2 overexpression by amplification and p53 mutations are largely mutually exclusive (Momand et al., Nucleic Acid Res (1998) 26:3453-3459).

Because of the powerful tumor suppressor function of p53, reactivation of p53 has been long sought as a potentially novel cancer therapeutic strategy. In tumor harboring wild-type p53, MDM2 is the primary cellular inhibitor of p53 activity, and overexpression of MDM2 was found in many human tumors. Since MDM2 inhibits p53 through a direct protein-protein interaction, blocking this interaction using small molecules was pursued in several academic and industrial pharmaceutical laboratories in the last decade. A variety of non-peptide, drug-like small molecule as e.g. imidazole compounds (e.g. Nutlins or RG7112), benzodiazepinedione compounds, spirooxindole compounds (e.g. MI-219), substituted piperidines, pyrrolidinone compounds (e.g. PXN820-dl) and modifications thereof have been selected and designed in order to block MDM2/p53 interaction as a means to reactivate p53 in cells (Vassilev et al., Science (2004) 303:844-848; Grasberger et al., J Med Chem (2005) 48:909-912; Parks et al., Bioorg Med Chem Lett (2005) 15:765; Ding et al., J Am Soc (2005) 127:10130-10131; WO 2010/028862, U.S. Pat. No. 7,884,107, WO 2008/119741). A number of potent MDM2/p53 inhibitors have been evaluated in animal models of human cancer for their anti-tumor activity (Vassilev et al., Science (2004) 303:844-848; Tovar et al, Cancer Res (2013) 73 (8): 2587-2597; Ding et al, Journal of Medicinal Chemistry (2013) 56 (14): 5979-5983; Rew et al, Journal of Medicinal Chemistry (2012) 55: 4936-4954; Sun et al, Journal of Medicinal Chemistry (2014) 57 (4): 1454-1472).

In the pediatric preclinical testing program (PPTP) of the NCI, early evidence for high level anti-proliferative activity of RG7112, an inhibitor of the MDM2-p53 interaction, could be observed in vitro and in vivo. In particular, RG-7112 showed cytotoxic activity with lower median $IC_{50}$ values for p53 wild-type vs. p53 mutant cell lines (Carol et al., Pediatric Blood and Cancer (2013) 60(4):633-641). Moreover, RG-7112 induced tumor growth inhibition in solid tumor xenograft models and was particularly efficacious in in acute lymphoblastic leukemia (ALL) xenograft models with mixed-lineage leukemia (MLL) rearrangement, (Carol et al., Pediatric Blood and Cancer (2013) 60(4):633-641). Additionally, the antiproliferative and proapoptotic activity of RG7112 has been observed in human acute myeloid leukemia (AML) and human prostate tumor xenograft models harboring p53 wild-type (Tovar et al, Cancer Res (2013) 73 (8): 2587-2597).

Accordingly, small molecule inhibitors of the MDM2 protein interactions offer an important approach towards cancer therapy, either as a single agent, or in combination with a broad variety of anti-tumor therapies and thus, there is the need for further MDM2 inhibitors which can be useful in the treatment of cancer.

The following prior art documents disclose spiro oxindole compounds as inhibitors of MDM2-p53 interaction:
WO 2007/104664; WO 2007/104714; WO 2008/141917; WO 2008/141975; WO 2009/077357; WO 2009/080488; WO 2010/084097; WO 2010/121995; WO 2011/067185; WO 2011/101297; WO 2011/134925; WO 2012/038307; WO 2012/022707; WO 2012/116989; WO 2006/091646; WO 2008/036168; WO 2011/060049; WO 2012/065022; WO 2012/155066; WO 2010/028862; WO 2011/153509 and WO 2012/121361.

The aim of the present invention is to provide new compounds which can be used for the prevention and/or treatment of a disease and/or condition characterised by excessive or abnormal cell proliferation, especially a disease and/or condition wherein the inhibition of the interaction between MDM2 and p53 is of therapeutic benefit.

The compounds according to the invention are characterised by a powerful inhibitory effect on the interaction between MDM2 and p53 and in turn a high efficacy against tumour cells, e.g. osteosarcoma, ALL etc., which is mediated through the inhibition of the interaction between MDM2 and p53. In addition to the inhibitory effect and cellular potency the compounds show good PK properties and selectivity against p53 mutant cell lines.

Furthermore, they have good metabolic stability and, in contrast to many compounds known in the prior art, good chemical stability, i.e. they are for example less prone to epimerisation, a problem identified for many known representatives of spiro oxindoles in the prior art (see e.g. Zhao et al. *J. Am. Chem. Soc* 2013, 135, 7223-7234; Shu et al. Org. Process Res. Dev. 2013, 17, 247-256; WO 2012/065022).

DETAILED DESCRIPTION OF THE INVENTION

It has now been found that, surprisingly, compounds of formula (I) wherein the groups $R^1$ to $R^7$, A, V, W, X, Y, n, r and q have the meanings given hereinafter act as inhibitors of the interaction of specific proteins which are involved in controlling cell proliferation. Thus, the compounds according to the invention may be used for example for the treatment of diseases connected with this protein-protein interaction and characterised by excessive or abnormal cell proliferation.

The present invention therefore relates to a compound of formula (I)

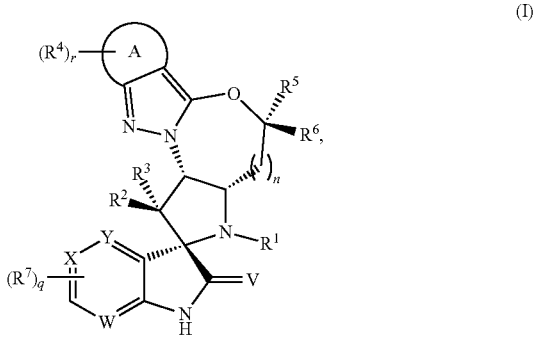

wherein

[A0]

$R^1$ is a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b1}$ is independently selected from among —$OR^{c1}$, —$NR^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2NR^{c1}R^{c1}$, —NHC(O)$R^{c1}$ and —N(C$_{1-4}$alkyl)C(O)$R^{c1}$;

each $R^{c1}$ independently of one another denotes hydrogen or a group, optionally substituted by one or more, identical or different $R^{d1}$ and/or $R^{e1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d1}$ is independently selected from among —$OR^{e1}$, —$NR^{e1}R^{e1}$, halogen, —CN, —C(O)$R^{e1}$, —C(O)O$R^{e1}$, —C(O)N$R^{e1}R^{e1}$, —S(O)$_2R^{e1}$, —S(O)$_2NR^{e1}R^{e1}$, —NHC(O)$R^{e1}$ and —N(C$_{1-4}$alkyl)C(O)$R^{e1}$;

each $R^{e1}$ independently of one another denotes hydrogen or a group, optionally substituted by one or more, identical or different $R^{f1}$ and/or $R^{g1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{f1}$ is independently selected from among —$OR^{g1}$, —$NR^{g1}R^{g1}$, halogen, —CN, —C(O)$R^{g1}$, —C(O)O$R^{g1}$, —C(O)N$R^{g1}R^{g1}$, —S(O)$_2R^{g1}$, —S(O)$_2NR^{g1}R^{g1}$, —NHC(O)$R^{g1}$ and —N(C$_{1-4}$alkyl)C(O)$R^{g1}$;

each $R^{g1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

[B0]

$R^2$ and $R^3$, each independently, is selected from among hydrogen, $C_{6-10}$aryl, 5-10 membered heteroaryl and 3-10 membered heterocyclyl, wherein this $C_{6-10}$aryl, 5-10 membered heteroaryl and 3-10 membered heterocyclyl is optionally substituted by one or more, identical or different $R^{b2}$ and/or $R^{c2}$;

each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2NR^{c2}R^{c2}$, —NHC(O)$R^{c2}$ and —N(C$_{1-4}$alkyl)C(O)$R^{c2}$;

each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2NR^{e2}R^{e2}$, —NHC(O)$R^{e2}$ and —N(C$_{1-4}$alkyl)C(O)$R^{e2}$;

each $R^{e2}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

[C0]

A is selected from among phenyl and 5-6 membered heteroaryl;

each $R^4$ is independently selected from among $R^{a4}$ and $R^{b4}$;

each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b4}$ is independently selected from among —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}OR^{c4}$, —S(O)$_2R^{c4}$, —S(O)$_2NR^{c4}R^{c4}$, —NHSO$_2R^{c4}$, —N(C$_{1-4}$alkyl)SO$_2R^{c4}$, —NHC(O)$R^{c4}$ and —N(C$_{1-4}$alkyl)C(O)$R^4$;

each $R^{c4}$ independently of one another denotes hydrogen or a group, optionally substituted by one or more, identical or different $R^{d4}$ and/or $R^{e4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d4}$ is independently selected from among —$OR^{e4}$, —$NR^{e4}R^{e4}$, halogen, —CN, —C(O)$R^{e4}$, —C(O)O$R^{e4}$, —C(O)N$R^{e4}R^{e4}$, —C(O)N$R^{g4}OR^{e4}$, —S(O)$_2R^{e4}$, —S(O)$_2NR^{e4}R^{e4}$, —NHC(O)$R^{e4}$ and —N(C$_{1-4}$alkyl)C(O)$R^{e4}$;

each $R^{e4}$ independently of one another denotes hydrogen or a group, optionally substituted by one or more, identical or different $R^{f4}$ and/or $R^{g4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{f4}$ is independently selected from among —$OR^{g4}$, —$NR^{g4}R^{g4}$, halogen, —CN, —C(O)$R^{g4}$, —C(O)O$R^{g4}$, —C(O)N$R^{g4}R^{g4}$, —C(O)N$R^{g4}$O$R^{g4}$, —S(O)$_2R^{g4}$, —S(O)$_2$N$R^{g4}R^{g4}$, —NHC(O)$R^{g4}$ and —N(C$_{1-4}$alkyl)C(O)$R^{g4}$;

each $R^{g4}$ is independently selected from among hydrogen, C$_{1-6}$alkyl, C$_{2-6}$alkenyl, C$_{2-6}$alkynyl, C$_{1-6}$haloalkyl, C$_{3-7}$cycloalkyl, C$_{4-7}$cycloalkenyl, C$_{6-10}$aryl, 5-10 membered heteroaryl and 3-10 membered heterocyclyl;

r denotes the number 0, 1, 2 or 3

[D0]

$R^5$ and $R^6$, each independently, is selected from among hydrogen, C$_{1-4}$alkyl and C$_{1-4}$haloalkyl;

n denotes the number 0 or 1;

[E0]

each $R^7$ is independently selected from among halogen, C$_{1-4}$alkyl, —CN, C$_{1-4}$haloalkyl, —OC$_{1-4}$alkyl and —OC$_{1-4}$haloalkyl;

q denotes the number 0, 1, 2 or 3;

[F0]

W, X and Y is each independently selected from —N= and —CH= with the proviso that the hydrogen in each —CH= may be replaced by a substituent $R^7$ if present and that a maximum of two of W, X and Y can be —N=;

[G0]

V is oxygen or sulfur;

or a salt thereof.

In one aspect the invention relates to the compound of formula (Ia)

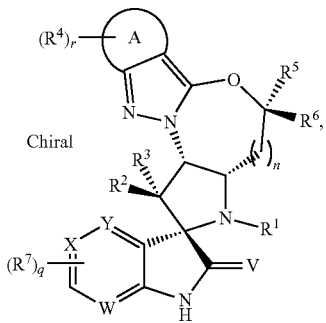

(Ia)

or a salt thereof, wherein the groups $R^1$ to $R^7$, A, V, W, X, Y, n, q and r are defined as for formula (I).

In another aspect the invention relates to the compound of formula (Ib)

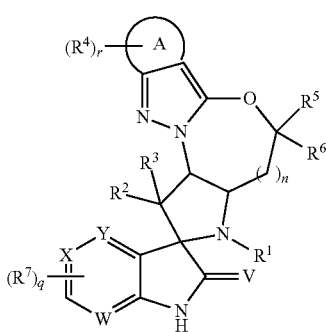

(Ib)

or a salt thereof, wherein the groups $R^1$ to $R^7$, A, V, W, X, Y, n, q and r are defined as for formula (I).

It is to be understood that compounds (Ia) are a subset of compounds (I) and that whenever the term "compound(s) (I)" is used this also includes compound(s) (Ia) unless stated otherwise.

It is to be understood that compounds (I) and compounds (Ia) are a subset of compounds (Ib) and that whenever the term "compound(s) (Ib)" is used this also includes compound(s) (I) and compound(s) (Ia) unless stated otherwise.

In another aspect [A1] the invention relates to a compound of formula (I) or (Ia) or (Ib), wherein $R^1$ is a group, optionally substituted by one or more, identical or different $R^{b1}$ and/or $R^{c1}$, selected from among C$_{1-6}$alkyl, C$_{2-6}$alkenyl, C$_{1-6}$haloalkyl and C$_{3-7}$cycloalkyl;

each $R^{b1}$ is independently selected from among —O$R^{c1}$, —N$R^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2$N$R^{c1}R^{c1}$, —NHC(O)$R^{c1}$ and —N(C$_{1-4}$alkyl)C(O)$R^{c1}$;

each $R^{c1}$ independently of one another denotes hydrogen or a group, optionally substituted by one or more, identical or different $R^{d1}$ and/or $R^{e1}$, selected from among C$_{1-6}$alkyl, C$_{3-7}$cycloalkyl, C$_{6-10}$aryl, 5-10 membered heteroaryl and 3-10 membered heterocyclyl;

each $R^{d1}$ is independently selected from among —O$R^{e1}$, —N$R^{e1}R^{e1}$, halogen, —CN, —C(O)$R^{e1}$, —C(O)O$R^{e1}$, —C(O)N$R^{e1}R^{e1}$, —S(O)$_2R^{e1}$, —S(O)$_2$N$R^{e1}R^{e1}$, —NHC(O)$R^{e1}$ and —N(C$_{1-4}$alkyl)C(O)$R^{e1}$;

each $R^{e1}$ independently of one another is selected from among hydrogen, C$_{1-6}$alkyl, C$_{3-7}$cycloalkyl, C$_{6-10}$aryl, 5-10 membered heteroaryl and 3-10 membered heterocyclyl;

or a salt thereof.

In another aspect [A2] the invention relates to a compound of formula (I) or (Ia) or (Ib), wherein $R^1$ is a group, optionally substituted by one or more, identical or different $R^{c1}$, selected from among C$_{1-6}$alkyl, C$_{2-6}$alkenyl and C$_{3-7}$cycloalkyl;

each $R^{c1}$ independently of one another is a group, optionally substituted by one or more, identical or different $R^{d1}$ and/or $R^{e1}$, selected from among C$_{1-6}$alkyl, C$_{3-7}$cycloalkyl, C$_{6-10}$aryl and 3-10 membered heterocyclyl;

each $R^{d1}$ is independently selected from among —O$R^{e1}$ and halogen;

each $R^{e1}$ independently of one another is C$_{1-6}$alkyl;

or a salt thereof.

In another aspect [A3] the invention relates to a compound of formula (I) or (Ia) or (Ib), wherein $R^1$ is a group, optionally substituted by one or more, identical or different $R^{c1}$, selected from among C$_{1-6}$alkyl, C$_{2-6}$alkenyl and C$_{3-7}$cycloalkyl;

each $R^{c1}$ independently of one another is a group, optionally substituted by one or more, identical or different $R^{d1}$ and/or $R^{e1}$, selected from among C$_{1-6}$alkyl, C$_{3-7}$cycloalkyl, phenyl and 5-6 membered heterocyclyl;

each $R^{d1}$ is independently selected from among —O$R^{e1}$ and halogen;

each $R^{e1}$ independently of one another is C$_{1-6}$alkyl;

or a salt thereof.

In another aspect [A4] the invention relates to a compound of formula (I) or (Ia) or (Ib), wherein $R^1$ is selected from among C$_{1-6}$alkyl, C$_{3-7}$cycloalkyl, C$_{3-7}$cycloalkyl-C$_{1-6}$alkyl and C$_{2-6}$alkenyl;

or a salt thereof.

In another aspect [A5] the invention relates to a compound of formula (I) or (Ia) or (Ib), wherein $R^1$ is C$_{3-7}$cycloalkyl-C$_{1-6}$alkyl;

or a salt thereof.

In another aspect [A6] the invention relates to a compound of formula (I) or (Ia) or (Ib), wherein
$R^1$ is cyclopropylmethyl;
or a salt thereof.

In another aspect [B1] the invention relates to a compound of formula (I) or (Ia) or (Ib), wherein
one of $R^2$ and $R^3$ is hydrogen and the other is selected from among phenyl and 5-6 membered heteroaryl, wherein this phenyl and 5-6 membered heteroaryl is optionally substituted by one or more, identical or different $R^{b2}$ and/or $R^{c2}$;
  each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2NR^{c2}R^{c2}$, —NHC(O)$R^{c2}$ and —N(C$_{1-4}$alkyl)C(O)$R^{c2}$;
  each $R^{c2}$ independently of one another denotes hydrogen or a group selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;
or a salt thereof.

In another aspect [B2] the invention relates to a compound of formula (I) or (Ia) or (Ib), wherein
one of $R^2$ and $R^3$ is hydrogen and the other is selected from among phenyl and pyridyl, wherein this phenyl and pyridyl is optionally substituted by one or more, identical or different substituents selected from among —OC$_{1-6}$alkyl, halogen, C$_{1-6}$alkyl and C$_{1-6}$haloalkyl;
or a salt thereof.

In another aspect [B3] the invention relates to a compound of formula (I) or (Ia) or (Ib), wherein
one of $R^2$ and $R^3$ is hydrogen and the other is selected from among 3-chloro phenyl, 3-chloro-2-fluoro phenyl and 3-bromo 2-fluoro phenyl;
or a salt thereof.

In further aspects [B4], [B5], [B6] and [B7] the invention relates to a compound of formula (I) or (Ia) or (Ib) with structural aspects [B0], [B1], [B2] and [B3], wherein
$R^3$ is hydrogen;
or a salt thereof.

In further aspects [B8], [B9], [B10] and [B11] the invention relates to a compound of formula (I) or (Ia) or (Ib) with structural aspects [B0], [B1], [B2] and [B3], wherein
$R^2$ is hydrogen;
or a salt thereof.

In another aspect [C1] the invention relates to a compound of formula (I) or (Ia) or (Ib), wherein
A is selected from among phenyl and 5-6 membered heteroaryl;
each $R^4$ is independently selected from among $R^{a4}$ and $R^{b4}$;
  each $R^{a4}$ independently of one another is a group, optionally substituted by one or more, identical or different $R^{b4}$ and/or $R^{c4}$, selected from among C$_{1-6}$alkyl, C$_{2-6}$alkenyl, C$_{2-6}$alkynyl, C$_{1-6}$haloalkyl, C$_{3-7}$cycloalkyl, C$_{4-7}$cycloalkenyl, C$_{6-10}$aryl, 5-10 membered heteroaryl and 3-10 membered heterocyclyl;
  each $R^{b4}$ is independently selected from among —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}OR^{c4}$, —S(O)$_2R^{c4}$, —S(O)$_2NR^{c4}R^{c4}$, —NHSO$_2R^{c4}$, —N(C$_{1-4}$alkyl)SO$_2R^{c4}$, —NHC(O)$R^{c4}$ and —N(C$_{1-4}$alkyl)C(O)$R^{c4}$;
  each $R^{c4}$ independently of one another is selected from among hydrogen, C$_{1-6}$alkyl, C$_{2-6}$alkenyl, C$_{2-6}$alkynyl, C$_{1-6}$haloalkyl, C$_{3-7}$cycloalkyl, C$_{4-7}$cycloalkenyl, C$_{6-10}$aryl, 5-10 membered heteroaryl and 3-10 membered heterocyclyl;
r denotes the number 0, 1, 2 or 3;
or a salt thereof.

In another aspect [C2] the invention relates to a compound of formula (I) or (Ia) or (Ib), wherein
A is selected from among phenyl and pyridyl;
each $R^4$ is independently selected from among $R^{a4}$ and $R^{b4}$;
  each $R^{a4}$ independently of one another is C$_{1-6}$alkyl optionally substituted by one or more, identical or different $R^{b4}$;
  each $R^{b4}$ is independently selected from among —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}OR^{c4}$, —S(O)$_2R^{c4}$, —S(O)$_2NR^{c4}R^{c4}$, —NHSO$_2R^{c4}$, —N(C$_{1-4}$alkyl)SO$_2R^{c4}$, —NHC(O)$R^{c4}$ and —N(C$_{1-4}$alkyl)C(O)$R^{c4}$;
  each $R^{c4}$ independently of one another is selected from among hydrogen and C$_{1-6}$alkyl;
r denotes the number 0, 1, 2 or 3;
or a salt thereof.

In another aspect [C3] the invention relates to a compound of formula (I) or (Ia) or (Ib), wherein
A is selected from among phenyl and pyridyl;
each $R^4$ is independently selected from among $R^{a4}$ and $R^{b4}$;
  each $R^{a4}$ independently of one another is C$_{1-6}$alkyl optionally substituted by one or more, identical or different $R^{b4}$;
  each $R^{b4}$ is independently selected from among —$OR^{c4}$, halogen, —CN, —C(O)O$R^{c4}$, —C(O)N$R^{c4}R^{c4}$ and —S(O)$_2R^{c4}$;
  each $R^{c4}$ independently of one another is selected from among hydrogen and C$_{1-6}$alkyl;
r denotes the number 0, 1, 2 or 3;
or a salt thereof.

In further aspects [C4], [C5], [C6] and [C7] the invention relates to a compound of formula (I) or (Ia) or (Ib) with structural aspects [C0], [C1], [C2] and [C3], wherein
r denotes the number 1 or 2;
or a salt thereof.

In another aspect [C8] the invention relates to a compound of formula (I) or (Ia) or (Ib), wherein
A together with the r substituents $R^4$ is

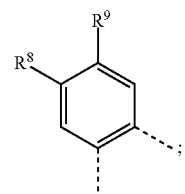

$R^8$ is selected from among hydrogen, C$_{1-6}$alkyl, —OC$_{1-6}$alkyl, halogen, —CN, —C(O)OH, —C(O)OC$_{1-6}$alkyl, —C(O)NH$_2$, —C(O)NHC$_{1-6}$alkyl, —C(O)N(C$_{1-6}$alkyl)$_2$ and —S(O)$_2$C$_{1-6}$alkyl;

$R^9$ is selected from among hydrogen, C$_{1-6}$alkyl, —OC$_{1-6}$alkyl, halogen, —CN, —C(O)OH, —C(O)OC$_{1-6}$alkyl, —C(O)NH$_2$, —C(O)NHC$_{1-6}$alkyl, —C(O)N(C$_{1-6}$alkyl)$_2$ and —S(O)$_2$C$_{1-6}$alkyl;

with the proviso that $R^8$ and $R^9$ are not both hydrogen;
or a salt thereof.

In another aspect [C9] the invention relates to a compound of formula (I) or (Ia) or (Ib), wherein
A together with the r substituents R⁴ is

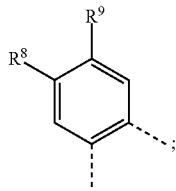

one of $R^8$ and $R^9$ is —C(O)OH and the other is hydrogen;
or a salt thereof.

In another aspect [D1] the invention relates to a compound of formula (I) or (Ia) or (Ib), wherein
$R^5$ and $R^6$ is hydrogen;
n denotes the number 0 or 1;
or a salt thereof.

In another aspect [D2] the invention relates to a compound of formula (I) or (Ia) or (Ib), wherein
$R^5$ and $R^6$ is hydrogen;
n is 0;
or a salt thereof.

In another aspect [D3] the invention relates to a compound of formula (I) or (Ia) or (Ib), wherein
$R^5$ and $R^6$ is hydrogen;
n is 1;
or a salt thereof.

In another aspect [E1] the invention relates to a compound of formula (I) or (Ia) or (Ib), wherein
each $R^7$ independently is halogen and q is 1 or 2;
or a salt thereof.

In another aspect [E2] the invention relates to a compound of formula (I) or (Ia) or (Ib), wherein
each $R^7$ independently is chlorine or fluorine and q is 1 or 2;
or a salt thereof.

In another aspect [F1] the invention relates to a compound of formula (I) or (Ia) or (Ib), wherein
W, X and Y are —CH= with the proviso that the hydrogen in each —CH= may be replaced by a substituent $R^7$ if present;
or a salt thereof.

In another aspect [EF1] the invention relates to a compound of formula (I) or (Ia) or (Ib), wherein
the 6-membered ring comprising W, X and Y together with the q substituents $R^7$ has a substructure selected from among (i) and (ii)

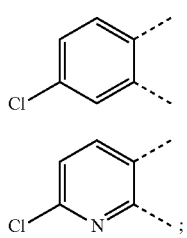

or a salt thereof.

In another aspect [G1] the invention relates to a compound of formula (I) or (Ia) or (Ib), wherein
V is oxygen;
or a salt thereof.

All the above-mentioned structural aspects A1 to A6, B1 to B11, C1 to C9, D1 to D3, E1 and E2, F1, G1 and EF1 are preferred embodiments of the corresponding aspects A0, B0, C0, D0, E0, F0, EF0 and G0, respectively, wherein EF0 (EF) represents the combination of E0 (E) and F0 (F). The structural aspects A0 to A6, B0 to B11, C0 to C9, D0 to D3, E0 to E2, F0 and F1, EF0 and EF1, and G0 and G1 relating to different molecular parts of the compounds (I), (Ia) and (Ib) according to the invention may be permutated with one another as desired in combinations ABCDEFG, so as to obtain preferred compounds (I), (Ia) and (Ib) (aspects E and F can be replaced by combination aspect EF). Each combination ABCDEFG represents and defines individual embodiments or generic subsets of compounds according to the invention.

Preferred embodiments of the invention are example compounds I-1 to I-117.

All synthetic intermediates disclosed herein are also part of the invention.

In a further aspect the invention also relates to synthetic intermediates of formula A-4 and their salts, which can be used as key intermediates in the synthesis of compounds of formula (I) or (Ia) or (Ib):

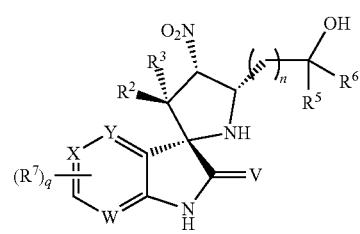

The definitions of groups $R^2$, $R^3$, $R^5$, $R^6$, $R^7$, V, W, X, Y, n and q in A-4 correspond to those as given for compound (I), (Ia) and (Ib) above, i.e. [B0] for $R^2/R^3$, [D0] for $R^5/R^6$/n, [E0] for $R^7$/q, [F0] for W/X/Y and [G0] for V.

Preferred intermediates A-4 are those which lead to preferred compounds (I) or (Ia) or (Ib) according to the invention, i.e. preferred embodiments of A-4 have structural aspects selected from [B0] to [B11] for $R^2/R^3$, [D0] to [D3] for $R^5/R^6$/n, [E0] to [E2] for $R^7$/q, [F0] and [F1] for W/X/Y, [G0] and [G1] for V and [EF0] and [EF1] for $R^7$/q/W/X/Y altogether.

These structural aspects may be permutated with one another as desired in combinations BDEFG, so as to obtain preferred intermediates A-4 (aspects E and F can be replaced by combination aspect EF). Each combination BDEFG represents and defines individual embodiments or generic subsets of intermediates A-4.

In a further aspect the invention also relates to the use of synthetic intermediates of formula A-4 or their salts (and the various embodiments and sub-groups as described and/or defined herein) in the synthesis of compounds (I) or (Ia) or (Ib).

In a further aspect the invention also relates to synthetic intermediates of formula A-5 and their salts, which can be used as key intermediates in the synthesis of compounds of formula (I) or (Ia) or (Ib):

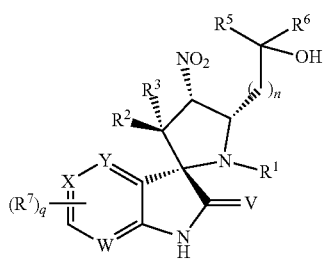

A-5

The definitions of groups R¹, R², R³, R⁵, R⁶, R⁷, V, W, X, Y, n and q in A-5 correspond to those as given for compound (I), (Ia) and (Ib) above, i.e. [A0] for R¹, [B0] for R²/R³, [D0] for R⁵/R⁶/n, [E0] for R⁷/q, [F0] for W/X/Y and [G0] for V.

Preferred intermediates A-5 are those which lead to preferred compounds (I) or (Ia) or (Ib) according to the invention, i.e. preferred embodiments of A-5 have structural aspects selected from [A0] to [A6] for R¹, [B0] to [B11] for R²/R³, [D0] to [D3] for R⁵/R⁶/n, [E0] to [E2] for R⁷/q, [F0] and [F1] for W/X/Y, [G0] and [G1] for V and [EF0] and [EF1] for R⁷/q/W/X/Y altogether. These structural aspects may be permutated with one another as desired in combinations ABDEFG, so as to obtain preferred intermediates A-5 (aspects E and F can be replaced by combination aspect EF). Each combination ABDEFG represents and defines individual embodiments or generic subsets of intermediates A-5.

In a further aspect the invention also relates to the use of synthetic intermediates of formula A-5 or their salts (and the various embodiments and sub-groups as described and/or defined herein) in the synthesis of compounds (I) or (Ia) or (Ib).

In a further aspect the invention also relates to synthetic intermediates of formula A-6 and their salts, which can be used as key intermediates in the synthesis of compounds of formula (I) or (Ia) or (Ib):

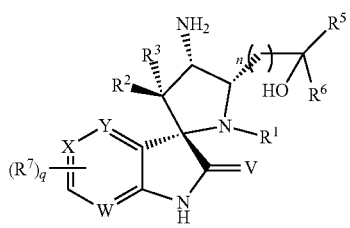

A-6

The definitions of groups R¹, R², R³, R⁵, R⁶, R⁷, V, W, X, Y, n and q in A-6 correspond to those as given for compound (I), (Ia) and (Ib) above, i.e. [A0] for R¹, [B0] for R²/R³, [D0] for R⁵/R⁶/n, [E0] for R⁷/q, [F0] for W/X/Y and [G0] for V.

Preferred intermediates A-6 are those which lead to preferred compounds (I) or (Ia) or (Ib) according to the invention, i.e. preferred embodiments of A-6 have structural aspects selected from [A0] to [A6] for R¹, [B0] to [B11] for R²/R³, [D0] to [D3] for R⁵/R⁶/n, [E0] to [E2] for R⁷/q, [F0] and [F1] for W/X/Y, [G0] and [G1] for V and [EF0] and [EF1] for R⁷/q/W/X/Y altogether. These structural aspects may be permutated with one another as desired in combinations ABDEFG, so as to obtain preferred intermediates A-6 (aspects E and F can be replaced by combination aspect EF). Each combination ABDEFG represents and defines individual embodiments or generic subsets of intermediates A-6.

In a further aspect the invention also relates to the use of synthetic intermediates of formula A-6 or their salts (and the various embodiments and sub-groups as described and/or defined herein) in the synthesis of compounds (I) or (Ia) or (Ib).

In a further aspect the invention also relates to synthetic intermediates of formula A-8 and their salts, which can be used as key intermediates in the synthesis of compounds of formula (I) or (Ia) or (Ib):

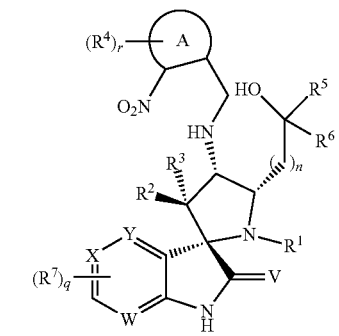

A-8

The definitions of groups R¹, R², R³, R⁴, R⁵, R⁶, R⁷, A, V, W, X, Y, n, q and r in A-8 correspond to those as given for compound (I), (Ia) and (Ib) above, i.e. [A0] for R¹, [B0] for R²/R³, [C0] for A/R⁴/r, [D0] for R⁵/R⁶/n, [E0] for R⁷/q, [F0] for W/X/Y and [G0] for V.

Preferred intermediates A-8 are those which lead to preferred compounds (I) or (Ia) or (Ib) according to the invention, i.e. preferred embodiments of A-8 have structural aspects selected from [A0] to [A6] for R¹, [B0] to [B11] for R²/R³, [C0] to [C9] for A/R⁴/r, [D0] to [D3] for R⁵/R⁶/n, [E0] to [E2] for R⁷/q, [F0] and [F1] for W/X/Y, [G0] and [G1] for V and [EF0] and [EF1] for R⁷/q/W/X/Y altogether. These structural aspects may be permutated with one another as desired in combinations ABCDEFG, so as to obtain preferred intermediates A-8 (aspects E and F can be replaced by combination aspect EF). Each combination ABCDEFG represents and defines individual embodiments or generic subsets of intermediates A-8.

In a further aspect the invention also relates to the use of synthetic intermediates of formula A-8 or their salts (and the various embodiments and sub-groups as described and/or defined herein) in the synthesis of compounds (I) or (Ia) or (Ib).

In a further aspect the invention also relates to synthetic intermediates of formula A-9 and their salts, which can be used as key intermediates in the synthesis of compounds of formula (I) or (Ia) or (Ib):

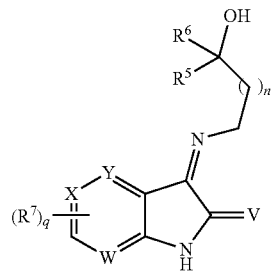

A-9

The definitions of groups $R^5$, $R^6$, $R^7$, V, W, X, Y, n and q in A-9 correspond to those as given for compound (I), (Ia) and (Ib) above, i.e. [D0] for $R^5/R^6$/n, [E0] for $R^7$/q, [F0] for W/X/Y and [G0] for V.

Preferred intermediates A-9 are those which lead to preferred compounds (I) or (Ia) or (Ib) according to the invention, i.e. preferred embodiments of A-9 have structural aspects selected from [D0] to [D3] for $R^5/R^6$/n, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations DEFG, so as to obtain preferred intermediates A-9 (aspects E and F can be replaced by combination aspect EF). Each combination DEFG represents and defines individual embodiments or generic subsets of intermediates A-9.

In a further aspect the invention also relates to the use of synthetic intermediates of formula A-9 or their salts (and the various embodiments and sub-groups as described and/or defined herein) in the synthesis of compounds (I) or (Ia) or (Ib).

The present invention further relates to hydrates, solvates, polymorphs, metabolites, derivatives, isomers and prodrugs of a compound of formula (I) or (Ia) or (Ib).

Compounds of formula (I) or (Ia) or (Ib) which e.g. bear ester groups are potential prodrugs the ester being cleaved under physiological conditions.

The present invention further relates to a pharmaceutically acceptable salt of a compound of formula (I) or (Ia) or (Ib).

The present invention further relates to a co-crystal, preferably a pharmaceutically acceptable co-crystal, of a compound of formula (I) or (Ia) or (Ib).

In one aspect compounds (I), (Ia) and (Ib) according to the invention are in amorphous form.

The present invention further relates to a pharmaceutically acceptable salt of a compound of formula (I) or (Ia) or (Ib) with an organic or organic acids or bases.

The present invention is directed to compounds of formula (I) or (Ia) or (Ib) which are useful in the prevention and/or treatment of a disease and/or condition wherein the inhibition of the interaction between MDM2 and p53 is of therapeutic benefit, including but not limited to the treatment and/or prevention of cancer.

In another aspect the invention relates to a compound of formula (I) or (Ia) or (Ib)—or a pharmaceutically acceptable salt thereof—as a medicament.

In another aspect the invention relates to a compound of formula (I) or (Ia) or (Ib)—or a pharmaceutically acceptable salt thereof—for use in a method for treatment of the human or animal body.

In another aspect the invention relates to a compound of formula (I) or (Ia) or (Ib)—or a pharmaceutically acceptable salt thereof—for use in the treatment and/or prevention of a disease and/or condition wherein the inhibition of the interaction between MDM2 and p53 is of therapeutic benefit.

In another aspect the invention relates to a compound of formula (I) or (Ia) or (Ib)—or a pharmaceutically acceptable salt thereof—for use in the treatment and/or prevention of cancer, infections, inflammations and autoimmune diseases.

In another aspect the invention relates to a compound of formula (I) or (Ia) or (Ib)—or a pharmaceutically acceptable salt thereof—for use in a method for treatment and/or prevention of cancer, infections, inflammations and autoimmune diseases in the human and animal body.

In another aspect the invention relates to the use of a compound of formula (I) or (Ia) or (Ib)—or a pharmaceutically acceptable salt thereof—for preparing a pharmaceutical composition for the treatment and/or prevention of cancer, infections, inflammations and autoimmune diseases.

In another aspect the invention relates to a compound of formula (I) or (Ia) or (Ib)—or a pharmaceutically acceptable salt thereof—for use in the treatment and/or prevention of cancer.

In another aspect the invention relates to the use of a compound of formula (I) or (Ia) or (Ib)—or a pharmaceutically acceptable salt thereof—for preparing a pharmaceutical composition for the treatment and/or prevention of cancer.

In another aspect the invention relates to a compound of formula (I) or (Ia) or (Ib)—or a pharmaceutically acceptable salt thereof—for use in a method for treatment and/or prevention of cancer in the human or animal body.

In another aspect the invention relates to a compound of formula (I) or (Ia) or (Ib)—or a pharmaceutically acceptable salt thereof—for use in the treatment and/or prevention of acute myeloid leukaemia (AML), prostate cancer and lung cancer, wherein the cancer cells are p53 wild-type.

In another aspect the invention relates to a compound of formula (I) or (Ia) or (Ib)—or a pharmaceutically acceptable salt thereof—for use in the treatment and/or prevention of acute myeloid leukaemia (AML), prostate cancer and lung cancer, wherein the cancer cells are preferably p53 wild-type.

In another aspect the invention relates to the use of a compound of formula (I) or (Ia) or (Ib)—or a pharmaceutically acceptable salt thereof—for preparing a pharmaceutical composition for the treatment and/or prevention of acute myeloid leukaemia (AML), prostate cancer and lung cancer, wherein the cancer cells are p53 wild-type.

In another aspect the invention relates to the use of a compound of formula (I) or (Ia) or (Ib)—or a pharmaceutically acceptable salt thereof—for preparing a pharmaceutical composition for the treatment and/or prevention of acute myeloid leukaemia (AML), prostate cancer and lung cancer, wherein the cancer cells are p53 wild-type.

In another aspect the invention relates to a method for the treatment and/or prevention of a disease and/or condition wherein the inhibition of the interaction between MDM2 and p53 is of therapeutic benefit comprising administering a therapeutically effective amount of a compound of formula (I) or (Ia) or (Ib)—or a pharmaceutically acceptable salt thereof—to a human being.

In another aspect the invention relates to a method for the treatment and/or prevention of cancer comprising administering a therapeutically effective amount of a compound of formula (I) or (Ia) or (Ib)—or a pharmaceutically acceptable salt thereof—to a human being.

In another aspect the invention relates to a pharmaceutical composition comprising at least one compound of formula (I) or (Ia) or (Ib)—or a pharmaceutically acceptable salt thereof—and a pharmaceutically acceptable carrier.

In another aspect the invention relates to a pharmaceutical preparation comprising a compound of formula (I) or (Ia) or (Ib)—or a pharmaceutically acceptable salt thereof—and at least one other cytostatic or cytotoxic active substance, different from formula (I) or (Ia) or (Ib).

In another aspect the invention relates to a compound of formula (I) or (Ia) or (Ib)—or a pharmaceutically acceptable salt thereof—for use in the treatment and/or prevention of cancer, infections, inflammations and autoimmune diseases wherein said compound is administered before, after or together with at least one other cytostatic or cytotoxic active substance.

In another aspect the invention relates to the use of a compound of formula (I) or (Ia) or (Ib)—or a pharmaceutically acceptable salt thereof—for preparing a medicament for the treatment and/or prevention of cancer, infections, inflammations and autoimmune diseases wherein said compound is administered before, after or together with at least one other cytostatic or cytotoxic active substance.

In another aspect the invention relates to a cytostatic or cytotoxic active substance prepared for being administered before, after or together with a compound of formula (I) or (Ia) or (Ib)—or a pharmaceutically acceptable salt thereof—for use in the treatment and/or prevention of cancer, infections, inflammations and autoimmune diseases.

In another aspect the invention relates to a method for the treatment and/or prevention of cancer, infections, inflammations and autoimmune diseases comprising administering a therapeutically effective amount of a compound of formula (I) or (Ia) or (Ib)—or a pharmaceutically acceptable salt thereof—before, after or together with at least one other cytostatic or cytotoxic active substance to a human being.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_3$))—, —(CH(CH(CH$_3$))$_2$)—and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene. The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners.

Formally, the second valency is formed by removing a hydrogen atom from a haloalkyl (haloalkenyl, haloalkynyl).

Corresponding groups are for example —CH$_2$F and —CHF—, —CHFCH$_2$F and —CHFCHF— or >CFCH$_2$F etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in C$_{x-y}$cycloalkylamino, C$_{x-y}$cycloalkyloxy or C$_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:
cyclohexyl and

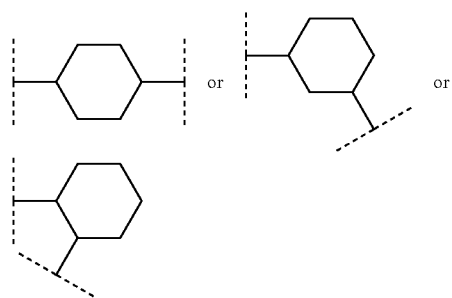

(cyclohexylene).

The above definition for cycloalkylene also applies if cycloalkylene is part of another (combined) group as for example in HO—C$_{x-y}$cycloalkyleneamino or H$_2$N—C$_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in C$_{x-y}$cycloalkenylamino, C$_{x-y}$cycloalkenyloxy or C$_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:
cyclopentenyl and

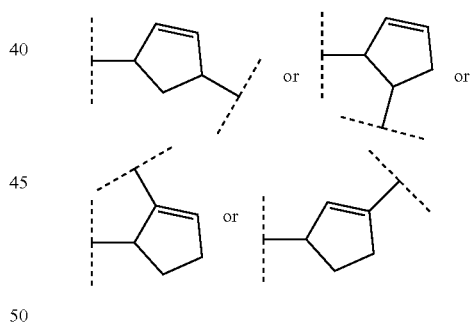

(cyclopentenylene) etc.

The above definition for cycloalkenylene also applies if cycloalkenylene is part of another (combined) group as for example in HO—C$_{x-y}$cycloalkenyleneamino or H$_2$N—C$_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

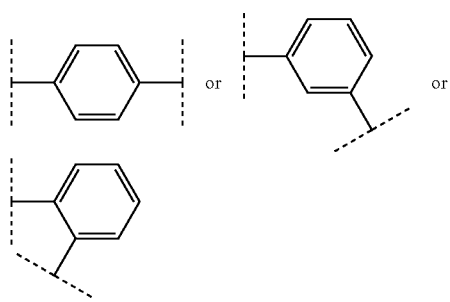

(o, m, p-phenylene),
naphthyl and

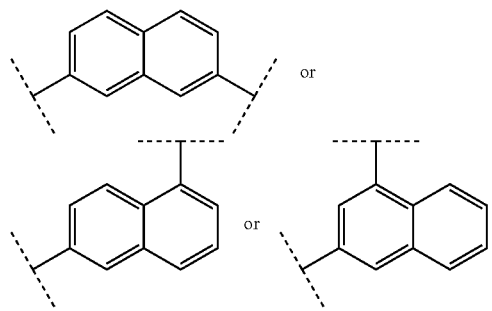

etc.

The above definition for arylene also applies if arylene is part of another (combined) group as for example in HO-aryleneamino or H$_2$N-aryleneoxy.

Heterocyclyl denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro[4,5]decyl etc.

Further examples are the structures illustrated below, which may be attached via each hydrogen-carrying atom (exchanged for hydrogen):

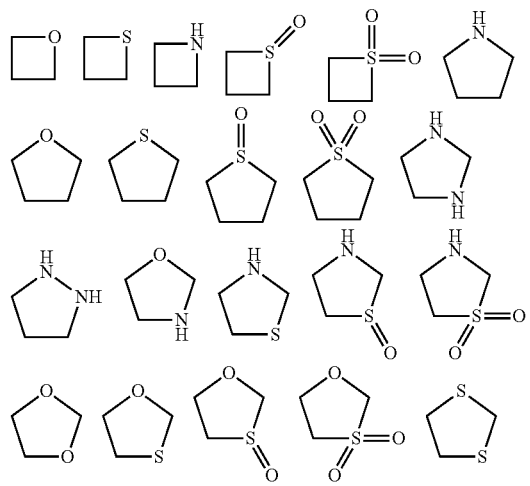

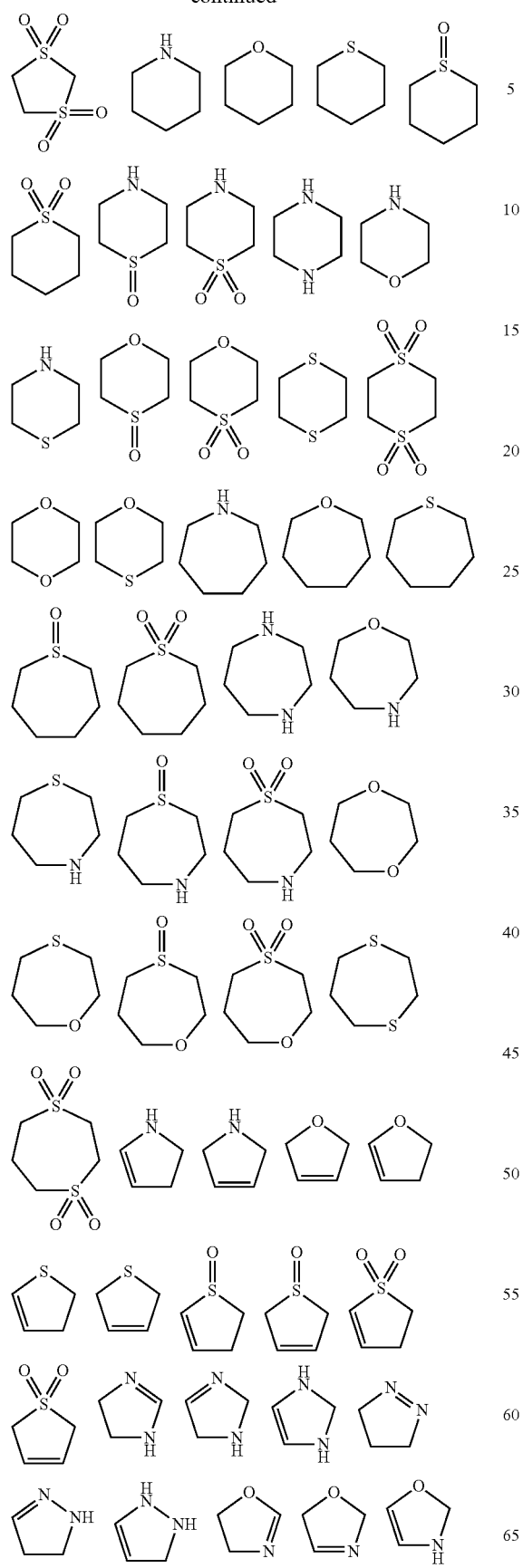
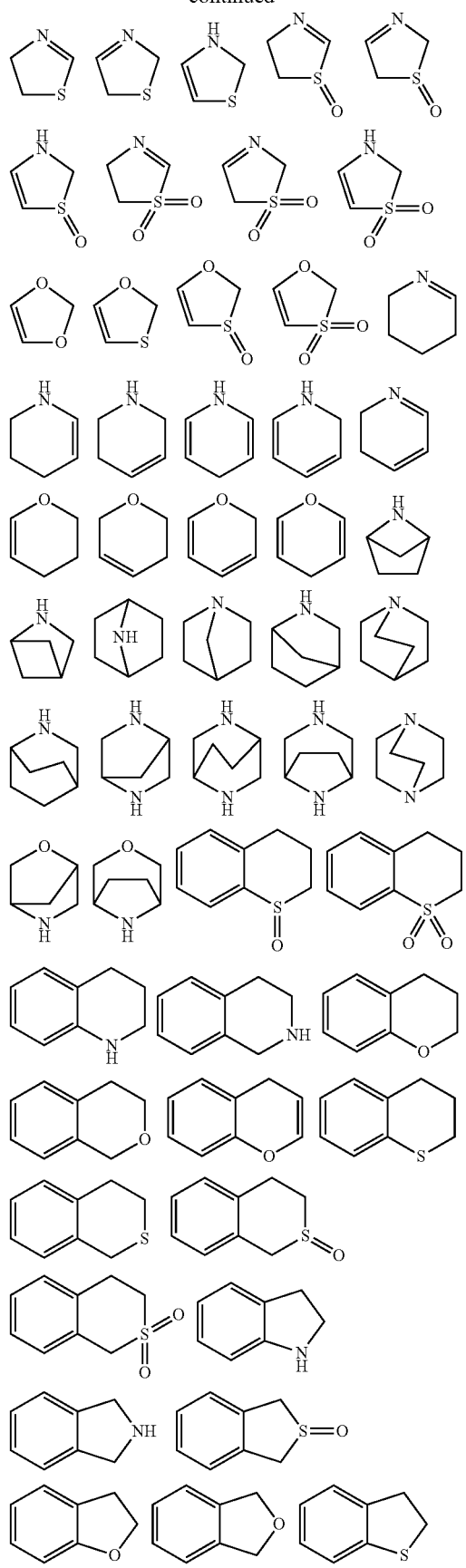

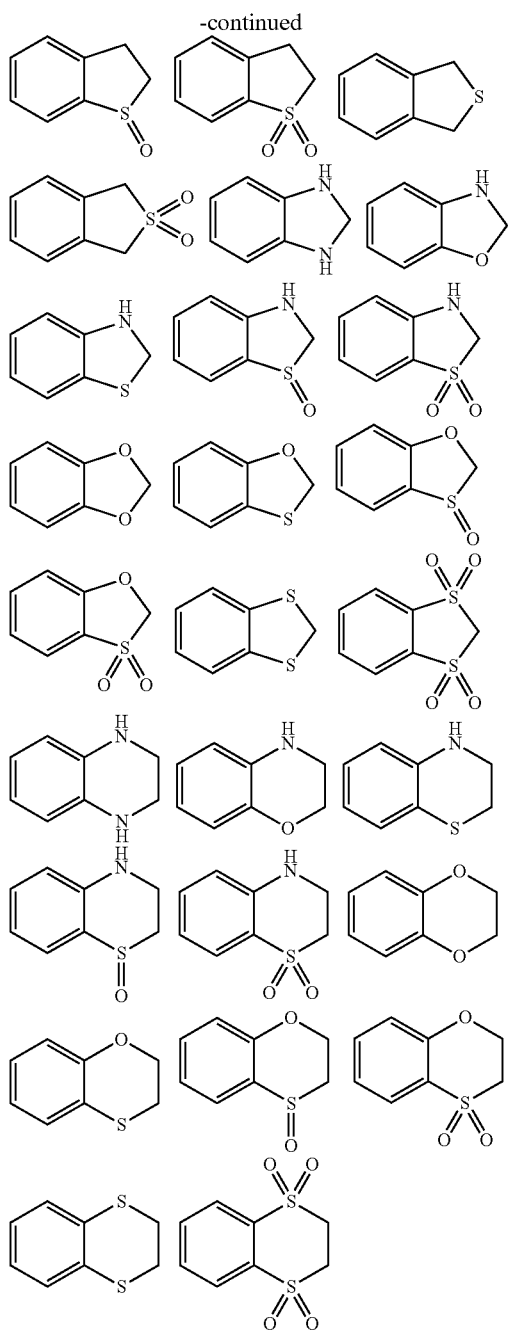

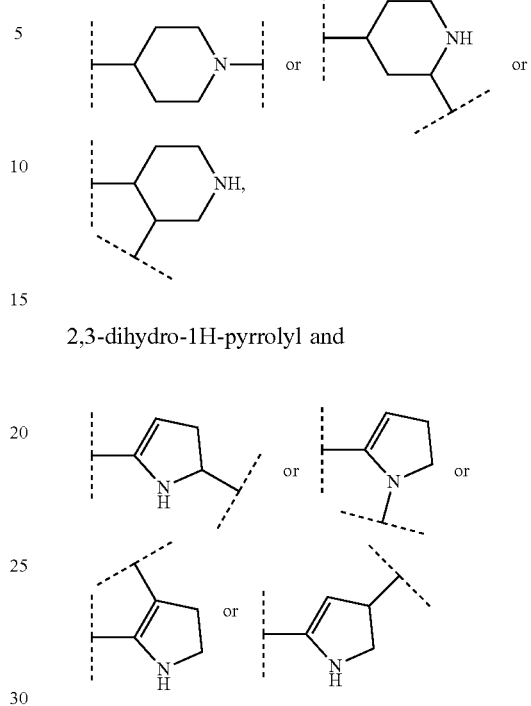

piperidinyl and 2,3-dihydro-1H-pyrrolyl and etc.

The above definition of heterocyclylene also applies if heterocyclylene is part of another (combined) group as for example in HO-heterocyclyleneamino or H₂N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-

Preferably, heterocyclyls are 4 to 8 membered, monocyclic and have one or two heteroatoms independently selected from oxygen, nitrogen and sulfur Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

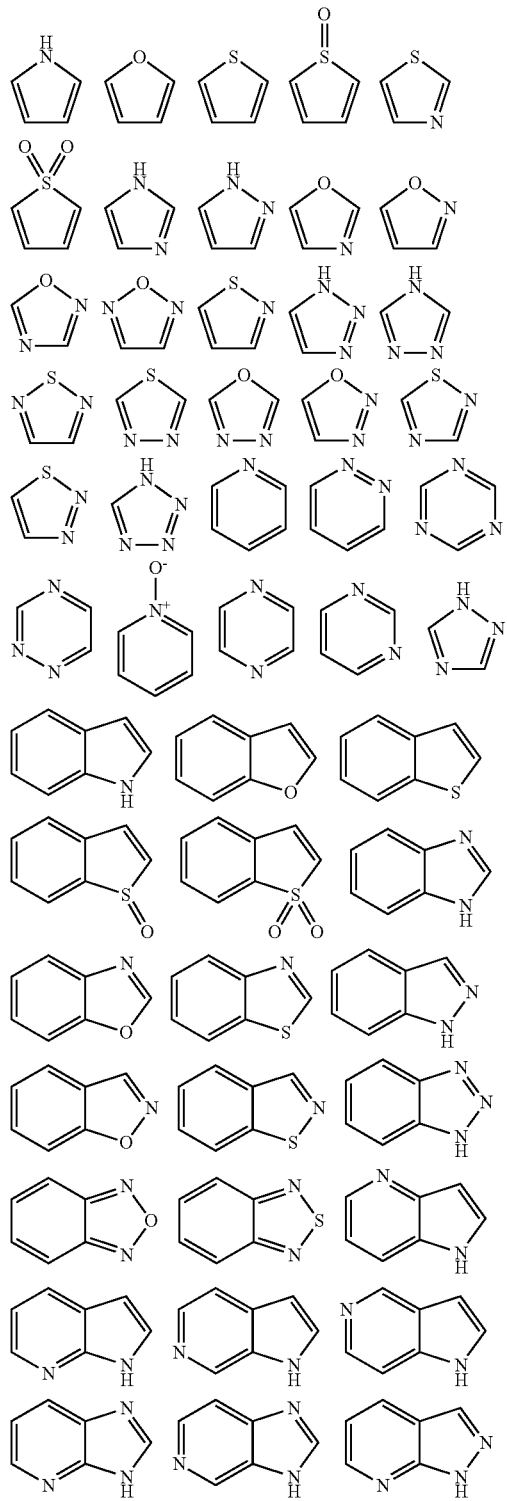

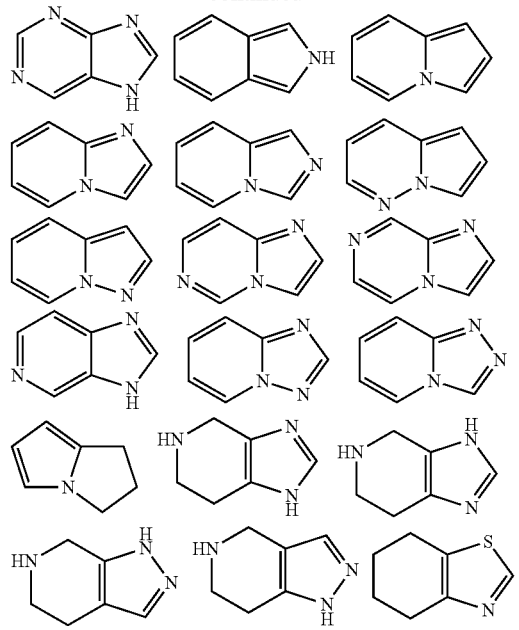

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example: pyrrolyl and

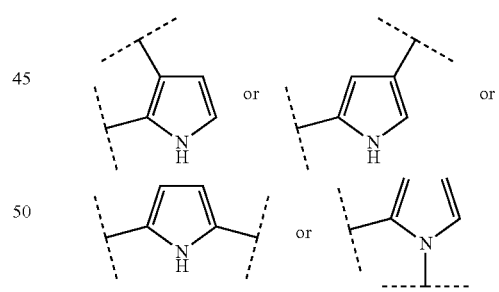

etc.

The above definition of heteroarylene also applies if heteroarylene is part of another (combined) group as for example in HO-heteroarylenamino or $H_2N$-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, wherein the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O only) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from ammonia, L-arginine, betaine, benethamine, benzathine, calcium hydroxide, choline, deanol, diethanolamine (2,2'-iminobis (ethanol)), diethylamine, 2-(diethylamino)-ethanol, 2-(dimethylamino)-ethanol, 2-aminoethanol, ethylenediamine, N-ethyl-glucamine, hydrabamine, 1H-imidazole, lysine (L-lysine), proline (L-proline), magnesium hydroxide, 4-(2-hydroxyethyl)-morpholine, morpholine, piperazine, potassium hydroxide, 1-(2-hydroxyethyl)-pyrrolidine, 1-(2-hydroxyethyl)-pyrrolidone, sodium hydroxide, triethanolamine (2,2',2"-nitrilotris(ethanol), tromethamine, zinc hydroxide, acetic acid, 2,2-dichloro acetic acid, adipic acid, alginic acid, ascorbic acid (L), L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid (capric acid), dodecylsulfuric acid, ethane-1,2-disulfonic acid, ethanesulfonic acid, 2-hydroxyethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid (caproic acid), hippuric acid, hydrobromic acid, hydrochloric acid, isobutyric acid, DL-lactic acid, lactobionic acid, lauric acid, maleic acid, (-)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, octanoic acid (caprylic acid), oleic acid, orotic acid, oxalic acid, palmitic acid, pamoic acid (embonic acid), phosphoric acid, propionic acid, (-)-L-pyroglutamic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid and undecylenic acid.

The salts include acetates, ascorbates, benzenesulfonates, benzoates, besylates, bicarbonates, bitartrates, bromides/hydrobromides, Ca-edetates/edetates, camsylates, carbonates, camphorsulfonate, chlorides/hydrochlorides, chlorotheophyllinate, citrates, edisylates, ethane disulfonates, estolates esylates, fumarates, gluceptates, gluconates, glucuronate, glutamates, glycolates, glycollylarsnilates, hexylresorcinates, hippurate, hydrabamines, hydroxymaleates, hydroxynaphthoates, iodides, isethionates, isothionates, lactates, lactobionates, laurylsulfates, malates, maleates, mandelates, methanesulfonates, mesylates, methylbromides, methylnitrates, methylsulfates, mucates, naphthoate, napsylates, nitrates, octadecanoates, oleates, oxalates, pamoates, pantothenates, phenylacetates, phosphates/diphosphates, polygalacturonates, propionates, salicylates, stearates subacetates, succinates, sulfamides, sulfates, sulfosalicylates, tannates, tartrates, teoclates, toluenesulfonates, triethiodides, trifluoroacetates, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

The present invention also includes the co-crystals of any compound according to the invention, i.e. those crystalline forms composed of at least two components (one being the compound according to the invention, the other being co-crystal formers) forming a unique crystalline structure without, in contrast to the crystalline salts, proton transfer from one component to the other. Potential co-crystal formers are acids and bases as listed above for salts/salt formers.

In a representation such as for example

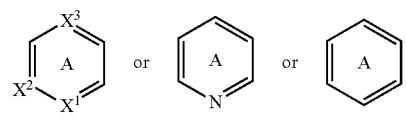

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

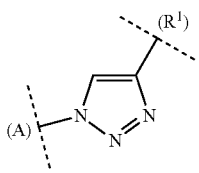

or $(R^2)$ —C(O)NH— or $(R^2)$ —NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of abbreviations

| | |
|---|---|
| Ac | acetyl |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| Et₂O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |

-continued

List of abbreviations

| | |
|---|---|
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf (R$_f$) | retention factor |
| RP | reversed phase |
| rt | ambient temperature |
| SFC | supercritical fluid chromatography |
| S$_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| t$_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 μm, 50×150 mm or SunFire™ Prep C18 OBD™ 5 μm, 30×50 mm or XBridge™ Prep C18, OBD™ 10 μm, 50×150 mm or XBridge™ Prep C18, OBD™ 5 μm, 30×150 mm or XBridge™ Prep C18, OBD™ 5 μm, 30×50 mm) and YMC (names: Actus-Triart Prep C18, 5 μm, 30×50 mm).

Different gradients of $H_2O$/acetonitrile are used to elute the compounds, while for Agilent systems 5% acidic modifier (20 mL HCOOH to 1 L $H_2O$/acetonitrile (1/1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following columns: Chiralcel OJ (250×20 mm, 5 μm), Chiralpak AD (250×20 mm, 5 μm), Chiralpak AS (250×20 mm, 5 μm), Chiralpak IC (250×20 mm, 5 μm), Chiralpak IA (250×20 mm, 5 μm), Chiralcel OJ (250×20 mm, 5 μm), Chiralcel OD (250×20 mm, 5 μm), Phenomenex Lux C2 (250×20 mm, 5 μm).

The analytical HPLC (reaction control) of intermediate and final compounds is carried out using columns made by Waters (names: XBridge™ C18, 2.5 μm, 2.1×20 mm or XBridge™ C18, 2.5 μm, 2.1×30 mm or Aquity UPLC BEH C18, 1.7 μM, 2.1×50 mm) and YMC (names: Triart C18, 3.0 μm, 2.0×30 mm). The analytical equipment is also equipped with a mass detector in each case.

HPLC-Mass Spectroscopy/UV-Spectrometry

The retention times/MS-ESI$^+$ for characterizing the example compounds according to the invention are produced using an HPLC-MS apparatus (high performance liquid chromatography with mass detector). Compounds that elute at the injection peak are given the retention time $t_{Ret}$=0.00.

HPLC-Methods

Method A

| | |
|---|---|
| HPLC | Agilent 1100 Series |
| MS | Agilent LC/MSD SL |
| column | Waters, Xbridge ™ C18, 2.5 μm, 2.1 × 20 mm, Part. No. 186003201 |
| solvent | A: 20 mM $NH_4HCO_3$/$NH_3$ pH 9 |
| | B: acetonitrile (HPLC grade) |
| detection | MS: positive and negative |
| | mass range: 120-900 m/z |
| | fragmentor: 120 |
| | gain EMV: 1 |
| | threshold: 150 |
| | stepsize: 0.2 |
| | UV: 315 nm |
| | bandwidth: 170 nm |
| | reference: off |
| | range: 230-400 nm |
| | range step: 1.00 nm |
| | peakwidth: <0.01 min |
| | slit: 1 nm |
| injection | 5 μL |
| flow | 1.00 mL/min |
| column temperature | 60° C. |
| gradient | 0.00 min 10% B |
| | 0.00-1.50 min 10% → 95% B |
| | 1.50-2.00 min 95% B |
| | 2.00-2.10 min 95% → 10% B |

Method B

| | |
|---|---|
| HPLC | Agilent 1200 Series |
| MS | Agilent 6130 Quadropole LC/MS |
| column | Waters, Xbridge ™ C18, 2.5 μm, 2.1 × 30 mm |
| solvent | A: 20 mM $NH_4HCO_3$/$NH_3$ in water; pH 9.3 |
| | B: acetonitrile (HPLC grade) |
| detection | MS: |
| | polarity: positive |
| | ionizator: MM-ES + APCI |
| | mass range: 150-750 m/z |
| | fragmentor values: |

| mass | fragmentor |
|---|---|
| 150 | 70 |
| 750 | 110 |

| | |
|---|---|
| | gain EMV: 1.00 |
| | threshold: 150 |
| | stepsize: 0.2 |
| | UV: |
| | 254 nm: reference off |
| | 214 nm: reference off |
| | range: 190-400 nm |
| | range step: 2.00 nm |
| | threshold: 1.00 mAU |
| | peakwidth: 0.0025 min (0.05 s) |
| | slit: 4 nm |
| injection | 0.5 μL |
| flow | 1.400 mL/min |
| column temperature | 45° C. |
| gradient | 0.00-1.00 min 15% –> 95% B |
| | 1.00-1.30 min 95% B |

Method C

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH |
| | B: acetonitrile + 0.1% HCOOH (HPLC grade) |
| detection | MS: |
| | polarity: positive |
| | mass range: 150-750 m/z |
| | fragmentor values: |

| mass | fragmentor |
|---|---|
| 150 | 70 |
| 750 | 110 |

| | |
|---|---|
| | gain EMV: 1.00 |
| | threshold: 150 |
| | stepsize: 0.20 |
| | UV: |
| | 254 nm: reference off |
| | 214 nm: reference off |
| | range: 190-400 nm |
| | range step: 4.00 nm |
| | threshold: 1.00 mAU |
| | peakwidth: 0.005 min (0.1 s) |
| | slit: 4 nm |
| injection | 0.5 μL |
| flow | 1.400 mL/min |
| column temperature | 45° C. |
| gradient | 0.00-1.00 min 15% → 100% B |
| | 1.00-1.13 min 100% B |

Method D

| | |
|---|---|
| HPLC | Agilent 1200 Series |
| MS | Agilent 6130 Quadropole LC/MS |
| column | Waters, Xbridge ™ C18, 2.5 μm, 2.1 × 30 mm |

-continued

| | |
|---|---|
| solvent | A: 20 mM NH₄HCO₃/NH₃ in water; pH 9.3<br>B: acetonitrile (HPLC grade) |
| detection | MS:<br>polarity: positive + negative<br>ionization: MM-ES<br>mass range: 150-750 m/z<br>fragmentor values: |

| mass | fragmentor |
|---|---|
| 150 | 70 |
| 750 | 110 | gain EMV: 1.00
threshold: 150
stepsize: 0.2
UV:
254 nm: reference off
214 nm: reference off
range: 190-400 nm
range step: 2.00 nm
threshold: 1.00 mAU
peakwidth: 0.0025 min (0.05 s)
slit: 4 nm

| | |
|---|---|
| injection | 0.5 μL |
| flow | 1.400 mL/min |
| column temperature | 45° C. |
| gradient | 0.00-1.00 min 15% → 95% B<br>1.00-1.30 min 95% B |

Method E

| | |
|---|---|
| HPLC | Agilent 1200 Series: |
| MS | Agilent 6130 Quadropole LC/MS |
| column | Waters, Xbridge ™ C18, 2.5 μm,<br>2.1 × 30 mm Column XP; Part. No. 186006028 |
| solvent | A: 20 mM NH₄HCO₃/NH₃ in water; pH 9.3<br>B: acetonitrile (HPLC grade) |
| detection | MS:<br>polarity: positive + negative<br>ionizator: API-ES<br>mass range: 150-750 m/z<br>fragmentor values: |

| mass | fragmentor |
|---|---|
| 150 | 70 |
| 750 | 110 | gain EMV: 1.00
threshold: 150
stepsize: 0.2
UV:
254 nm: reference off
214 nm: reference off
range: 190-400 nm
range step: 2.00 nm
threshold: 1.00 mAU
peakwidth: 0.0025 min (0.05 s)
slit: 4 nm

| | |
|---|---|
| injection | 0.5 μL |
| flow | 1.400 mL/min |
| column temperature | 45° C. |
| gradient | 0.00-1.00 min 15% → 95% B<br>1.00-1.30 min 95% B |

Method F

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH<br>B: acetonitrile + 0.1% HCOOH (HPLC grade) |
| detection | MS:<br>polarity: positive + negative<br>mass range: 150-750 m/z<br>fragmentor values: |

| mass | fragmentor |
|---|---|
| 150 | 70 |
| 750 | 110 | gain EMV: 1.00
threshold: 150
stepsize: 0.20
UV:
254 nm: reference off
214 nm: reference off
range: 190-400 nm
range step: 4.00 nm
threshold: 1.00 mAU
peakwidth: 0.0063 min (0.13 s)
slit: 4 nm

| | |
|---|---|
| injection | 0.5 μL |
| flow | 1.400 mL/min |
| column temperature | 45° C. |
| gradient | 0.00-1.00 min 15% → 100% B<br>1.00-1.13 min 100% B |

Method G

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH<br>B: acetonitrile + 0.1% HCOOH (HPLC grade) |
| detection | MS:<br>polarity: positive + negative<br>mass range: 150-750 m/z<br>fragmentor values: |

| Mass | Fragmentor |
|---|---|
| 150 | 70 |
| 750 | 110 | gain EMV: 1.00
threshold: 150
stepsize: 0.20
UV:
254 nm: reference off
230 nm: reference off
214 nm: reference off
range: 190-400 nm
range step: 4.00 nm
threshold: 1.00 mAU
peakwidth: 0.005 min (0.1 s)
slit: 4 nm

| | |
|---|---|
| injection | 0.5 μL |
| flow | 1.400 mL/min |
| column temperature | 45° C. |
| gradient | 0.00-1.00 min 15% → 100% B<br>1.00-1.13 min 100% B |

Method H

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH<br>B: acetonitrile + 0.1% HCOOH (HPLC grade) |
| detection | MS:<br>polarity: positive + negative<br>mass range: 200-800 m/z<br>fragmentor: 70<br>gain: 1.00 |

Method I

| | |
|---|---|
| HPLC | Agilent 1200 Series |
| MS | Agilent 6130 Quadropole LC/MS |
| column | YMC, Triart C18, 3.0 µm, 2.0 × 30 mm, 12 nm |
| solvent | A: water + 0.1% HCOOH |
| | B: acetonitrile + 0.1% HCOOH (HPLC grade) |
| detection | MS: |
| | polarity: positive + negative |
| | mass range: 200-800 m/z |
| | fragmentor: 70 |
| | gain: 1.00 |
| | threshold: 150 |
| | stepsize: 0.20 |
| | UV: |
| | 254 nm: reference off |
| | 230 nm: reference off |
| | range: 190-400 nm |
| | range step: 2.00 nm |
| | peakwidth: >0.01 min (0.2 s) |
| | slit: 4 nm |
| injection | 1.0 µL |
| flow | 1.000 mL/min |
| column temperature | 45° C. |
| gradient | 0.00-0.10 min 15% B |
| | 0.10-1.55 min 15% B → 95.0% B |
| | 1.55-1.90 min 95% B |
| | 1.95-1.92 min 95% B → 15.0% B |

Method J

| | |
|---|---|
| HPLC | Agilent 1260 Series |
| MS | Agilent 6130 Quadropole LC/MS |
| column | YMC, Triart C18, 3.0 µm, 2.0 × 30 mm, 12 nm |
| solvent | A: water + 0.1% HCOOH |
| | B: acetonitrile (HPLC grade) |
| detection | MS: |
| | polarity: positive + negative |
| | mass range: 100-800 m/z |
| | fragmentor: 70 |
| | gain: 1.00 |
| | threshold: 100 |
| | stepsize: 0.15 |
| | UV: |
| | 254 nm: reference off |
| | 230 nm: reference off |
| | range: 190-400 nm |
| | range step: 4.00 nm |
| | peakwidth: >0.013 min (0.25 s) |
| | slit: 4 nm |
| injection | 0.5 µL |
| flow | 1.400 mL/min |
| column temperature | 45° C. |
| gradient | 0.00-1.00 min 5% → 100% B |
| | 1.00-1.37 min 100% B |
| | 1.37-1.40 min 100% → 5% B |

Method K

| | |
|---|---|
| HPLC | Agilent 1260 Series |
| MS | Agilent 6130 Quadropole LC/MS |
| column | Waters, Xbridge ™ C18, 2.5 µm, 2.1 × 30 mm |
| solvent | A: 5 mM $NH_4HCO_3$/19 mM $NH_3$ in water |
| | B: acetonitrile (HPLC grade) |
| detection | MS: |
| | polarity: positive + negative |
| | mass range: 100-800 m/z |
| | fragmentor: 70 |
| | gain: 1.00 |
| | threshold: 100 |
| | stepsize: 0.15 |
| | UV: |
| | 254 nm: reference off |
| | 230 nm: reference off |
| | range: 190-400 nm |
| | range step: 4.00 nm |
| | peakwidth: >0.013 min (0.25 s) |
| | slit: 4 nm |
| injection | 0.5 µL |
| flow | 1.400 mL/min |
| column temperature | 45° C. |
| gradient | 0.00-0.01 min 5% B |
| | 0.01-1.00 min 5% → 100% B |
| | 1.00-1.37 min 100% B |
| | 1.37-1.40 min 100% → 5% B |

Method L

| | |
|---|---|
| HPLC/MS | Waters UPLC-micromass Triple quad |
| column | Aquity UPLC BEH C18, 1.7 µM, 2.1 × 50 mm |
| solvent | A: water + 0.1% HCOOH |
| | B: acetonitrile (HPLC grade) + 0.1% HCOOH |
| detection | MS: |
| | ES/APCI positive and negative mode |
| | mass range: 100-1000 m/z |
| | capillary voltage: 3500 V |
| | cone voltage: 30-50 V |
| | disolvation gas: 600 L/h |
| | disolvation temp: 300° C. |
| | UV: |
| | bandwidth: 190 nm |
| | range: 210-400 nm |
| | resolution: 1.20 nm |
| | sample rate: 5 |
| injection | 0.5 µL |
| flow | 0.400 mL/min |
| column temperature | 40° C. |
| gradient | 0.00-1.80 min 0% B |
| | 1.80-3.80 min 0% → 75% B |
| | 3.80-4.50 min 75% → 95% B |
| | 4.50-6.00 min 95% B |
| | 6.00-6.01 min 95% → 0% B |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known prior art compounds or methods described herein. Substances described in the literature are prepared according to the published methods of synthesis.

General Reaction Scheme and Summary of the Synthesis Route

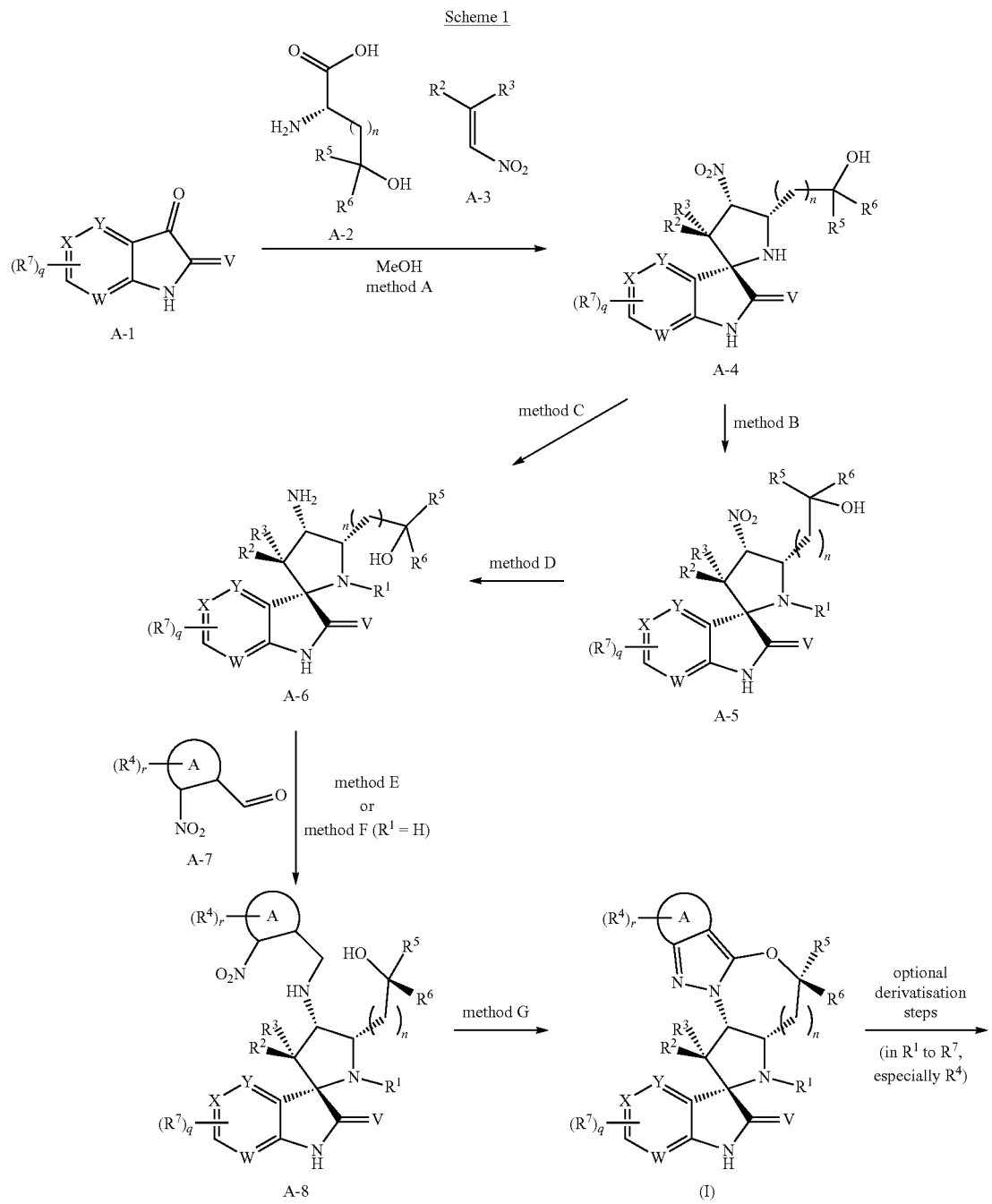

Scheme 1

Novel compounds of structure (I) can be prepared stepwise starting with a synthesis route depicted in scheme 1 from compounds A-1 via a decarboxylative 1,3 dipolar cycloaddition with an amino acid A-2 and a nitro ethene A-3 (method A) to build up spiro systems A-4 as a racemic mixture potentially along with other regio- and/or diastereoisomers of A-4. The enantiomers of A-4 can be separated at this stage by chiral SFC or alternatively the racemic mixture can be separated at any later stage of the synthesis. Also all other means known for separation of enantiomers can be applied here or after any later synthetic step herein described, e.g. crystallisation, chiral resolution, chiral HPLC etc. (see also *Enantiomers, racemates, and resolutions*, Jean Jacques, André Collet, Samuel H Wilen John Wiley and Sons, N Y, 1981).

A-4 can be reacted with aldehydes or ketones in a reductive amination reaction to give A-5 (method B). Alternatively, an alkylation or addition reaction can be performed with A-4 to obtain intermediates A-5.

The nitro group in intermediate A-5 can be reduced to the primary amine by hydrogenation under RANEY nickel catalysis or any suitable alternative reduction method like e.g. indium metal and hydrochloric acid, to obtain intermediates of structure A-6. Alternatively, intermediates A-6 (with R¹=H) can be obtained directly from A-4 by (method C) hydrogenation under RANEY nickel catalysis or any suitable alternative reduction method like e.g. indium metal and hydrochloric acid.

Intermediate A-6 is reacted with (hetero)aromatic nitro aldehyde A-7 in a reductive amination reaction to yield intermediate A-8 (method E). For intermediates A-6 with R¹=H, method F can be used to selectively introduce two different residues on the primary and secondary amino function by a sequence of two reductive amination reactions in one pot to obtain intermediates A-8. Intermediate A-8 is treated with base to undergo a DAVIS-BEIRUT reaction to yield compounds (I)

Compounds (I) which are obtained from A-8 after intramolecular cyclization can be derivatized in optional derivatization steps not explicitly depicted in the schemes in all residues, especially in $R^4$, if they carry functional groups, that can be further modified such as e.g. halogen atoms, amino and hydroxy groups (including cyclic amines), carboxylic acid or ester functions, nitrils etc. to further compounds (I) by well established organic chemical transformations such as metal-catalyzed cross coupling reactions, acylation, amidation, addition, reduction or (reductive) alkylation or cleavage of protecting groups. These additional steps are not depicted in the general schemes. Likewise, it is also possible to include these additional steps in the synthetic routes depicted in the general schemes, i.e. to carry out derivatization reactions with intermediate compounds. In addition, it is also possible to use building blocks bearing protecting groups, i.e. further steps for deprotection are necessary. Compounds (I) have been tested for their activity to affect MDM2-p53 interaction in their racemic form or alternatively as the enantiopure form. Each of the two enantiomers of a racemic mixture may have activity against MDM2 although with a different binding mode. Enantiopure compounds are marked with the label "Chiral". Compounds listed in any table below that are labeled "Chiral" (both intermediates as well as compounds (I) according to the invention) can be separated by chiral SFC chromatography from their enantiomer or are synthesized from enantiopure starting material which is separated by chiral SFC.

EXAMPLE

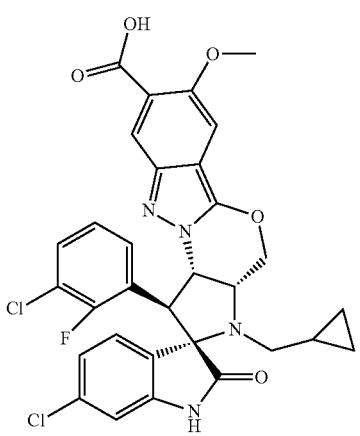

A

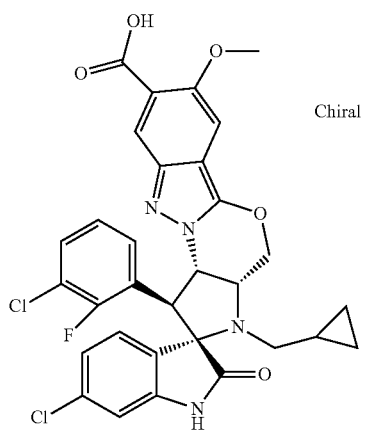

B

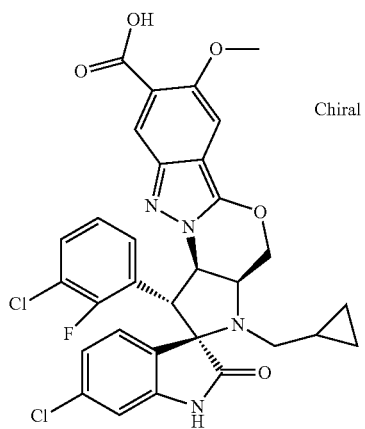

C

Structure A defines the racemic mixture of compounds with structure B and C, i.e. structure A encompasses two structures (compounds B and C), whereas structures B and C, respectively, are enantiopure and only define one specific compound. Thus, formulae (I) and (Ia)

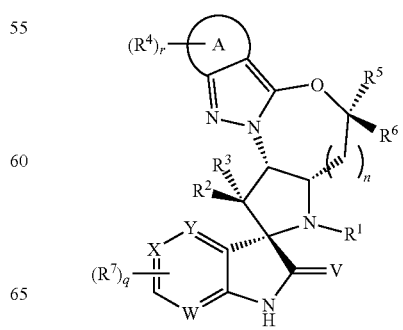

(I)

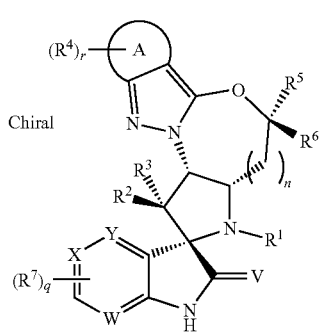

(Ia)

with a set of specific definitions for groups R¹ to R⁷, A, V, W, X, Y, n, r and q represent the racemic mixture of two enantiomers (→(I); structure A above is one specific example of such a racemic mixture) or a single enantiomer (→(Ia); structure B above is one specific enantiomer), unless there are additional stereocenters present in one or more of the substituents. The same definition applies to synthetic intermediates.

In particular, chiral resolution of compounds (I) according to the invention (preferably of those bearing acidic groups) can, e.g., be achieved by crystallization with chiral bases, e.g. (R)- or (S)-1-aminotetra line ((R)- or (S)-1,2,3,4-tetrahydronaphthyl-1-amine), in an appropriate solvent, e.g. isopropyl acetate (i-PrOAc), i.e. chiral compound (Ia) can be precipitated with (S)-1-aminotetraline from a solution or suspension of racemic (I) to form a tetrahydronaphthyl-S salt which can be separated. The salt obtained can be further purified by reslurry in an appropriate solvent, e.g. n-propanol (nPrOH), dioxane, THF, EtOH.

Thus, one aspect of the invention is a method for the chiral separation of compounds (I) according to the invention comprising precipitating a salt of one enantiomer formed with a chiral base, the chiral base preferably selected from among (R)- and (S)-1,2,3,4-tetrahydronaphthyl-1-amine, from a solution or suspension of compounds (I) in an appropriate solvent, preferably iso-propyl acetate. The salt precipitates selectively, i.e. one enantiomer precipitates as a salt of the chiral base whereas the other enantiomer remains/is substantially dissolved under the conditions applied. Preferably, the salt initially obtained is further purified by reslurry in an appropriate solvent, e.g. n-propanol (nPrOH), dioxane, THF, EtOH. The free enantiomer can be recovered from the salt by ion exchange, e.g. by acidic extraction. The method described hereinbefore can also be applied for the enrichment of one enantiomer in relation to the other if complete separation can not be achieved or the steps can be repeated several times to achieve complete separation. Separation means that the respective enantiomer/salt is obtained in a form that is substantially free of the other enantiomer. Preferably, the chiral base is used in sub-stoichiometric amounts in relation to the racemate, i.e. preferably in a range of 0.5-0.7 eq. (about 0.6 eq. being most preferred). The total concentration/amount of racemate in the solution/suspension before separation is preferably in a range of 50-150 g/L, about 100 g/L being most preferred.

Synthesis of Intermediate A-1

Experimental Procedure for the Synthesis of A-1a

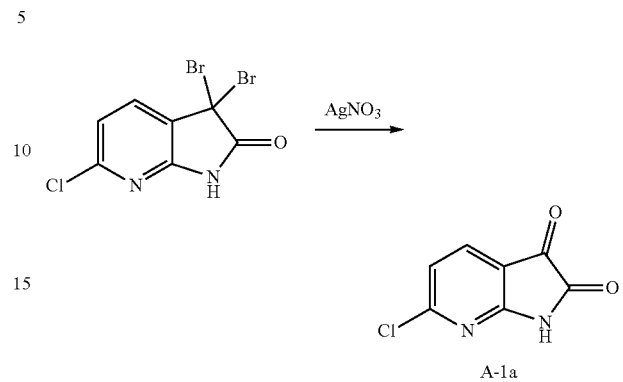

3,3-Dibromo-6-chloro-1,3-dihydro-pyrrolo[2,3-b]pyridin-2-one (7.6 g, 23.3 mmol) is suspended in acetonitrile (500 mL) and water (25 mL). AgNO₃ (8.9 g, 52.7 mmol) is added and the reaction mixture is stirred at rt for 1 h. Acetonitrile is removed under reduced pressure and EtOAc is added. The phases are separated and the organic layer is dried with MgSO₄. Removal of the solvents gives pure 6-chloro-1H-pyrrolo[2,3-b]pyridine-2,3-dione A-1a.

Synthesis of Intermediate A-3

Nitroethenes A-3 which are not commercially available can be obtained from aldehydes/ketones B-1 via nitro aldol reaction with nitromethane and subsequent dehydration of nitro aldol product B-2.

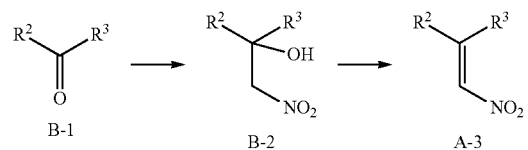

Experimental Procedure for the Synthesis of B-2a

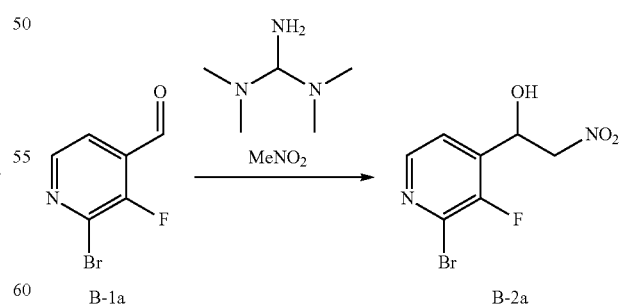

To a solution of 2-bromo-3-fluoro-pyridine-4-carbaldehyde (5.0 g, 24.5 mmol) in nitromethane (45 mL, 1.01 mol) under Ar atmosphere at −20° C. is added N,N,N',N'-tetramethylguanidine (3.1 mL, 24.5 mmol) in nitromethane (5 mL, 0.11 mol). The reaction mixture is stirred for 30 min at −20°

C. Brine is added to the mixture and the product is isolated via extraction with EtOAc and used for the next step without purification.

The following nitroaldols B-2 (table 1) are available in an analogous manner starting from different aldehydes.

TABLE 1

| # | structure | $t_{ret}$ [min] | [M + H]$^+$ | HPLC method |
|---|---|---|---|---|
| B-2a | 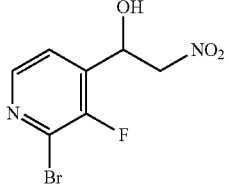 [SMILES: O=[N+]([O-])CC(O)c1ccnc(Br)c1F] | 0.37 | 265/267 | F |
| B-2b | 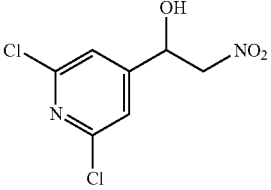 [SMILES: O=[N+]([O-])CC(O)c1cc(Cl)nc(Cl)c1] | 0.621 | 219/221 | F |
| B-2c | 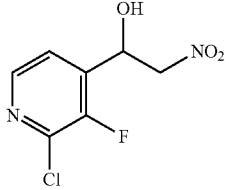 [SMILES: O=[N+]([O-])CC(O)c1ccnc(Cl)c1F] | n.a. | n.a. | n.a. |

Alternative 1: Experimental Procedure for the Synthesis of A-3a

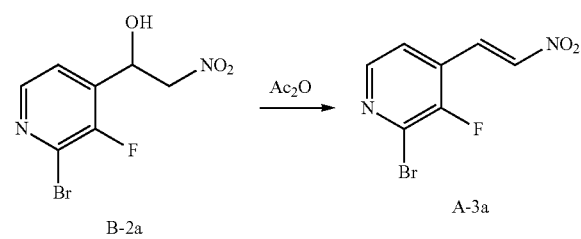 [SMILES: "Ac2O" ; O=[N+]([O-])CC(O)c1ccnc(Br)c1F ; O=[N+]([O-])/C=C/c1ccnc(Br)c1F]

To a solution of 1-(2-bromo-3-fluoro-pyridin-4-yl)-2-nitro-ethanol B-2a (4.82 g, 18.2 mmol) in DMSO (30 mL) is added acetic acid anhydride (3.43 mL, 36.4 mmol) and the reaction mixture is stirred overnight at 50° C. under Ar atmosphere. The reaction mixture is filtered and purified via preparative RP-HPLC yielding 2-bromo-3-fluoro-4-((E)-2-nitro-vinyl)-pyridine A-3a.

The following intermediates A-3 (table 2) are available in an analogous manner starting from different nitroaldols B-2a.

TABLE 2

| # | structure | $t_{ret}$ [min] | [M + H]$^+$ | HPLC method |
|---|---|---|---|---|
| A-3a | 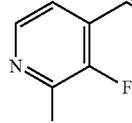 | 0.58 | 247/249 | F |
| A-3b | 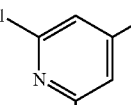 | 0.62 | 219/221 | F |

Alternative 2: Experimental Procedure for the Synthesis of A-3c

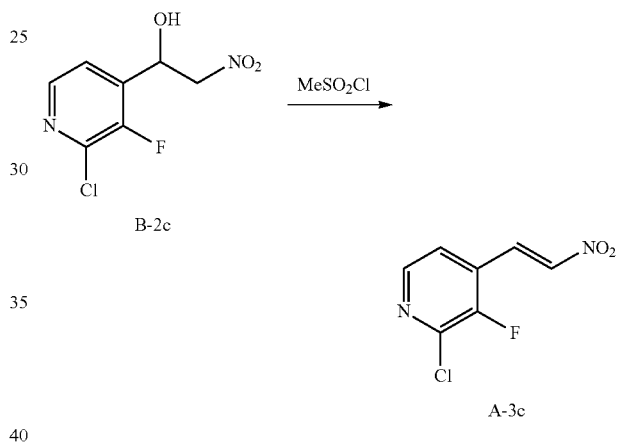

A solution of 1-(2-chloro-3-fluoro-pyridin-4-yl)-2-nitro-ethanol B-2c (200 g, 0.91 mol) in DCM (1.8 L) is cooled to 0° C. and a solution of methanesulfonyl chloride (124 g, 1.09 mol) in DCM (200 mL) is added. The mixture is stirred for 15 min at 0° C. before NEt$_3$ (201 g, 2.0 mol) is added. The reaction mixture is stirred for additional 45 min at 0° C. To the reaction mixture is added saturated sodium bicarbonate solution and the mixture is extracted with DCM. The combined organic layer is dried and the solvent is removed under in vacuo. The product is purified via column chromatography yielding 2-chloro-3-fluoro-4-((E)-2-nitro-vinyl)-pyridine A-3c.

The following intermediates A-3 (table 3) are available in an analogous manner starting from different nitro aldols B-2.

TABLE 3

| # | structure | $t_{ret}$ [min] | [M + H]$^+$ | HPLC method |
|---|---|---|---|---|
| A-3c | 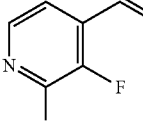 | 0.54 | 203 | E |

Alternative 3: Experimental Procedure for the Synthesis of A-3d

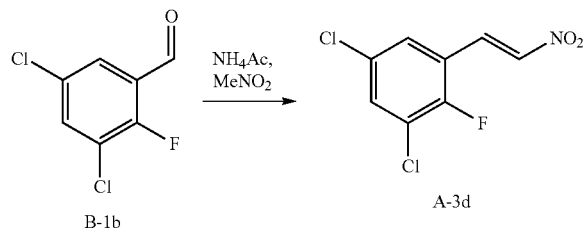

3,5-Dichloro-2-fluoro-benzaldehyde (500 mg, 0.003 mol) is dissolved in acetic acid (10 mL), then ammonium acetate (598 mg, 0.008 mol) and nitromethane (0.382 mL, 0.008 mol) is added and the resulting reaction mixture is heated to 110° C. and stirred for 6 h. The reaction mixture is cooled to rt and quenched with water. The precipitated solid is filtered and dried. The obtained crude compound is purified via column chromatography to give compound A-3d.

The following intermediates A-3 (table 4) are available in an analogous manner starting from different aldehydes B-1.

TABLE 4

| # | structure | $t_{ret}$ [min] | $[M + H]^+$ | HPLC method |
|---|---|---|---|---|
| A-3d | Cl, Cl, F, NO₂ structure | n.a. | n.a. | |
| A-3e | Br, F, NO₂ structure | 1.27 | n.a. | A |
| A-3f | F, F, Cl, NO₂ structure | 0.70 | n.a. | E |

TABLE 4-continued

| # | structure | $t_{ret}$ [min] | $[M + H]^+$ | HPLC method |
|---|---|---|---|---|
| A-3g | Cl, F, NO₂ structure | n.a. | n.a. | n.a. |

Synthesis of Intermediate A-4 (Method A)

Experimental Procedure for the Synthesis of A-4a

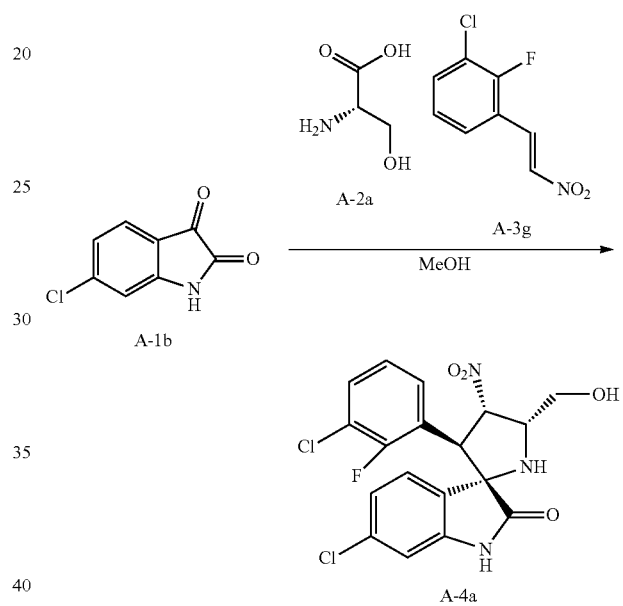

6-Chloroisatin A-1b (1.00 g, 5.4 mmol), 1-chloro-2-fluoro-3-[(E)-2-nitro-vinyl]benzene](1.1 g, 5.4 mmol) A-3g and L-serine A-2a (0.57 g, 5.4 mmol) are refluxed in MeOH for 16 h. The reaction mixture is concentrated in vacuo and purified by chromatography or crystallization if necessary.

The following intermediates A-4 (table 5) are available in an analogous manner starting from different annulated 1H-pyrrole-2,3-diones A-1, amino acids A-2 and nitroethenes A-3.

TABLE 5

| # | structure | $t_{ret}$ [min] | $[M + H]^+$ | HPLC method |
|---|---|---|---|---|
| A-4a | (spirooxindole structure) | 1.17 | 426 | A |

TABLE 5-continued

| # | structure | $t_{ret}$ [min] | $[M+H]^+$ | HPLC method |
|---|---|---|---|---|
| A-4b | 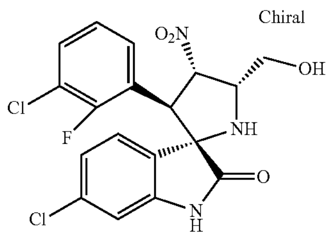 [SMILES: O=C1Nc2cc(Cl)ccc2[C@]12N[C@@H](CO)[C@@H]([N+](=O)[O-])[C@@H]2c1cccc(Cl)c1F] | 1.17 | 426 | A |
| A-4c | 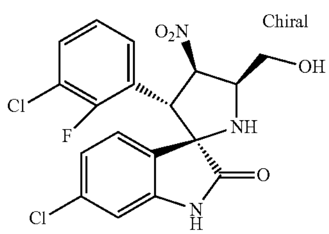 [SMILES: O=C1Nc2cc(Cl)ccc2[C@@]12N[C@H](CO)[C@H]([N+](=O)[O-])[C@H]2c1cccc(Cl)c1F] | 1.17 | 426 | A |
| A-4d | 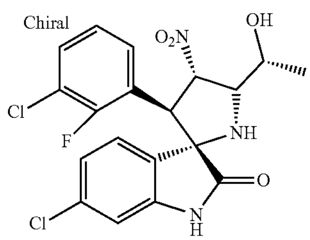 | 0.64 | 440 | G |
| A-4e | 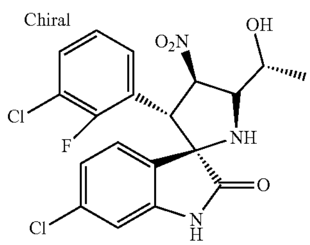 | 0.60 | 440 | G |
| A-4f | 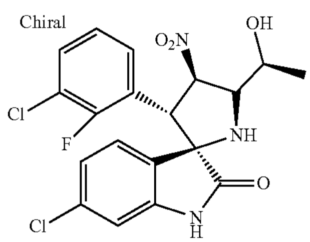 | 0.60 | 440 | G |
| A-4g | 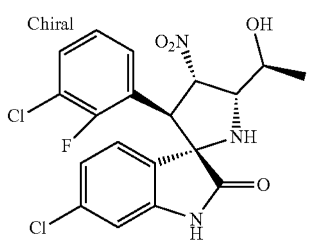 [SMILES: C[C@H](O)[C@@H]1N[C@@]2(C(=O)Nc3cc(Cl)ccc32)[C@@H](c2cccc(Cl)c2F)[C@@H]1[N+](=O)[O-]] | 0.64 | 440 | G |

TABLE 5-continued

| # | structure | $t_{ret}$ [min] | [M + H]⁺ | HPLC method |
|---|---|---|---|---|
| A-4h | 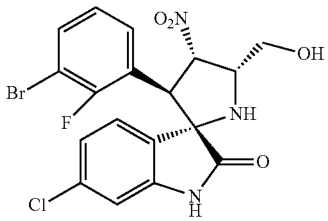 [SMILES: O=C1Nc2cc(Cl)ccc2[C@]12N[C@@H](CO)[C@@H]([N+](=O)[O-])[C@@H]2c1cccc(Br)c1F] | 2.24 | 472 | L |
| A-4i | 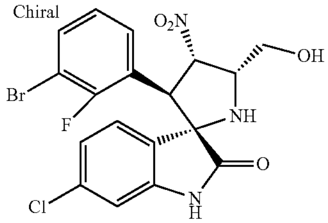 [SMILES: O=C1Nc2cc(Cl)ccc2[C@]12N[C@@H](CO)[C@@H]([N+](=O)[O-])[C@@H]2c1cccc(Br)c1F] | 2.24 | 472 | L |
| A-4j | 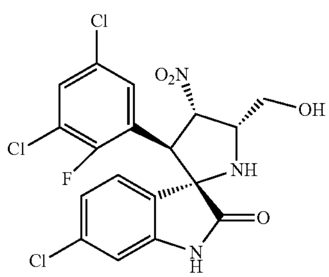 [SMILES: O=C1Nc2cc(Cl)ccc2[C@]12N[C@@H](CO)[C@@H]([N+](=O)[O-])[C@@H]2c1cc(Cl)cc(Cl)c1F] | 2.40 | 460/462 | L |
| A-4k | 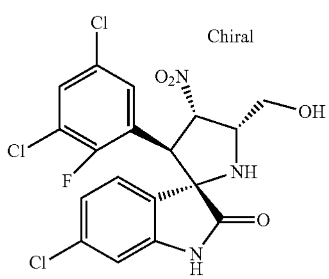 [SMILES: O=C1Nc2cc(Cl)ccc2[C@]12N[C@@H](CO)[C@@H]([N+](=O)[O-])[C@@H]2c1cc(Cl)cc(Cl)c1F] | 2.40 | 460/462 | L |
| A-4l | 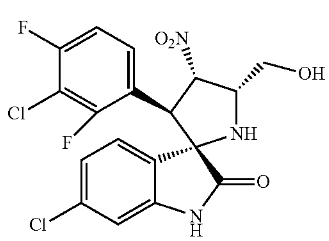 [SMILES: O=C1Nc2cc(Cl)ccc2[C@]12N[C@@H](CO)[C@@H]([N+](=O)[O-])[C@@H]2c1ccc(F)c(Cl)c1F] | 1.19 | 444 | A |
| A-4m | 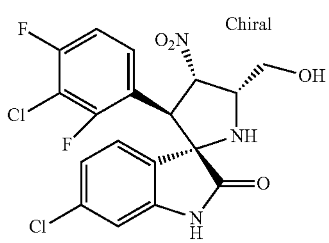 [SMILES: O=C1Nc2cc(Cl)ccc2[C@]12N[C@@H](CO)[C@@H]([N+](=O)[O-])[C@@H]2c1ccc(F)c(Cl)c1F] | 1.19 | 444 | A |

TABLE 5-continued

| # | structure | $t_{ret}$ [min] | $[M + H]^+$ | HPLC method |
|---|---|---|---|---|
| A-4n | 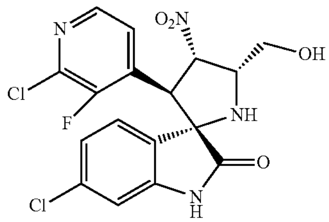 | 1.06 | 425 | A |
| A-4o | Chiral | 1.06 | 425 | A |
| A-4p | 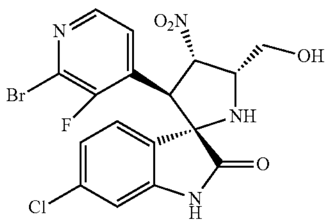 [SMILES: O=C1Nc2cc(Cl)ccc2[C@]12N[C@@H](CO)[C@@H]([N+](=O)[O-])[C@@H]2c1ccnc(Cl)c1F] | 1.07 | 471 | A |
| A-4q | Chiral | 1.07 | 471 | A |
| A-4r | 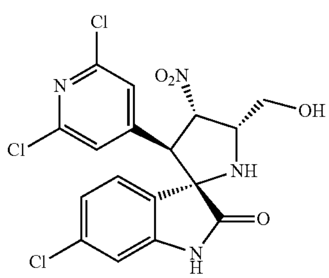 [SMILES: O=C1Nc2cc(Cl)ccc2[C@]12N[C@@H](CO)[C@@H]([N+](=O)[O-])[C@@H]2c1cc(Cl)nc(Cl)c1] | 1.14 | 443 | A |
| A-4s | Chiral | 1.14 | 443 | A |

TABLE 5-continued

| # | structure | $t_{ret}$ [min] | [M + H]$^+$ | HPLC method |
|---|---|---|---|---|
| A-4t | 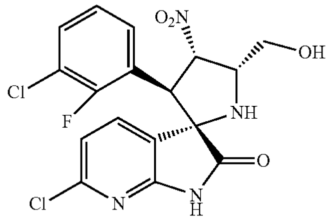 [SMILES: O=C1Nc2nc(Cl)ccc2[C@]12N[C@@H](CO)[C@@H]([N+](=O)[O-])[C@@H]2c1cccc(Cl)c1F] | 1.10 | 427 | A |
| A-4u | Chiral | 1.10 | 427 | A |
| A-4v | 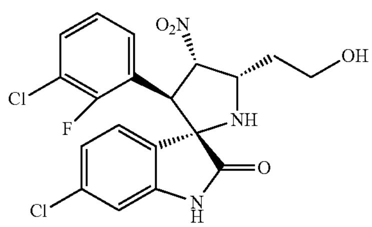 [SMILES: O=C1Nc2cc(Cl)ccc2[C@]12N[C@@H](CCO)[C@@H]([N+](=O)[O-])[C@@H]2c1cccc(Cl)c1F] | 1.21 | 440 | A |
| A-4w | Chiral | 1.21 | 440 | A |

Alternatively, intermediates A-4, e.g. A-4a, can also be obtained with some modifications to the procedure as described and depicted hereinbefore:

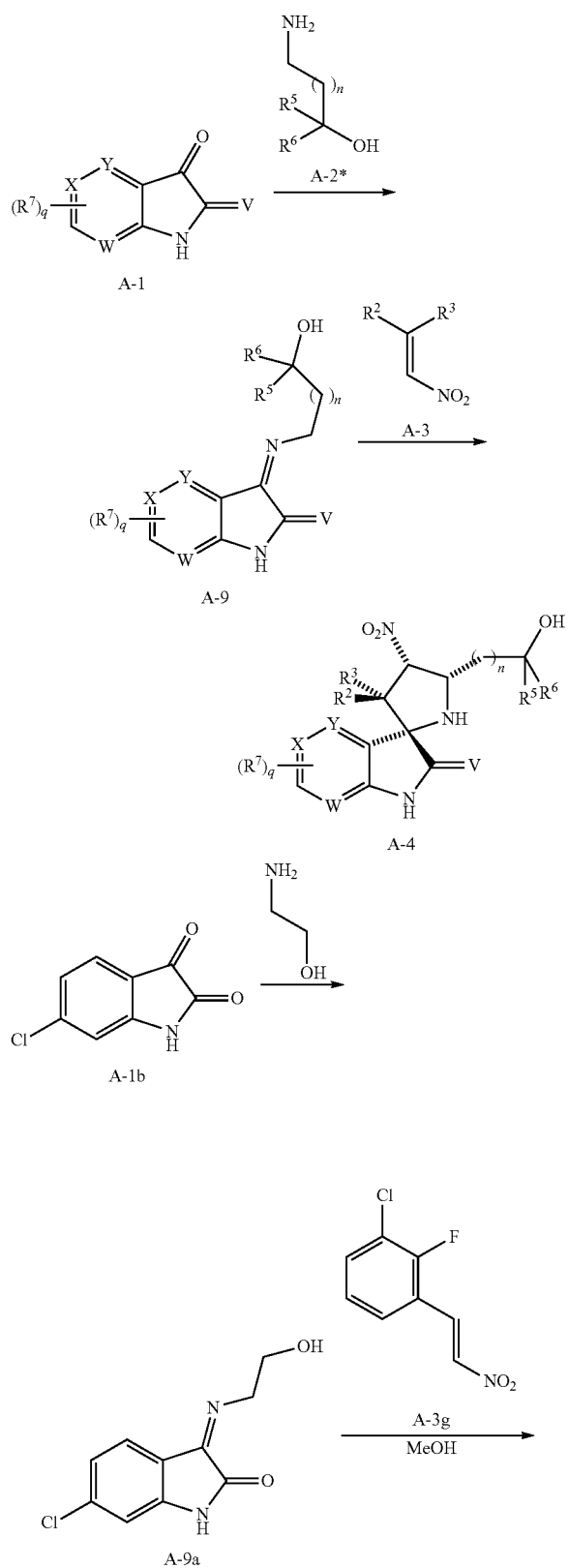

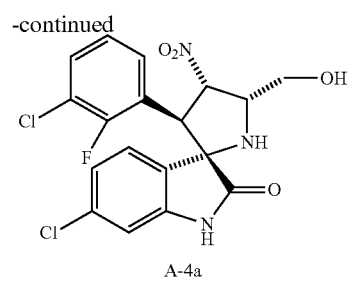

In this alternative, isatin derivative A-1, e.g. A-1b, is reacted with an amino alcohol A-2*, e.g. 2-aminoethanol, in an appropriate solvent, e.g. MeOH, ACN, DCM, THF or mixtures thereof (ACN being preferred), to form the imine intermediate A-9, e.g. A-9a. Preferably, imine formation is performed in the presence of an acid, e.g. AcOH or pTsOH (pTsOH being most preferred). A-9 (A-9a) can optionally be isolated and purified or is directly reacted with nitro alkenes A-3, e.g. A-3g, in the cycloaddition, preferably with addition of a base (most preferred is N-methylpyrrolidine) to yield intermediates A-4, e.g. A-4a. Possible solvents for the cycloaddition step are MeTHF, water, MeOH, dioxane, THF, DME and mixtures thereof. Especially preferred are mixtures with water, most preferred is MeTHF/water.

Thus, a further aspect of the invention is a method for synthesizing intermediates A-4, preferably A-4a, comprising reacting a compound A-1, preferably A-1b, with an amino alcohol A-2*, preferably 2-aminoethanol, in an appropriate solvent, preferably selected from among MeOH, ACN, DCM, THF or mixtures thereof, to obtain the corresponding imine intermediate A-9, preferably A-9a. In a further aspect the method further comprises reacting the imine intermediate A-9, preferably A-9a, with nitro alkene A-3, preferably A-3g, preferably with addition of a base (most preferred is N-methylpyrrolidine).

Synthesis of Intermediate A-5 (Method B)

Experimental Procedure for the Synthesis of A-5a

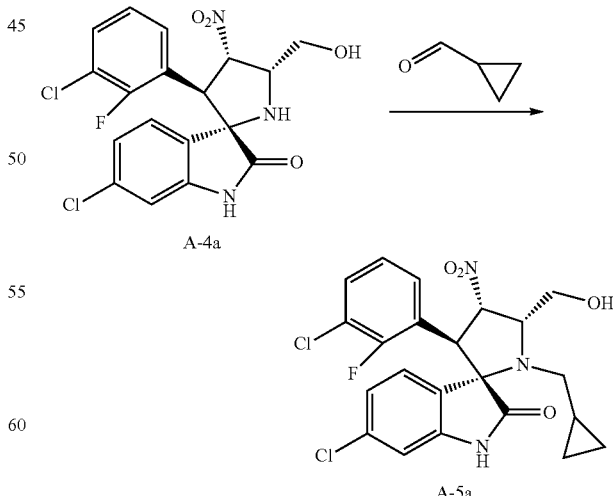

To a solution of intermediate A-4a (1.27 g, 2.97 mmol) in DMF (1.3 mL) is added cyclopropanecarbaldehyde (0.43 g, 5.94 mmol) and AcOH (0.34 mL, 5.94 mmol) and the reaction mixture is stirred for 15 min. Sodium triacetoxyborohydride (1.89 g, 8.90 mmol) is slowly added and the mixture is stirred overnight. Water is added to the reaction mixture and it is extracted with DCM. The solvents are removed under reduced pressure and the residue is dissolved in diethylether and washed with saturated sodium hydrogencarbonate solution. The combined organic layer is dried (MgSO₄), filtered, concentrated in vacuo and the crude product A-5a is purified by chromatography if necessary.

The following intermediates A-5 (table 6) are available in an analogous manner starting from different intermediates A-4.

TABLE 6

| # | structure | $t_{ret}$ [min] | [M + H]⁺ | HPLC method |
|---|---|---|---|---|
| A-5a | 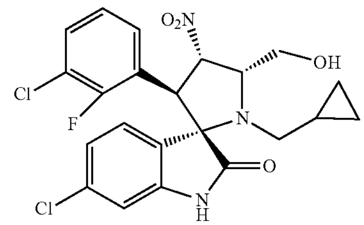 [SMILES: O=C1Nc2cc(Cl)ccc2[C@@]12[C@@H](c1cccc(Cl)c1F)[C@H]([N+](=O)[O-])[C@H](CO)N2CC1CC1] | 1.36 | 480 | A |
| A-5b | 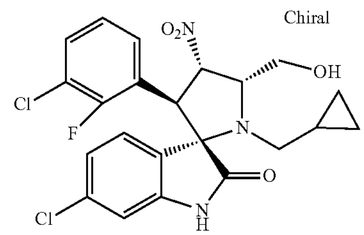 [SMILES: O=C1Nc2cc(Cl)ccc2[C@@]12[C@@H](c1cccc(Cl)c1F)[C@H]([N+](=O)[O-])[C@H](CO)N2CC1CC1] | 1.36 | 480 | A |
| A-5c | 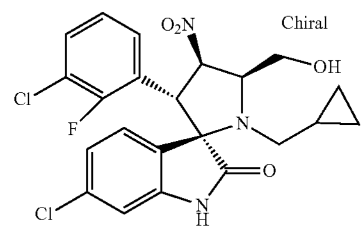 [SMILES: O=C1Nc2cc(Cl)ccc2[C@]12[C@H](c1cccc(Cl)c1F)[C@@H]([N+](=O)[O-])[C@@H](CO)N2CC1CC1] | 1.36 | 480 | A |
| A-5d | 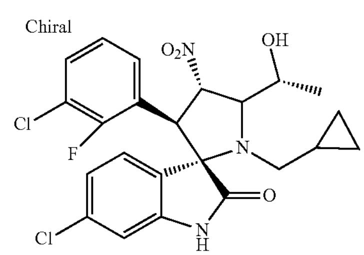 [SMILES: C[C@@H](O)C1[C@@H]([N+](=O)[O-])[C@H](c2cccc(Cl)c2F)[C@]2(C(=O)Nc3cc(Cl)ccc32)N1CC1CC1] | 0.73 | 494 | G |
| A-5e | 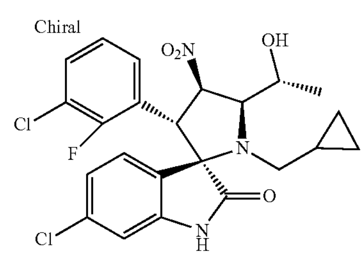 [SMILES: C[C@@H](O)[C@@H]1[C@H]([N+](=O)[O-])[C@@H](c2cccc(Cl)c2F)[C@@]2(C(=O)Nc3cc(Cl)ccc32)N1CC1CC1] | 0.76 | 494 | G |

TABLE 6-continued

| # | structure | $t_{ret}$ [min] | $[M + H]^+$ | HPLC method |
|---|---|---|---|---|
| A-5f | 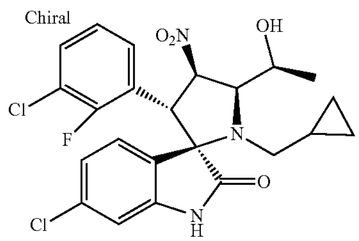 [SMILES: C[C@H](O)[C@@H]1[C@H]([N+](=O)[O-])[C@@H](c2cccc(Cl)c2F)[C@@]2(C(=O)Nc3cc(Cl)ccc32)N1CC1CC1] | 0.78 | 494 | G |
| A-5g | 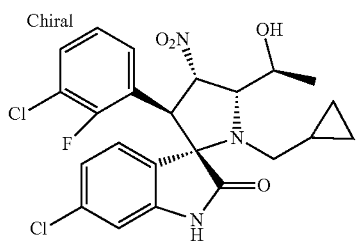 [SMILES: C[C@H](O)[C@H]1[C@@H]([N+](=O)[O-])[C@H](c2cccc(Cl)c2F)[C@]2(C(=O)Nc3cc(Cl)ccc32)N1CC1CC1] | 0.75 | 494 | G |
| A-5h | 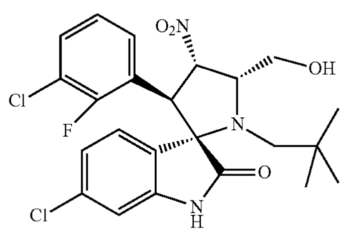 [SMILES: CC(C)(C)CN1[C@@H](CO)[C@@H]([N+](=O)[O-])[C@H](c2cccc(Cl)c2F)[C@]12C(=O)Nc1cc(Cl)ccc12] | 0.83 | 496 | E |
| A-5i | 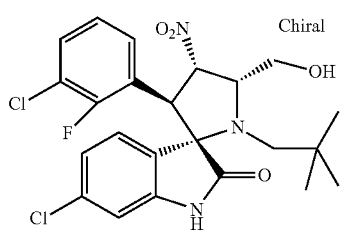 [SMILES: CC(C)(C)CN1[C@@H](CO)[C@@H]([N+](=O)[O-])[C@H](c2cccc(Cl)c2F)[C@]12C(=O)Nc1cc(Cl)ccc12] | 0.83 | 496 | E |
| A-5j | 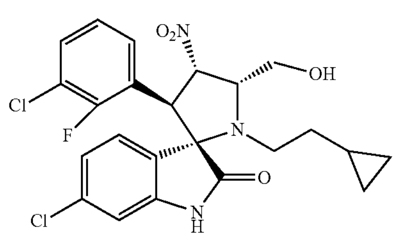 [SMILES: O=C1Nc2cc(Cl)ccc2[C@@]12[C@@H](c1cccc(Cl)c1F)[C@H]([N+](=O)[O-])[C@H](CO)N2CCC1CC1] | 0.81 | 494 | E |
| A-5k | 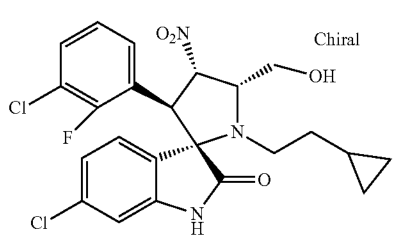 [SMILES: O=C1Nc2cc(Cl)ccc2[C@@]12[C@@H](c1cccc(Cl)c1F)[C@H]([N+](=O)[O-])[C@H](CO)N2CCC1CC1] | 0.81 | 494 | E |

TABLE 6-continued

| # | structure | $t_{ret}$ [min] | [M + H]$^+$ | HPLC method |
|---|---|---|---|---|
| A-5l | 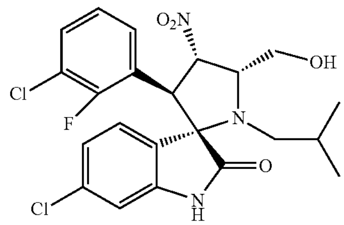 [SMILES: CC(C)CN1[C@@H](CO)[C@@H]([N+](=O)[O-])[C@H](c2cccc(Cl)c2F)[C@]12C(=O)Nc1cc(Cl)ccc12] | 0.82 | 482 | E |
| A-5m | Chiral | 0.82 | 482 | E |
| A-5n | Chiral | 0.82 | 482 | E |
| A-5o | 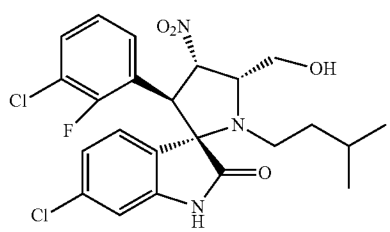 [SMILES: CC(C)CCN1[C@@H](CO)[C@@H]([N+](=O)[O-])[C@H](c2cccc(Cl)c2F)[C@]12C(=O)Nc1cc(Cl)ccc12] | 0.85 | 496 | B |
| A-5p | Chiral | 0.85 | 496 | B |
| A-5q | 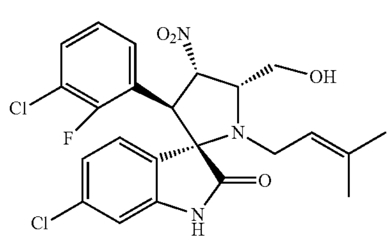 [SMILES: CC(C)=CCN1[C@@H](CO)[C@@H]([N+](=O)[O-])[C@H](c2cccc(Cl)c2F)[C@]12C(=O)Nc1cc(Cl)ccc12] | 1.39 | 494 | A |

TABLE 6-continued

| # | structure | $t_{ret}$ [min] | [M + H]$^+$ | HPLC method |
|---|---|---|---|---|
| A-5r | 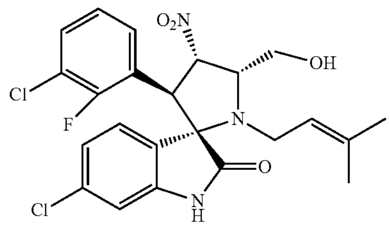 [SMILES: CC(C)=CCN1[C@@H](CO)[C@@H]([N+](=O)[O-])[C@H](c2cccc(Cl)c2F)[C@]12C(=O)Nc1cc(Cl)ccc12] | 1.39 | 494 | A |
| A-5s | 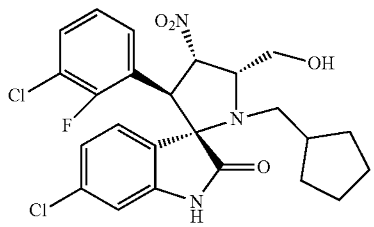 [SMILES: O=C1Nc2cc(Cl)ccc2[C@@]12[C@@H](c1cccc(Cl)c1F)[C@H]([N+](=O)[O-])[C@H](CO)N2CC1CCOC1] | 0.86 | 508 | E |
| A-5t | Chiral | 0.86 | 508 | E |
| A-5u | 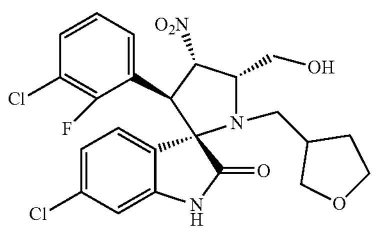 | 0.69 | 510 | E |
| A-5v | Chiral | 0.69 | 510 | E |
| A-5w | 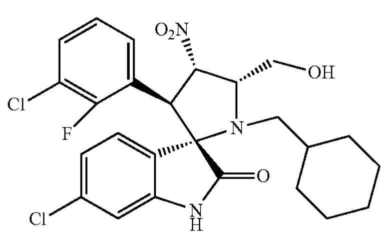 [SMILES: O=C1Nc2cc(Cl)ccc2[C@@]12[C@@H](c1cccc(Cl)c1F)[C@H]([N+](=O)[O-])[C@H](CO)N2CC1CCCCC1] | 0.90 | 522 | E |

TABLE 6-continued

| # | structure | $t_{ret}$ [min] | $[M + H]^+$ | HPLC method |
|---|---|---|---|---|
| A-5x | Chiral | 0.90 | 522 | E |
| A-5y | 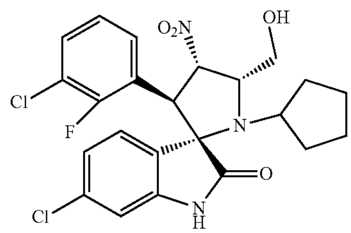 [SMILES: O=C1Nc2cc(Cl)ccc2[C@@]12[C@@H](c1cccc(Cl)c1F)[C@H]([N+](=O)[O-])[C@H](CO)N2C1CCCC1] | 1.39 | 494 | A |
| A-5z | Chiral | 1.39 | 494 | A |
| A-5aa | 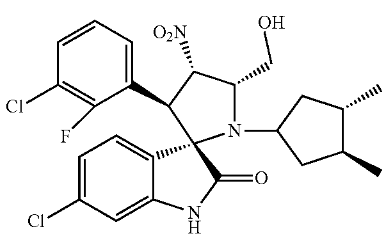 [SMILES: C[C@H]1CC(N2[C@@H](CO)[C@@H]([N+](=O)[O-])[C@H](c3cccc(Cl)c3F)[C@]23C(=O)Nc2cc(Cl)ccc23)C[C@@H]1C] | 0.87 | 522 | E |
| A-5ab | Chiral | 0.87 | 522 | E |
| A-5ac | 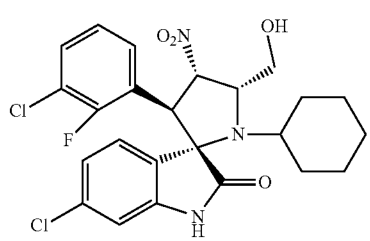 [SMILES: O=C1Nc2cc(Cl)ccc2[C@@]12[C@@H](c1cccc(Cl)c1F)[C@H]([N+](=O)[O-])[C@H](CO)N2C1CCCCC1] | 0.83 | 508 | E |

TABLE 6-continued

| # | structure | $t_{ret}$ [min] | [M + H]$^+$ | HPLC method |
|---|---|---|---|---|
| A-5ad | 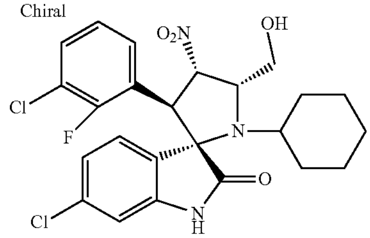 [SMILES: O=C1Nc2cc(Cl)ccc2[C@@]12[C@@H](c1cccc(Cl)c1F)[C@H]([N+](=O)[O-])[C@H](CO)N2C1CCCCC1] | 0.83 | 508 | E |
| A-5ae | 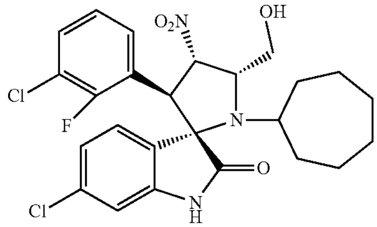 [SMILES: O=C1Nc2cc(Cl)ccc2[C@@]12[C@@H](c1cccc(Cl)c1F)[C@H]([N+](=O)[O-])[C@H](CO)N2C1CCCCCC1] | 1.47 | 522 | A |
| A-5af | 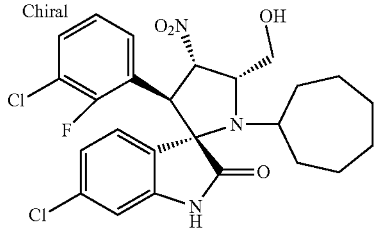 [SMILES: O=C1Nc2cc(Cl)ccc2[C@@]12[C@@H](c1cccc(Cl)c1F)[C@H]([N+](=O)[O-])[C@H](CO)N2C1CCCCCC1] | 1.47 | 522 | A |
| A-5ag | 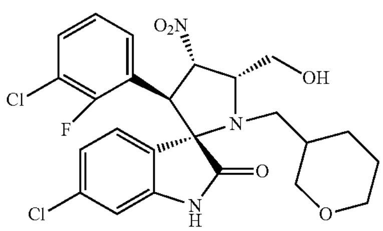 | 0.73 | 524 | E |
| A-5ah | 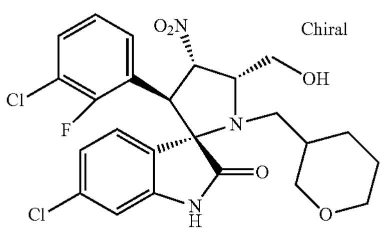 | 0.73 | 524 | E |
| A-5ai | 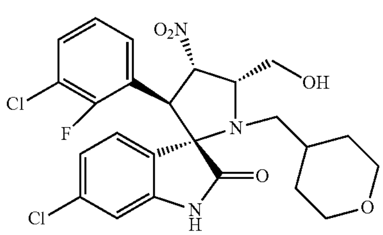 [SMILES: O=C1Nc2cc(Cl)ccc2[C@@]12[C@@H](c1cccc(Cl)c1F)[C@H]([N+](=O)[O-])[C@H](CO)N2CC1CCOCC1] | 0.71 | 524 | E |

TABLE 6-continued

| # | structure | $t_{ret}$ [min] | [M + H]⁺ | HPLC method |
|---|---|---|---|---|
| A-5aj | Chiral | 0.71 | 524 | E |
| A-5ak | 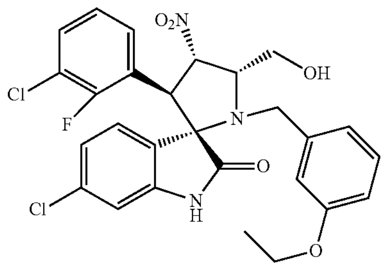 [SMILES: CCOc1cccc(CN2[C@@H](CO)[C@@H]([N+](=O)[O-])[C@H](c3cccc(Cl)c3F)[C@]23C(=O)Nc2cc(Cl)ccc23)c1] | 1.47 | 560 | A |
| A-5al | Chiral | 1.47 | 560 | A |
| A-5am | 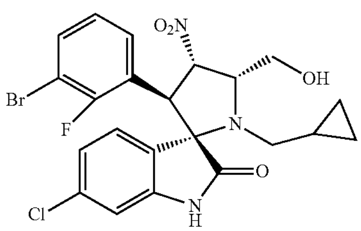 | 2.58 | 526 | L |
| A-5an | Chiral | 2.58 | 526 | L |
| A-5ao | 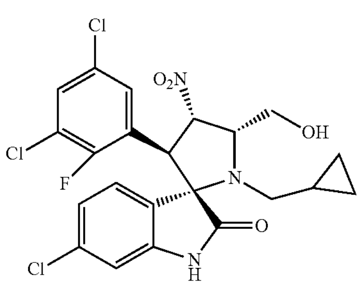 [SMILES: O=C1Nc2cc(Cl)ccc2[C@@]12[C@@H](c1cc(Cl)cc(Cl)c1F)[C@H]([N+](=O)[O-])[C@H](CO)N2CC1CC1] | 2.70 | 514/516 | L |

TABLE 6-continued
| # | structure | $t_{ret}$ [min] | $[M + H]^+$ | HPLC method |
|---|---|---|---|---|
| A-5ap | 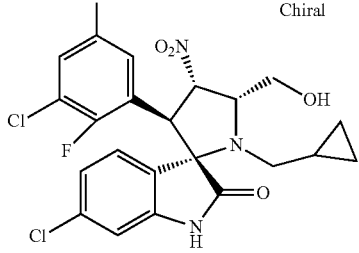 | 2.70 | 514/516 | L |
| A-5aq | 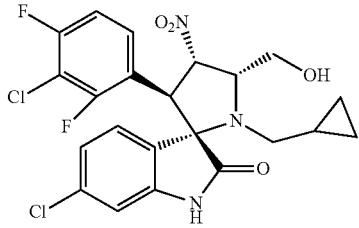 [SMILES: O=C1Nc2cc(Cl)ccc2[C@@]12[C@@H](c1ccc(F)c(Cl)c1F)[C@H]([N+](=O)[O-])[C@H](CO)N2CC1CC1] | 0.79 | 498 | E |
| A-5ar | 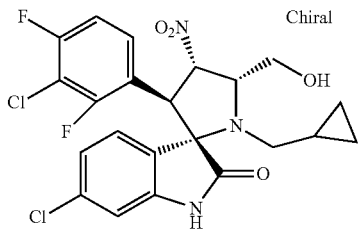 [SMILES: O=C1Nc2cc(Cl)ccc2[C@@]12[C@@H](c1ccc(F)c(Cl)c1F)[C@H]([N+](=O)[O-])[C@H](CO)N2CC1CC1] | 0.79 | 498 | E |
| A-5as | 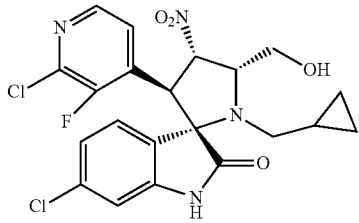 | 0.71 | 481 | E |
| A-5at | 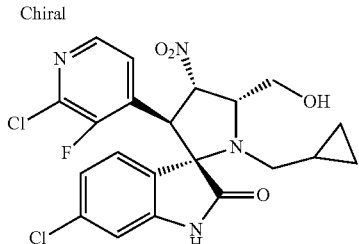 | 0.71 | 481 | E |
| A-5au | 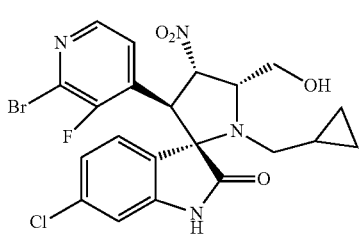 [SMILES: O=C1Nc2cc(Cl)ccc2[C@@]12[C@@H](c1ccnc(Cl)c1F)[C@H]([N+](=O)[O-])[C@H](CO)N2CC1CC1] | 0.71 | 525/527 | E |

TABLE 6-continued

| # | structure | $t_{ret}$ [min] | [M + H]$^+$ | HPLC method |
|---|---|---|---|---|
| A-5av | 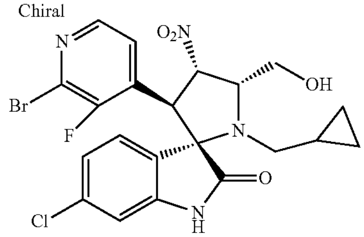 [SMILES: O=C1Nc2cc(Cl)ccc2[C@@]12[C@@H](c1ccnc(Br)c1F)[C@H]([N+](=O)[O-])[C@H](CO)N2CC1CC1] | 0.71 | 525/527 | E |
| A-5aw | 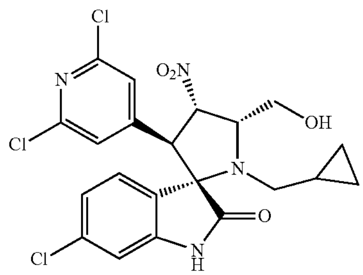 [SMILES: O=C1Nc2cc(Cl)ccc2[C@@]12[C@@H](c1cc(Cl)nc(Cl)c1)[C@H]([N+](=O)[O-])[C@H](CO)N2CC1CC1] | 0.75 | 497/498 | E |
| A-5ax | 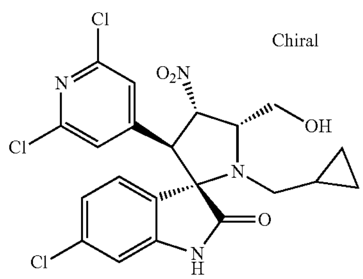 [SMILES: O=C1Nc2cc(Cl)ccc2[C@@]12[C@@H](c1cc(Cl)nc(Cl)c1)[C@H]([N+](=O)[O-])[C@H](CO)N2CC1CC1] | 0.75 | 497/498 | E |
| A-5ay | 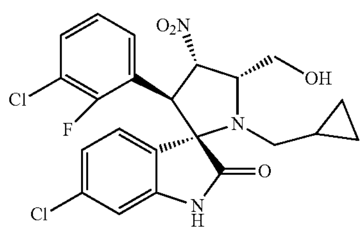 [SMILES: O=C1Nc2cc(Cl)ccc2[C@@]12[C@@H](c1cccc(Cl)c1F)[C@H]([N+](=O)[O-])[C@H](CO)N2CC1CC1] | 0.72 | 481 | E |
| A-5az | 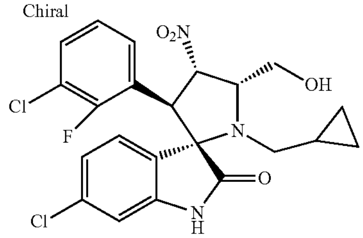 [SMILES: O=C1Nc2cc(Cl)ccc2[C@@]12[C@@H](c1cccc(Cl)c1F)[C@H]([N+](=O)[O-])[C@H](CO)N2CC1CC1] | 0.72 | 481 | E |
| A-5ba | 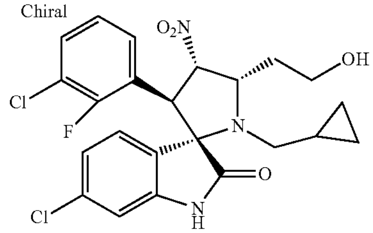 [SMILES: O=C1Nc2cc(Cl)ccc2[C@@]12[C@@H](c1cccc(Cl)c1F)[C@H]([N+](=O)[O-])[C@H](CCO)N2CC1CC1] | 0.79 | 494 | E |

Synthesis of Intermediate A-6 (Method C)

Experimental Procedure for the Synthesis of A-6a

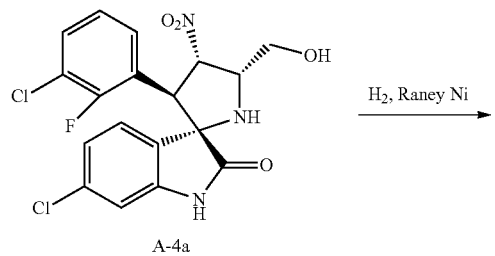

A-4a

Intermediate A-4a (0.2 g, 0.47 mmol) is dissolved in MeOH (4 mL) and DCM (1 mL) and treated with a catalytic amount of RANEY nickel. The reaction vessel is pressurized with hydrogen (6 bar) and the reaction mixture stirred for 16 h. Solids are removed by filtration and the solvent of the filtrate removed under reduced pressure. The residue is redissolved in EtOAc and water and treated with diluted aqueous HCl. The aqueous layer is extracted with EtOAc, the combined organic layers are dried with sodium sulfate and the solvent is evaporated to yield A-6a which is purified by chromatography if necessary.

The following intermediates A-6 (table 7) are available in an analogous manner starting from different intermediates A-4.

TABLE 7

| # | structure | $t_{ret}$ [min] | [M + H]$^+$ | HPLC method |
|---|---|---|---|---|
| A-6a | 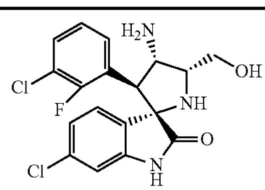 | 0.50 | 396 | E |
| A-6b | Chiral | 0.50 | 396 | E |

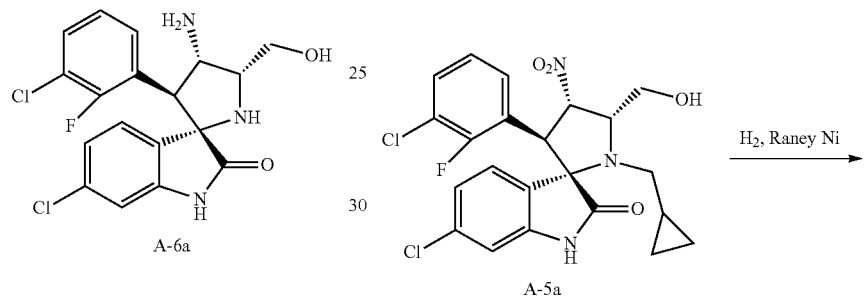

Synthesis of Intermediate A-6 (Method D)

Experimental Procedure for the Synthesis of A-6c

A-5a

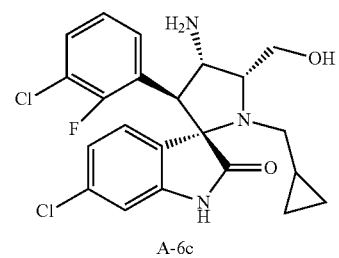

A-6c

Intermediate A-5a (1.4 g, 2.91 mmol) is dissolved in MeOH (25 mL) and DCM (16 mL) and treated with a catalytic amount of RANEY nickel. The reaction vessel is pressurized with hydrogen (6 bar) and the reaction mixture stirred for 16 h. Solids are removed by filtration and the solvent of the filtrate removed under reduced pressure. The residue is redissolved in EtOAc and water and treated with diluted aqueous HCl. The aqueous layer is extracted with EtOAc, the combined organic layers are dried with sodium sulfate and the solvent is evaporated to yield A-6c which is purified by chromatography if necessary.

The following intermediates A-6 (table 8) are available in an analogous manner starting from different intermediates A-5.

TABLE 8

| # | structure | t_ret [min] | [M + H]+ | HPLC method |
|---|---|---|---|---|
| A-6c | 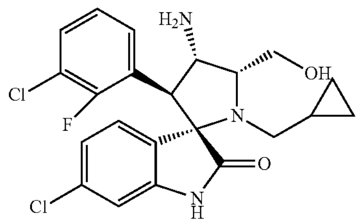 [SMILES: N[C@@H]1[C@H](CO)N(CC2CC2)[C@@]2(C(=O)Nc3cc(Cl)ccc32)[C@H]1c1cccc(Cl)c1F] | 1.22 | 480 | A |
| A-6d | Chiral | 1.22 | 480 | A |
| A-6e | Chiral | 1.22 | 480 | A |
| A-6f | Chiral | 0.53 | 464 | G |
| A-6g | Chiral | 0.50 | 464 | G |
| A-6h | Chiral | 0.53 | 464 | G |

TABLE 8-continued

| # | structure | | $t_{ret}$ [min] | $[M + H]^+$ | HPLC method |
|---|---|---|---|---|---|
| A-6i | Chiral | | 0.49 | 464 | G |
| A-6j | 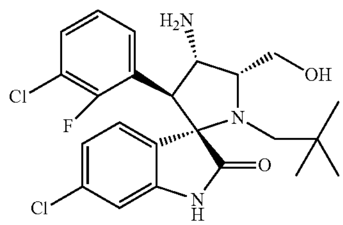 [SMILES: CC(C)(C)CN1[C@@H](CO)[C@@H](N)[C@H](c2cccc(Cl)c2F)[C@]12C(=O)Nc1cc(Cl)ccc12] | | 0.61 | 466 | E |
| A-6k | Chiral | | 0.61 | 466 | E |
| A-6l | 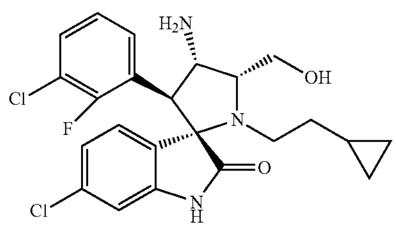 [SMILES: N[C@@H]1[C@H](CO)N(CCC2CC2)[C@@]2(C(=O)Nc3cc(Cl)ccc32)[C@H]1c1cccc(Cl)c1F] | | 0.71 | 464 | E |
| A-6m | Chiral | | 0.71 | 464 | E |
| A-6n | Chiral | | 0.71 | 464 | E |

TABLE 8-continued

| # | structure | | $t_{ret}$ [min] | $[M + H]^+$ | HPLC method |
|---|---|---|---|---|---|
| A-6o | 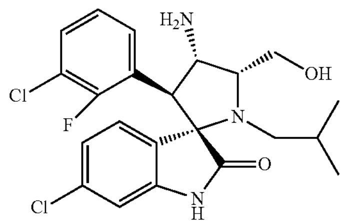 [SMILES: CC(C)CN1[C@@H](CO)[C@@H](N)[C@H](c2cccc(Cl)c2F)[C@]12C(=O)Nc1cc(Cl)ccc12] | | 0.72 | 452 | E |
| A-6p | 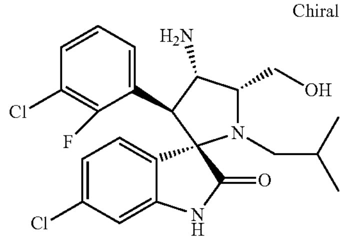 [SMILES: CC(C)CN1[C@@H](CO)[C@@H](N)[C@H](c2cccc(Cl)c2F)[C@]12C(=O)Nc1cc(Cl)ccc12] | Chiral | 0.72 | 452 | E |
| A-6q | 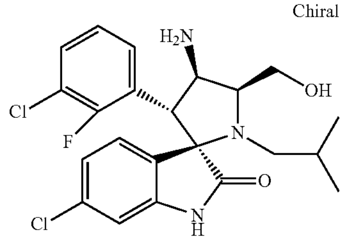 [SMILES: CC(C)CN1[C@H](CO)[C@H](N)[C@@H](c2cccc(Cl)c2F)[C@@]12C(=O)Nc1cc(Cl)ccc12] | Chiral | 0.72 | 452 | E |
| A-6r | 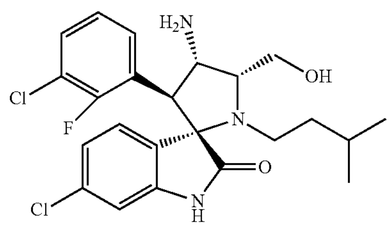 [SMILES: CC(C)CCN1[C@@H](CO)[C@@H](N)[C@H](c2cccc(Cl)c2F)[C@]12C(=O)Nc1cc(Cl)ccc12] | | 0.76 | 466 | B |
| A-6s | 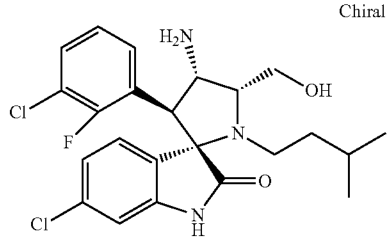 [SMILES: CC(C)CCN1[C@@H](CO)[C@@H](N)[C@H](c2cccc(Cl)c2F)[C@]12C(=O)Nc1cc(Cl)ccc12] | Chiral | 0.76 | 466 | B |
| A-6t | 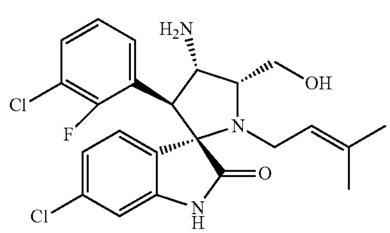 [SMILES: CC(C)=CCN1[C@@H](CO)[C@@H](N)[C@H](c2cccc(Cl)c2F)[C@]12C(=O)Nc1cc(Cl)ccc12] | | 1.25 | 464 | A |

TABLE 8-continued

| # | structure | | $t_{ret}$ [min] | [M + H]+ | HPLC method |
|---|---|---|---|---|---|
| A-6u | 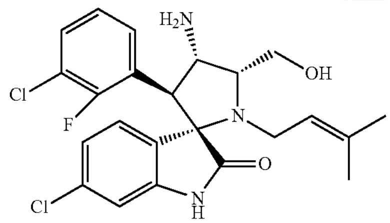 | Chiral | 1.25 | 464 | A |
| A-6v | 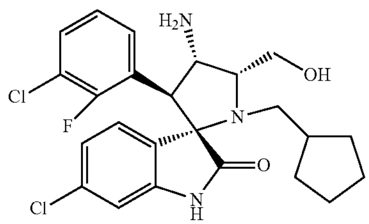 [SMILES: N[C@@H]1[C@H](CO)N(CC2CCCC2)[C@@]2(C(=O)Nc3cc(Cl)ccc32)[C@H]1c1cccc(Cl)c1F] | | 0.77 | 478 | E |
| A-6w | 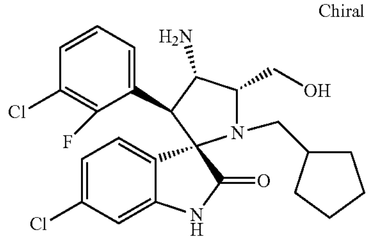 [SMILES: N[C@@H]1[C@H](CO)N(CC2CCCC2)[C@@]2(C(=O)Nc3cc(Cl)ccc32)[C@H]1c1cccc(Cl)c1F] | Chiral | 0.77 | 478 | E |
| A-6x | 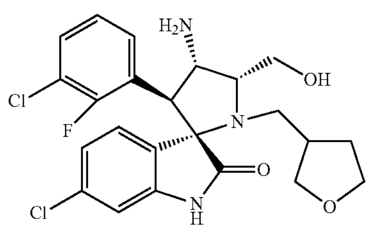 [SMILES: N[C@@H]1[C@H](CO)N(CC2CCOC2)[C@@]2(C(=O)Nc3cc(Cl)ccc32)[C@H]1c1cccc(Cl)c1F] | | 0.56 | 480 | E |
| A-6y | 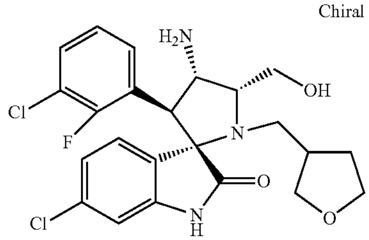 [SMILES: N[C@@H]1[C@H](CO)N(CC2CCOC2)[C@@]2(C(=O)Nc3cc(Cl)ccc32)[C@H]1c1cccc(Cl)c1F] | Chiral | 0.56 | 480 | E |
| A-6z | 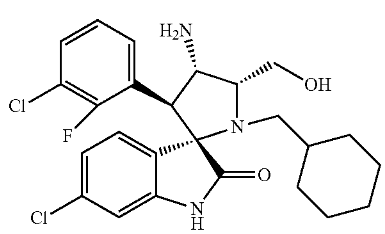 [SMILES: N[C@@H]1[C@H](CO)N(CC2CCCCC2)[C@@]2(C(=O)Nc3cc(Cl)ccc32)[C@H]1c1cccc(Cl)c1F] | | 0.82 | 492 | E |

TABLE 8-continued

| # | structure | | $t_{ret}$ [min] | $[M + H]^+$ | HPLC method |
|---|---|---|---|---|---|
| A-6aa | 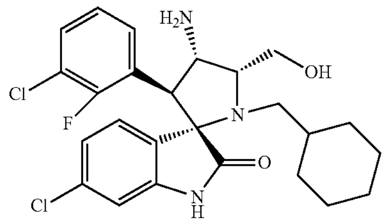 | Chiral | 0.82 | 492 | E |
| A-6ab | 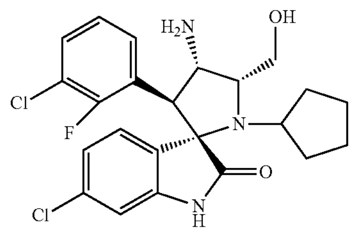 [SMILES: N[C@@H]1[C@H](CO)N(C2CCCC2)[C@@]2(C(=O)Nc3cc(Cl)ccc32)[C@H]1c1cccc(Cl)c1F] | | 1.24 | 464 | A |
| A-6ac | Chiral | | 1.24 | 464 | A |
| A-6ad | 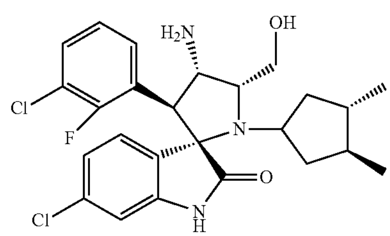 [SMILES: C[C@H]1CC(N2[C@@H](CO)[C@@H](N)[C@H](c3cccc(Cl)c3F)[C@]23C(=O)Nc2cc(Cl)ccc23)C[C@@H]1C] | | 0.78 | 492 | E |
| A-6ae | Chiral | | 0.78 | 492 | E |
| A-6af | 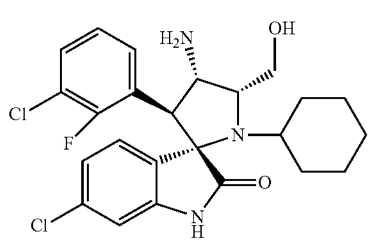 [SMILES: N[C@@H]1[C@H](CO)N(C2CCCCC2)[C@@]2(C(=O)Nc3cc(Cl)ccc32)[C@H]1c1cccc(Cl)c1F] | | 0.74 | 479 | E |

TABLE 8-continued

| # | structure | | $t_{ret}$ [min] | [M + H]+ | HPLC method |
|---|---|---|---|---|---|
| A-6ag | Chiral | | 0.74 | 479 | E |
| A-6ah | 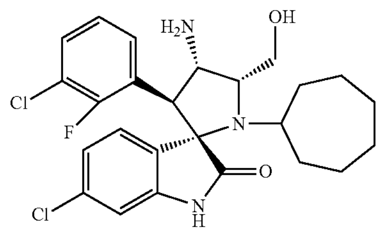 [SMILES: N[C@@H]1[C@H](CO)N(C2CCCCCC2)[C@@]2(C(=O)Nc3cc(Cl)ccc32)[C@H]1c1cccc(Cl)c1F] | | 0.78 | 492 | E |
| A-6ai | Chiral | | 0.78 | 492 | E |
| A-6aj | 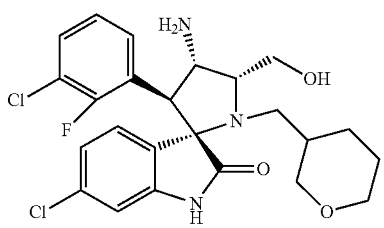 | | 0.63 | 494 | E |
| A-6ak | 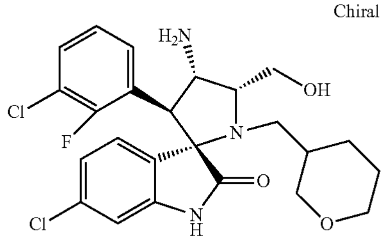 [SMILES: N[C@@H]1[C@H](CO)N(CC2CCCOC2)[C@@]2(C(=O)Nc3cc(Cl)ccc32)[C@H]1c1cccc(Cl)c1F] | Chiral | 0.63 | 494 | E |
| A-6al | 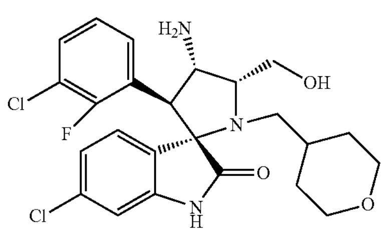 [SMILES: N[C@@H]1[C@H](CO)N(CC2CCOCC2)[C@@]2(C(=O)Nc3cc(Cl)ccc32)[C@H]1c1cccc(Cl)c1F] | | 0.60 | 494 | E |

TABLE 8-continued

| # | structure | | $t_{ret}$ [min] | $[M + H]^+$ | HPLC method |
|---|---|---|---|---|---|
| A-6am | 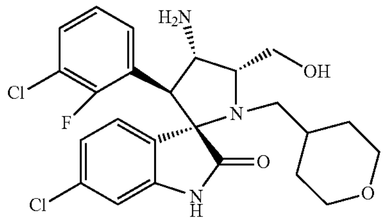 | Chiral | 0.60 | 494 | E |
| A-6an | 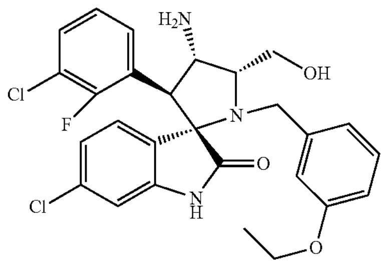 [SMILES: CCOc1cccc(CN2[C@@H](CO)[C@@H](N)[C@H](c3cccc(Cl)c3F)[C@]23C(=O)Nc2cc(Cl)ccc23)c1] | | 1.33 | 530 | A |
| A-6ao | 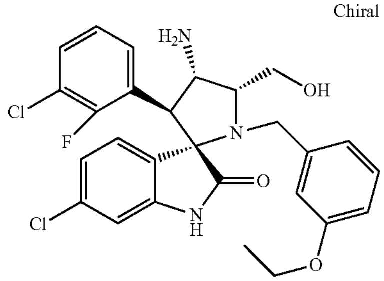 [SMILES: CCOc1cccc(CN2[C@@H](CO)[C@@H](N)[C@H](c3cccc(Cl)c3F)[C@]23C(=O)Nc2cc(Cl)ccc23)c1] | Chiral | 1.33 | 530 | A |
| A-6ap | 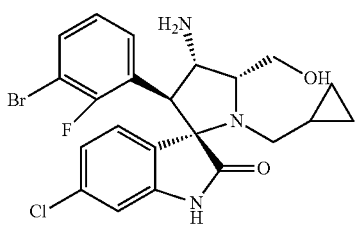 | | 1.96 | 469 | L |
| A-6aq | Chiral | | 1.96 | 469 | L |
| A-6ar | 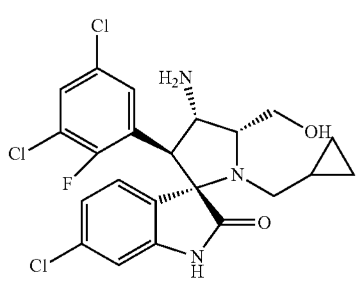 [SMILES: N[C@@H]1[C@H](CO)N(CC2CC2)[C@@]2(C(=O)Nc3cc(Cl)ccc32)[C@H]1c1cc(Cl)cc(Cl)c1F] | | 0.72 | 484/486 | E |

TABLE 8-continued

| # | structure | | $t_{ret}$ [min] | $[M + H]^+$ | HPLC method |
|---|---|---|---|---|---|
| A-6as | 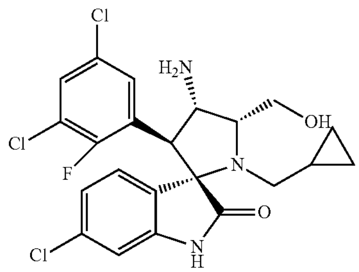 | Chiral | 0.72 | 484/486 | E |
| A-6at | 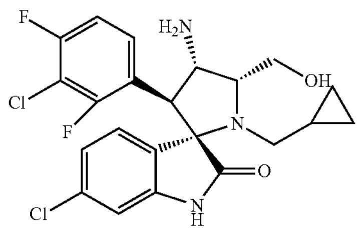 [SMILES: N[C@@H]1[C@H](CO)N(CC2CC2)[C@@]2(C(=O)Nc3cc(Cl)ccc32)[C@H]1c1ccc(F)c(Cl)c1F] | | 0.51 | 468 | F |
| A-6au | 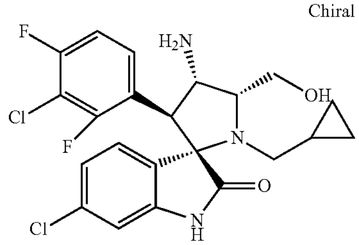 [SMILES: N[C@@H]1[C@H](CO)N(CC2CC2)[C@@]2(C(=O)Nc3cc(Cl)ccc32)[C@H]1c1ccc(F)c(Cl)c1F] | Chiral | 0.51 | 468 | F |
| A-6av | 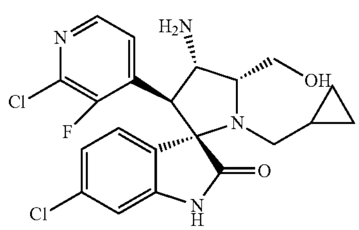 | | 0.58 | 451 | E |
| A-6aw | 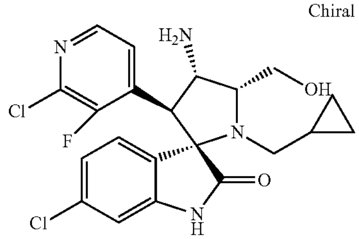 [SMILES: N[C@@H]1[C@H](CO)N(CC2CC2)[C@@]2(C(=O)Nc3cc(Cl)ccc32)[C@H]1c1ccnc(Cl)c1F] | Chiral | 0.58 | 451 | E |
| A-6ax | 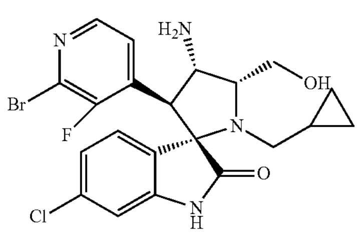 | | 0.45 | 495/497 | F |

TABLE 8-continued

| # | structure | | $t_{ret}$ [min] | $[M + H]^+$ | HPLC method |
|---|---|---|---|---|---|
| A-6ay | 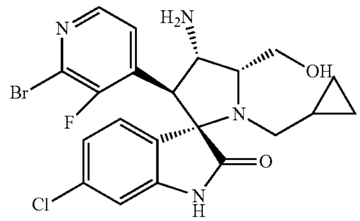 | Chiral | 0.45 | 495/497 | F |
| A-6az | 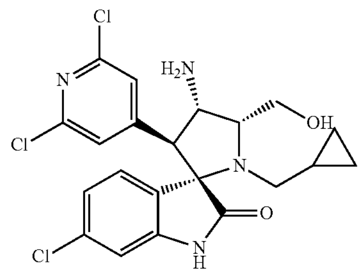 [SMILES: N[C@@H]1[C@H](CO)N(CC2CC2)[C@@]2(C(=O)Nc3cc(Cl)ccc32)[C@H]1c1cc(Cl)nc(Cl)c1] | | 0.64 | 467/469 | E |
| A-6ba | 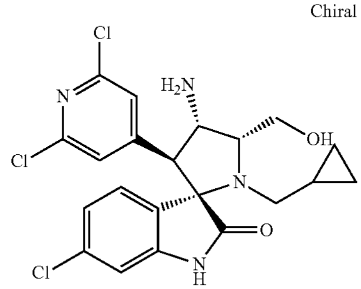 [SMILES: N[C@@H]1[C@H](CO)N(CC2CC2)[C@@]2(C(=O)Nc3cc(Cl)ccc32)[C@H]1c1cc(Cl)nc(Cl)c1] | Chiral | 0.64 | 467/469 | E |
| A-6bb | 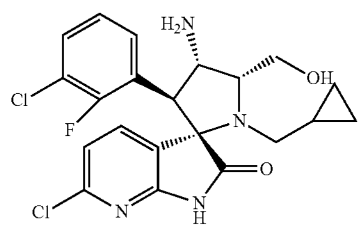 [SMILES: N[C@@H]1[C@H](CO)N(CC2CC2)[C@@]2(C(=O)Nc3nc(Cl)ccc32)[C@H]1c1cccc(Cl)c1F] | | 0.60 | 451 | E |
| A-6bc | Chiral | | 0.60 | 451 | E |
| A-6bd | Chiral | | 1.22 | 464 | A |

Synthesis of Intermediate A-7

(Hetero)Aromatic nitro aldehydes A-7 which are not commercially available can be obtained from methyl precursors B-3 either by enamine formation with DMF dimethylacetal (→B-4) and cleavage with NaIO₄ or by bromination with NBS/AIBN (→B-5) and oxidation witn NMO. Initially obtained intermediates A-7 can be modified to obtain further intermediates A-7 (e.g. by carboxylation).

heated to 90° C. under microwave irradiation for 30 min. Additional N,N-dimethylformamide dimethylacetal (207.1 mg, 1.738 mmol) is added and the resulting solution heated to 90° C. under microwave irradiation for 30 min. Again N,N-dimethylformamide dimethylacetal (207.1 mg, 1.738 mmol) is added and heated to 90° C. under microwave irradiation for 30 min. Then the solvent is removed under reduced pressure to provide crude intermediate B-4a, which is used without further purification in the next step.

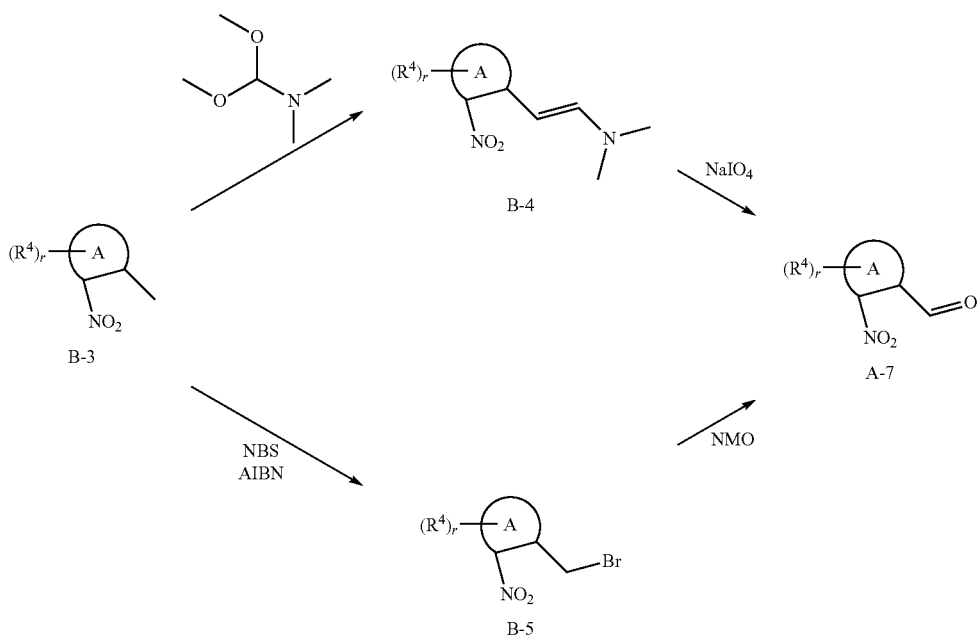

Experimental Procedure for the Synthesis of B-4a

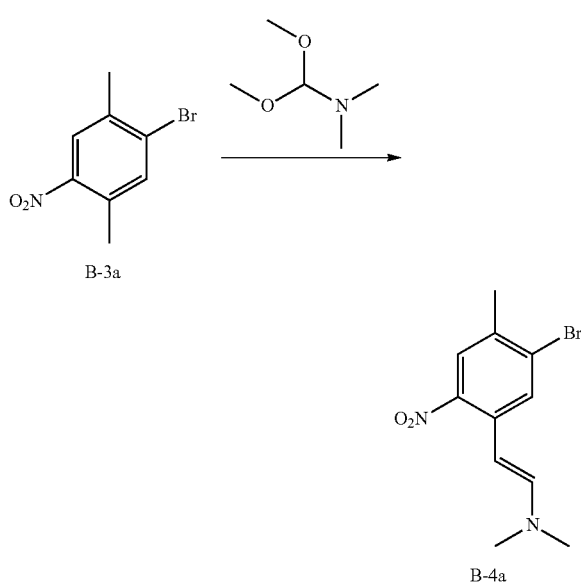

A solution of 1-bromo-2,5-dimethyl-4-nitrobenzene B-3a (200.0 mg, 0.869 mmol) and N,N-dimethylformamide dimethylacetal (124.3 mg, 1.043 mmol) in DMF (1.0 mL) is Experimental Procedure for the Synthesis of B-4c

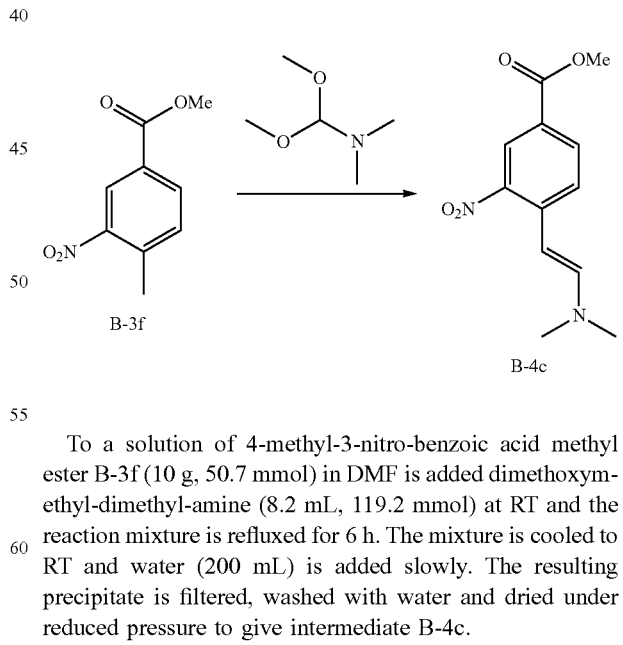

To a solution of 4-methyl-3-nitro-benzoic acid methyl ester B-3f (10 g, 50.7 mmol) in DMF is added dimethoxymethyl-dimethyl-amine (8.2 mL, 119.2 mmol) at RT and the reaction mixture is refluxed for 6 h. The mixture is cooled to RT and water (200 mL) is added slowly. The resulting precipitate is filtered, washed with water and dried under reduced pressure to give intermediate B-4c.

The following intermediates B-4 (Table 9) are available in an analogous manner starting from different compounds B-3.

TABLE 9

| # | structure | $t_{ret}$ [min] | $[M + H]^+$ | HPLC method |
|---|---|---|---|---|
| B-4a | 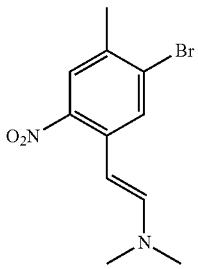 [SMILES: Cc1cc([N+](=O)[O-])c(/C=C/N(C)C)cc1Br] | 0.86 | 285 | E |
| B-4b | 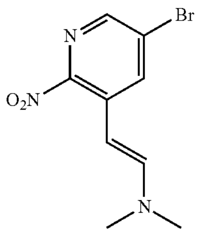 | 0.67 | 272 | E |
| B-4c | 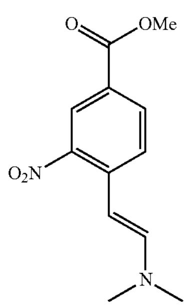 [SMILES: COC(=O)c1ccc(/C=C/N(C)C)c([N+](=O)[O-])c1] | n.a. | n.a. | n.a. |

Experimental Procedure for the Synthesis of A-7a

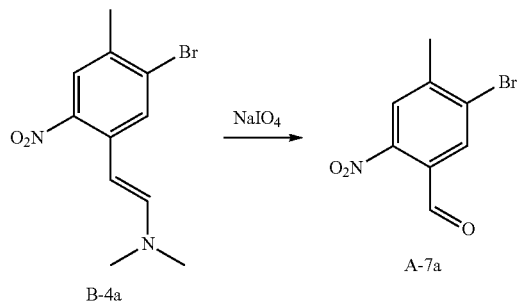

A solution of crude intermediate B-4a (232.0 mg, 0.813 mmol) in THF (2 mL) and water (2 mL) is treated with sodium metaperiodate (469.9 mg, 2.197 mmol) and stirred for 1 h at rt. The reaction is quenched with an aqueous solution of sodium hydrogencarbonate and extracted with EtOAc. The solvent is removed under reduced pressure to furnish crude intermediate A-7a, which is used without further purification.

Experimental Procedure for the Synthesis of A-7f

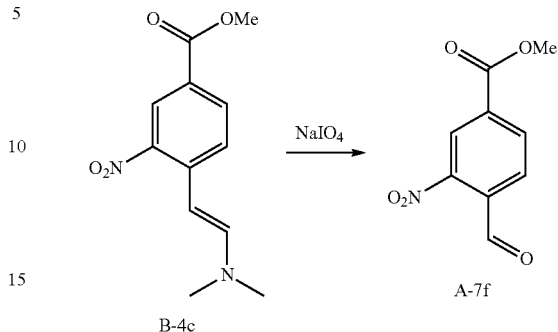

To a solution of intermediate B-4c (10 g, 40.0 mmol) in a mixture of THF and water is added NaIO$_4$ (25.6 g, 119.9 mmol) and the mixture is stirred at RT for 16 h. The resulting precipitate is filtered and washed with EtOAc. The liquids are combined and water and EtOAc is added. The phases are separated and the aqueous phase is extracted with EtOAc. The combined organic layer is washed with saturated NaHCO$_3$ solution and is dried (MgSO$_4$), filtered, concentrated in vacuo and the crude product A-7f is purified by chromatography or recrystallization if necessary. The following intermediates A-7 (table 10) are available in an analogous manner starting from different compounds B-4.

TABLE 10

| # | structure | $t_{ret}$ [min] | $[M + H]^+$ | HPLC method |
|---|---|---|---|---|
| A-7a | 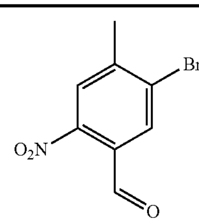 | 0.64 | n.a. | E |
| A-7b | 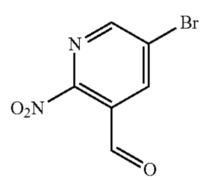 [SMILES: O=Cc1cc(Br)cnc1[N+](=O)[O-]] | 0.54 | n.a. | A |
| A-7f | 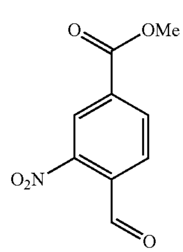 [SMILES: COC(=O)c1ccc(C=O)c([N+](=O)[O-])c1] | n.a. | n.a. | n.a. |

Experimental Procedure for the Synthesis of B-5a

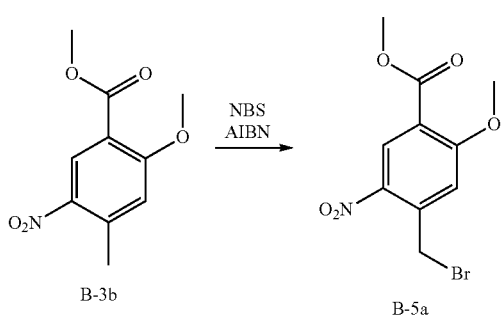

To a solution of methyl-2-methoxy-4-methyl-5-nitrobenzoate B-3b (250 mg, 1.088 mmol) in carbontetrachloride (10 mL) are added N-bromosuccinimide (251.0 mg, 1.410 mmol) and 2,2'-azobis(2-methylpropionitrile) (2.0 mg, 0.012 mmol). The resulting mixture is heated to reflux for 3 d and then cooled to rt. The reaction is quenched with water and the aqueous layer extracted with DCM. The combined organic layer is dried (MgSO$_4$), filtered, concentrated in vacuo and the crude product B-5a is purified by chromatography if necessary.

TABLE 11

| # | structure | t$_{ret}$ [min] | [M + H]$^+$ | HPLC method |
|---|---|---|---|---|
| B-5a | 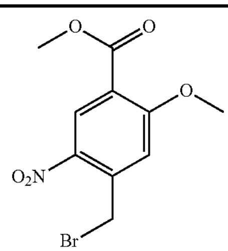 | 0.61 | 304 | E |

Experimental Procedure for the Synthesis of A-7c

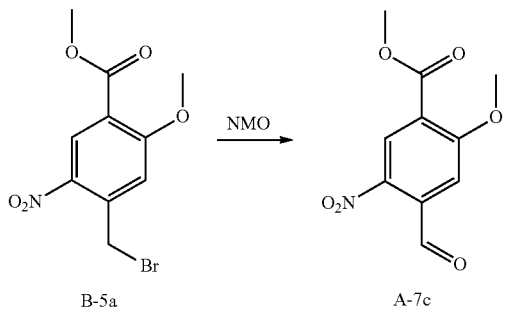

To a solution of intermediate B-5a (50.0 mg, 0.164 mmol) in acetonitrile (2 mL) is added 4 Å molecular sieve and N-methyl morpholine-N-oxide (40.0 mg, 0.341 mmol). The resulting mixture is stirred for 1 h at rt. Water is added, the molecular sieve is removed by filtration and the filtrate extracted with DCM. The combined organic layer is dried (MgSO$_4$), filtered, concentrated in vacuo and the crude product A-7c is purified by chromatography if necessary.

TABLE 12

| # | structure | t$_{ret}$ [min] | [M + H]$^+$ | HPLC method |
|---|---|---|---|---|
| A-7c | 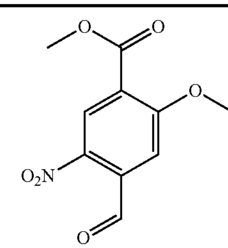 | 0.89 | 240 | A |

Experimental Procedure for the Synthesis of A-7e

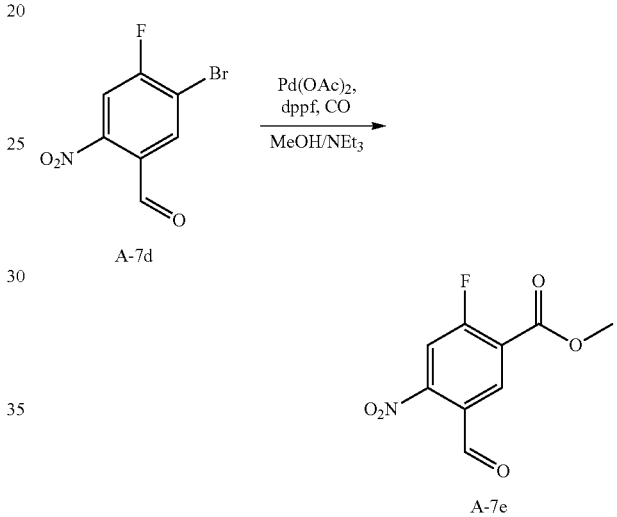

A solution of 5-bromo-4-fluoro-2-nitrobenzaldehyde A-7d (15.0 mg, 0.605 mmol) in MeOH (40 mL) is treated with 1,1'-bis(diphenylphosphanyl)ferrocene (36 mg, 0.065 mmol), palladium diacetate (14.0 mg, 0.062 mmol) and triethylamine (210 µL, 1.496 mmol). The reaction vessel is pressurized with carbonmonoxide (7 bar), the reaction mixture is heated to 80° C. and stirred for 16 h. The resulting solution is filtered over Isolute® and the solvent of the filtrate removed under reduced pressure to provide crude intermediate A-7e, which is used without further purification in the next step.

TABLE 13

| # | structure | t$_{ret}$ [min] | [M + H]$^+$ | HPLC method |
|---|---|---|---|---|
| A-7e | 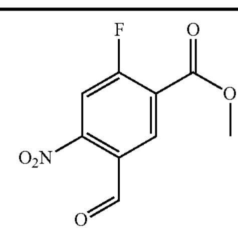 | 0.81 | n.a. | A |

Synthesis of Intermediates B-3c to B-3e

Experimental Procedure for the Synthesis of Intermediate B-3c

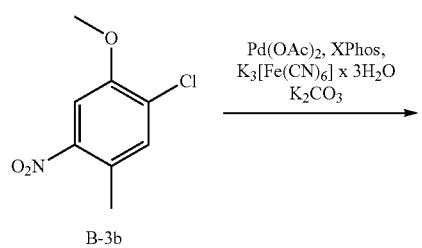

B-3b

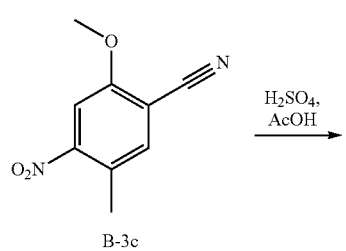

B-3c

To a solution of 1-chloro-2-methoxy-5-methyl-4-nitrobenzene (1.000 g, 4.960 mmol) in dioxane (2 mL) and water (2 mL) is added palladium diacetate (111 mg, 0.496 mmol), potassium ferrocyanide trihydrate (524 mg, 1.240 mmol), XPhos (473 mg, 0.992 mmol) and potassium carbonate (171 mg, 1.240 mmol). The resulting mixture is heated to 140° C. under microwave irradiation for 30 min. Water is added and the mixture extracted with EtOAc. The combined organic layer is dried (MgSO$_4$), filtered, concentrated in vacuo and the crude product B-3c is purified by chromatography if necessary.

Experimental Procedure for the Synthesis of Intermediate B-3d

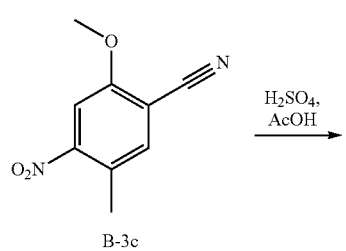

B-3c

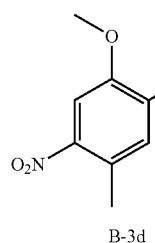

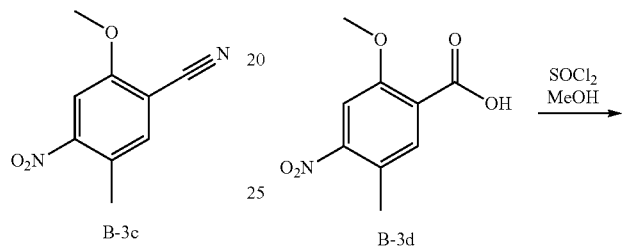

B-3d

A solution of B-3c (316.0 mg, 1.644 mmol) in AcOH (6 mL), sulfuric acid (6 mL) and water (6 mL) is heated to 120° C. for 2 h. After cooling to rt the solution is diluted with water and extracted with EtOAc. The combined organic layer is dried (MgSO$_4$), filtered, concentrated in vacuo and the crude product B-3d is purified by chromatography if necessary.

Experimental Procedure for the Synthesis of Intermediate B-3e

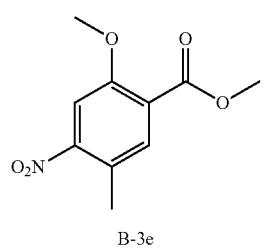

B-3e

To a solution of crude intermediate B-3d (103.0 mg, 0.488 mmol) in MeOH (5 mL) is added thionylchloride (360 μL, 4.963 mmol). The reaction mixture is heated to 60° C. and stirred for 16 h at this temperature. Water is added and the solution extracted with DCM. The combined organic layers are dried with sodium sulfate and the solvent is removed under reduced pressure. The combined organic layer is dried (MgSO$_4$), filtered, concentrated in vacuo and the crude product B-3e is purified by chromatography if necessary.

TABLE 14

| # | structure | $t_{ret}$ [min] | $[M + H]^+$ | HPLC method |
|---|---|---|---|---|
| B-3c | 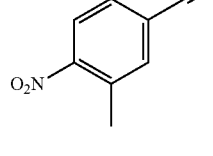 | 1.04. | n.a. | A |
| B-3d | 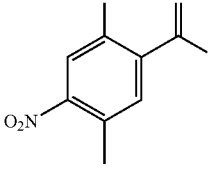 | 0.17 | 210 | A |
| B-3e | 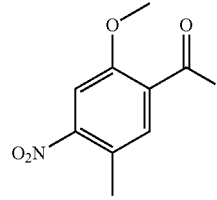 | 0.59 | 226 | E |

Synthesis of Intermediate A-8 (Method E)

Experimental Procedure for the Synthesis of A-8a

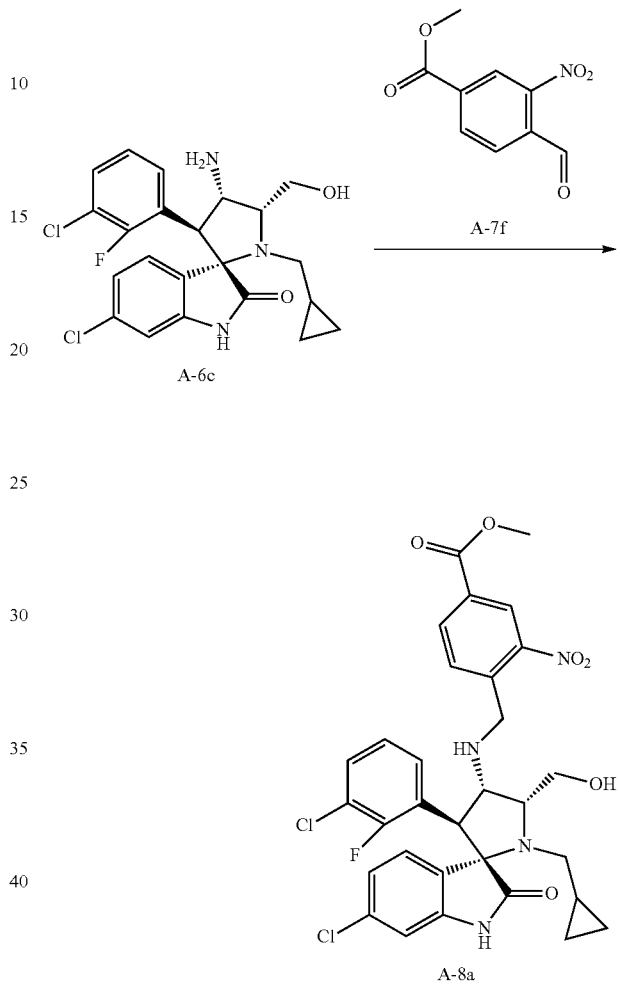

Intermediate A-6c (2.18 g, 4.85 mmol) is dissolved in DMF (3 mL) and treated with 4-formyl-3-nitrobenzoic acid methyl ester A-7f (0.97 g, 4.65 mmol) and AcOH (0.24 mL, 4.27 mmol). After 1 h the resulting mixture is cooled to 0° C. and sodium triacetoxyborohydride (2.6 g, 11.6 mmol) is slowly added. The cooling bath is removed and the mixture stirred for 16 h. The aqueous layer is extracted with DCM and the organic layers are combined. The solvents are removed under reduced pressure and the residue is dissolved in diethylether and washed with saturated sodium hydrogencarbonate solution. The organic layer is dried with sodium sulfate and the solvent evaporated to yield crude A-8a which is purified by chromatography if necessary.

The following intermediates A-8 (table 15) are available in an analogous manner starting from different intermediates A-6 and A-7.

TABLE 15
| # | structure | t_ret [min] | [M + H]+ | HPLC method |
|---|---|---|---|---|
| A-8a | 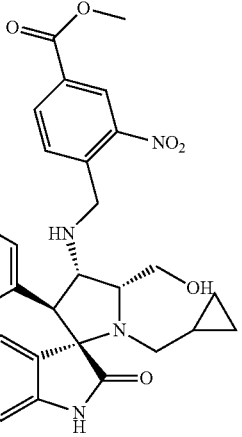 | 1.46 | 643 | A |
| A-8b Chiral | 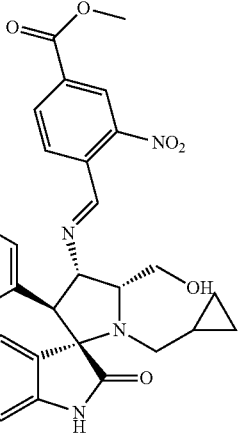 | 1.46 | 643 | A |
| A-8c Chiral | 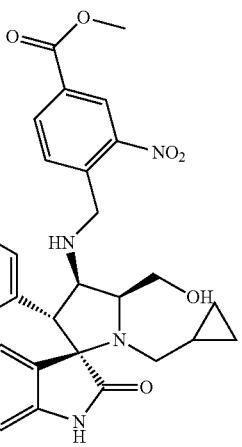 | 1.46 | 643 | A |

TABLE 15-continued

| # | structure | t_ret [min] | [M + H]+ | HPLC method |
|---|---|---|---|---|
| A-8d | 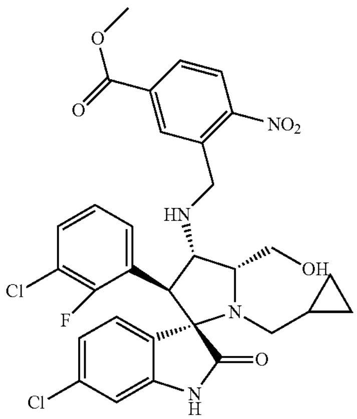 [SMILES: COC(=O)c1ccc([N+](=O)[O-])c(CN[C@@H]2[C@H](CO)N(CC3CC3)[C@@]3(C(=O)Nc4cc(Cl)ccc43)[C@H]2c2cccc(Cl)c2F)c1] | 0.84 | 643 | E |
| A-8e | Chiral | 0.84 | 643 | E |
| A-8f | Chiral | 0.84 | 643 | E |

TABLE 15-continued

| # | structure | | t_ret [min] | [M + H]+ | HPLC method |
|---|---|---|---|---|---|
| A-8g | 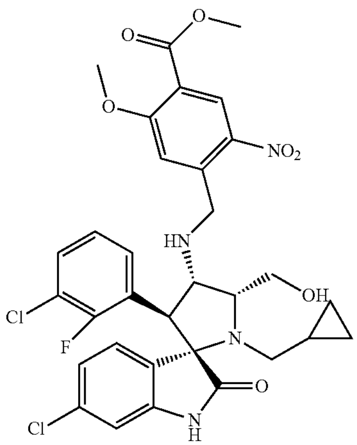 [SMILES: COC(=O)c1cc([N+](=O)[O-])c(CN[C@@H]2[C@H](CO)N(CC3CC3)[C@@]3(C(=O)Nc4cc(Cl)ccc43)[C@H]2c2cccc(Cl)c2F)cc1OC] | | 0.83 | 673 | E |
| A-8h | Chiral | | 0.83 | 673 | E |
| A-8i | Chiral | | 0.83 | 673 | E |

TABLE 15-continued

| # | structure | $t_{ret}$ [min] | [M + H]$^+$ | HPLC method |
|---|---|---|---|---|
| A-8j | 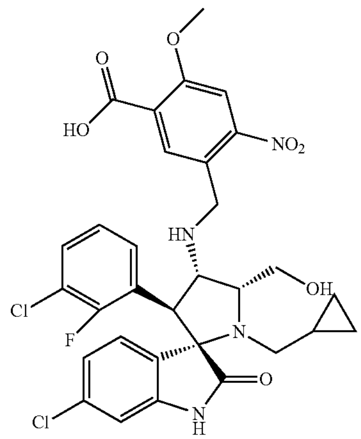 [SMILES: COc1cc([N+](=O)[O-])c(CN[C@@H]2[C@H](CO)N(CC3CC3)[C@@]3(C(=O)Nc4cc(Cl)ccc43)[C@H]2c2cccc(Cl)c2F)cc1C(=O)O] | 0.85 | 673 | E |
| A-8k | Chiral | 0.85 | 673 | E |
| A-8l | Chiral | 0.85 | 673 | E |

TABLE 15-continued
| # | structure | $t_{ret}$ [min] | $[M + H]^+$ | HPLC method |
|---|---|---|---|---|
| A-8m | 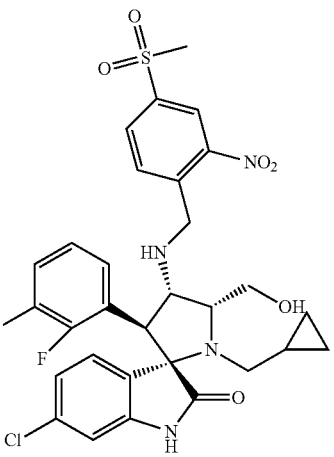 | 0.79 | 663 | E |
| A-8n | 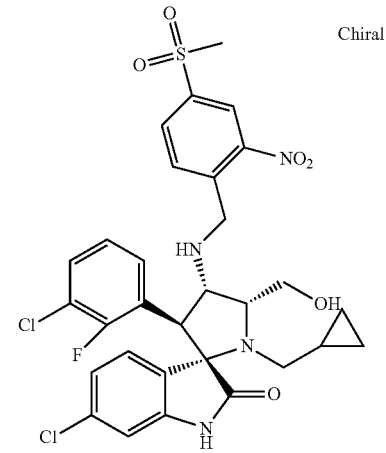 [SMILES: CS(=O)(=O)c1ccc(CN[C@@H]2[C@H](CO)N(CC3CC3)[C@@]3(C(=O)Nc4cc(Cl)ccc43)[C@H]2c2cccc(Cl)c2F)c([N+](=O)[O-])c1] Chiral | 0.79 | 663 | E |
| A-8o | 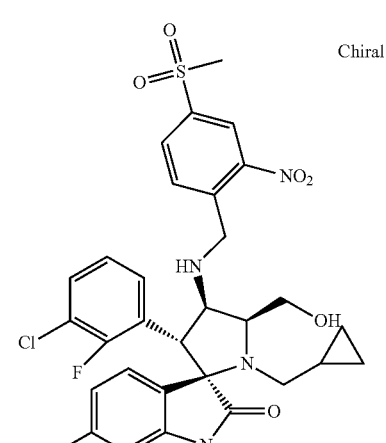 Chiral | 0.79 | 663 | E |

TABLE 15-continued
| # | structure | $t_{ret}$ [min] | $[M + H]^+$ | HPLC method |
|---|---|---|---|---|
| A-8p | 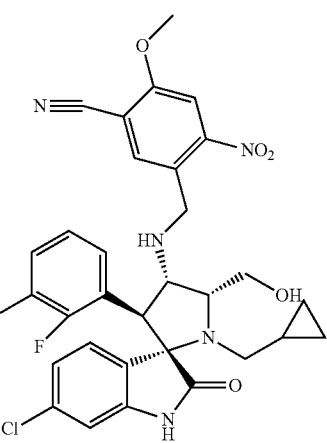 | 0.82 | 640 | E |
| A-8q | Chiral 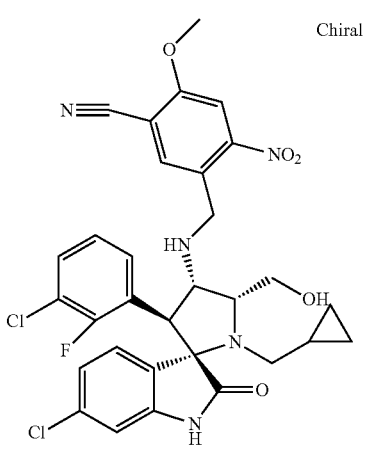 [SMILES: COc1cc([N+](=O)[O-])c(CN[C@@H]2[C@H](CO)N(CC3CC3)[C@@]3(C(=O)Nc4cc(Cl)ccc43)[C@H]2c2cccc(Cl)c2F)cc1C#N] | 0.82 | 640 | E |
| A-8r | Chiral 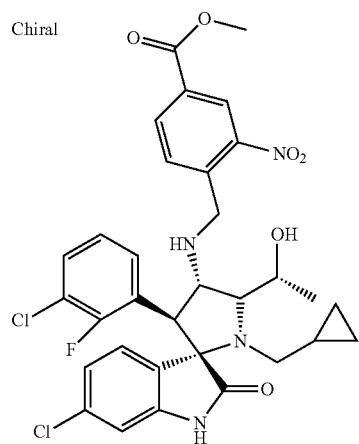 | 0.85 | 657 | G |

TABLE 15-continued

| # | structure | | $t_{ret}$ [min] | $[M + H]^+$ | HPLC method |
|---|---|---|---|---|---|
| A-8s | Chiral | | 0.87 | 657 | G |
| A-8t | Chiral | | 0.85 | 657 | G |
| A-8u | Chiral | | 0.86 | 657 | G |

TABLE 15-continued

| # | structure | $t_{ret}$ [min] | $[M + H]^+$ | HPLC method |
|---|---|---|---|---|
| A-8v | 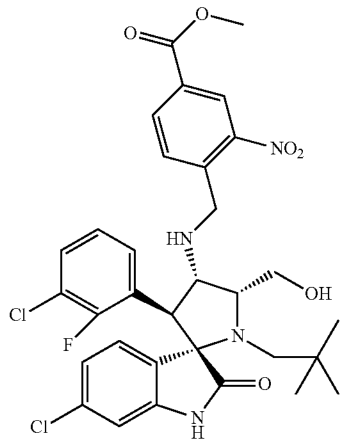 [SMILES: COC(=O)c1ccc(CN[C@@H]2[C@H](CO)N(CC(C)(C)C)[C@@]3(C(=O)Nc4cc(Cl)ccc43)[C@H]2c2cccc(Cl)c2F)c([N+](=O)[O-])c1] | 0.88 | 659 | E |
| A-8w | Chiral | 0.88 | 659 | E |
| A-8x | 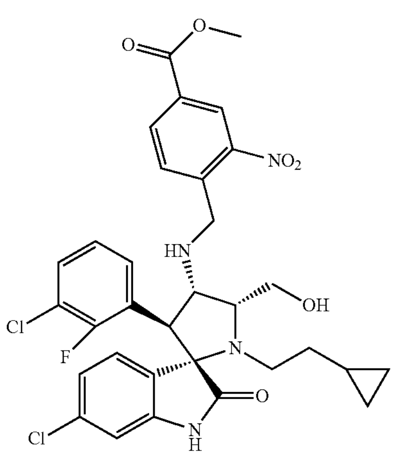 [SMILES: COC(=O)c1ccc(CN[C@@H]2[C@H](CO)N(CCC3CC3)[C@@]3(C(=O)Nc4cc(Cl)ccc43)[C@H]2c2cccc(Cl)c2F)c([N+](=O)[O-])c1] | 0.89 | 657 | E |

TABLE 15-continued

| # | structure | | $t_{ret}$ [min] | $[M + H]^+$ | HPLC method |
|---|---|---|---|---|---|
| A-8y | 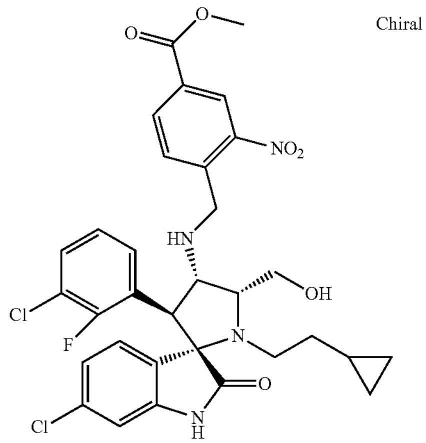 [SMILES: COC(=O)c1ccc(CN[C@@H]2[C@H](CO)N(CCC3CC3)[C@@]3(C(=O)Nc4cc(Cl)ccc43)[C@H]2c2cccc(Cl)c2F)c([N+](=O)[O-])c1] | Chiral | 0.89 | 657 | E |
| A-8z | 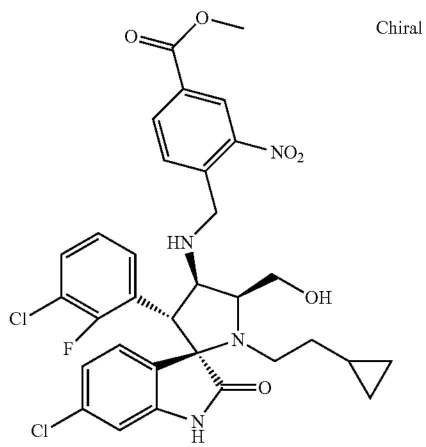 [SMILES: COC(=O)c1ccc(CN[C@H]2[C@@H](CO)N(CCC3CC3)[C@]3(C(=O)Nc4cc(Cl)ccc43)[C@@H]2c2cccc(Cl)c2F)c([N+](=O)[O-])c1] | Chiral | 0.89 | 657 | E |
| A-8aa | 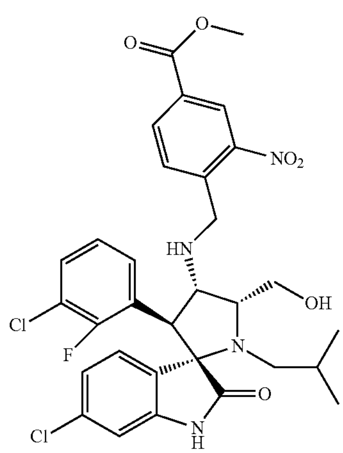 [SMILES: COC(=O)c1ccc(CN[C@@H]2[C@H](CO)N(CC(C)C)[C@@]3(C(=O)Nc4cc(Cl)ccc43)[C@H]2c2cccc(Cl)c2F)c([N+](=O)[O-])c1] | | 0.89 | 645 | E |

TABLE 15-continued

| # | structure | $t_{ret}$ [min] | $[M + H]^+$ | HPLC method |
|---|---|---|---|---|
| A-8ab | Chiral | 0.89 | 645 | E |
| A-8ac | Chiral | 0.89 | 645 | E |
| A-8ad | 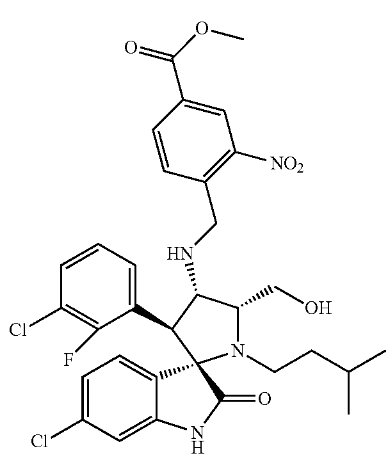 [SMILES: COC(=O)c1ccc(CN[C@@H]2[C@H](CO)N(CCC(C)C)[C@@]3(C(=O)Nc4cc(Cl)ccc43)[C@H]2c2cccc(Cl)c2F)c([N+](=O)[O-])c1] | 1.14 | 609 | A |

TABLE 15-continued
| # | structure | | $t_{ret}$ [min] | [M + H]⁺ | HPLC method |
|---|---|---|---|---|---|
| A-8ae | 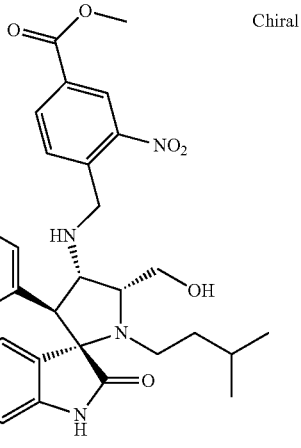 | Chiral | 1.14 | 609 | A |
| A-8af | 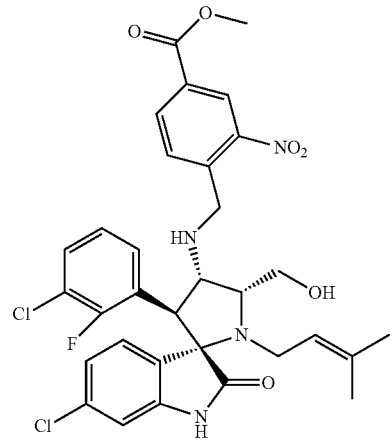 [SMILES: COC(=O)c1ccc(CN[C@@H]2[C@H](CO)N(CC=C(C)C)[C@@]3(C(=O)Nc4cc(Cl)ccc43)[C@H]2c2cccc(Cl)c2F)c([N+](=O)[O-])c1] | | 1.53 | 657 | A |
| A-8ag | 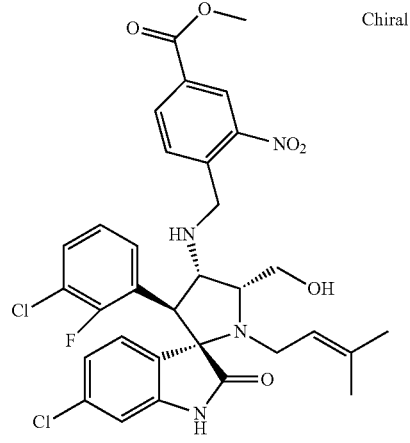 [SMILES: COC(=O)c1ccc(CN[C@@H]2[C@H](CO)N(CC=C(C)C)[C@@]3(C(=O)Nc4cc(Cl)ccc43)[C@H]2c2cccc(Cl)c2F)c([N+](=O)[O-])c1] | Chiral | 1.53 | 657 | A |

TABLE 15-continued
| # | structure | t_ret [min] | [M + H]+ | HPLC method |
|---|---|---|---|---|
| A-8ah | 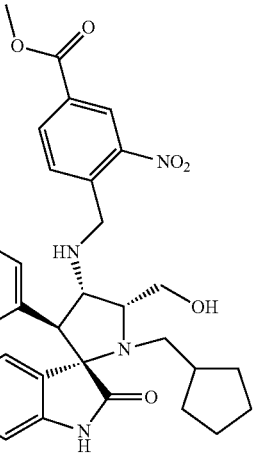 | 0.94 | 671 | E |
| A-8ai | 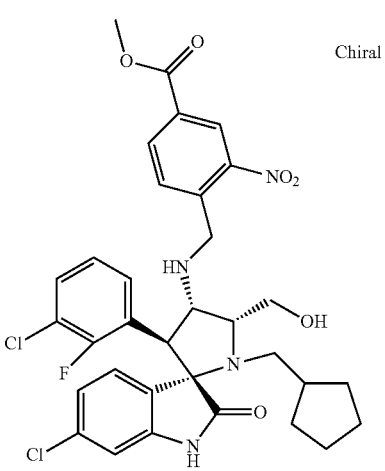 [SMILES: COC(=O)c1ccc(CN[C@@H]2[C@H](CO)N(CC3CCCC3)[C@@]3(C(=O)Nc4cc(Cl)ccc43)[C@H]2c2cccc(Cl)c2F)c([N+](=O)[O-])c1] Chiral | 0.94 | 671 | E |
| A-8aj | 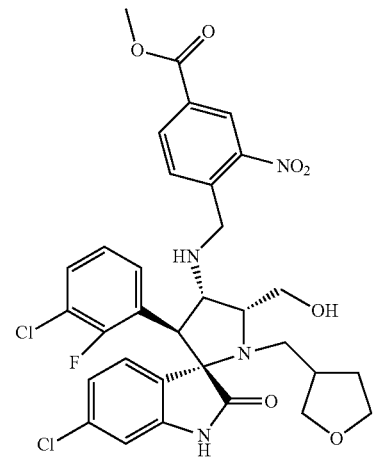 [SMILES: COC(=O)c1ccc(CN[C@@H]2[C@H](CO)N(CC3CCOC3)[C@@]3(C(=O)Nc4cc(Cl)ccc43)[C@H]2c2cccc(Cl)c2F)c([N+](=O)[O-])c1] | 0.79 | 673 | E |

TABLE 15-continued

| # | structure | $t_{ret}$ [min] | $[M + H]^+$ | HPLC method |
|---|---|---|---|---|
| A-8ak | 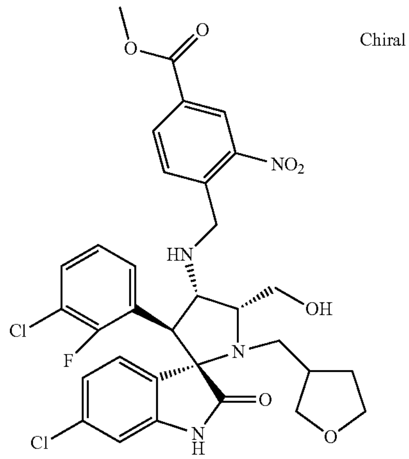 [SMILES: COC(=O)c1ccc(CN[C@@H]2[C@H](CO)N(CC3CCOC3)[C@@]3(C(=O)Nc4cc(Cl)ccc43)[C@H]2c2cccc(Cl)c2F)c([N+](=O)[O-])c1] | 0.79 Chiral | 673 | E |
| A-8al | 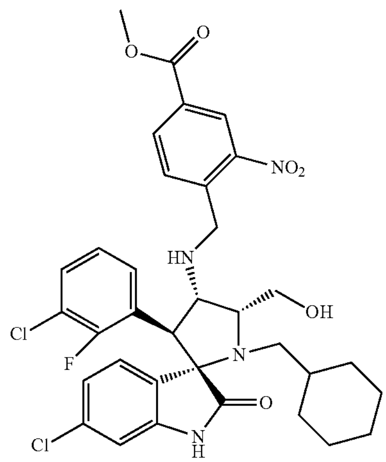 [SMILES: COC(=O)c1ccc(CN[C@@H]2[C@H](CO)N(CC3CCCCC3)[C@@]3(C(=O)Nc4cc(Cl)ccc43)[C@H]2c2cccc(Cl)c2F)c([N+](=O)[O-])c1] | 1.00 | 658 | E |
| A-8am | 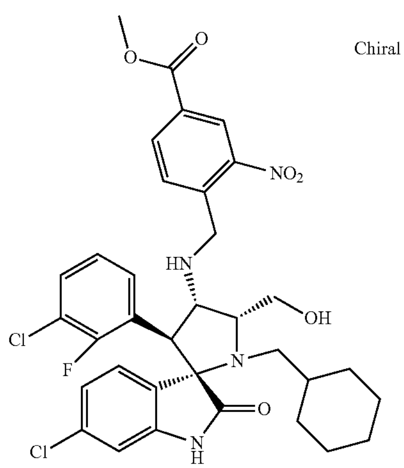 [SMILES: COC(=O)c1ccc(CN[C@@H]2[C@H](CO)N(CC3CCCCC3)[C@@]3(C(=O)Nc4cc(Cl)ccc43)[C@H]2c2cccc(Cl)c2F)c([N+](=O)[O-])c1] | 1.00 Chiral | 658 | E |

TABLE 15-continued
| # | structure | $t_{ret}$ [min] | [M + H]⁺ | HPLC method |
|---|---|---|---|---|
| A-8an | 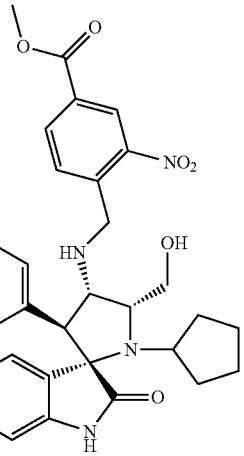 | 1.51 | 657 | A |
| A-8ao | 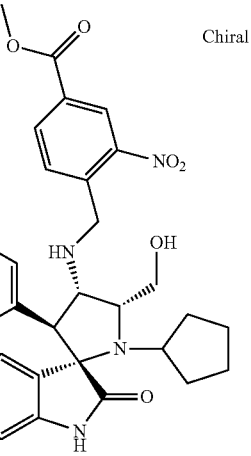 Chiral | 1.51 | 657 | A |
| A-8ap | 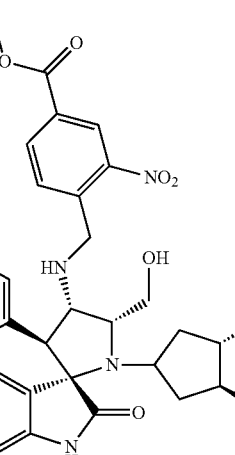 | 0.94 | 685 | E |

TABLE 15-continued
| # | structure | $t_{ret}$ [min] | $[M + H]^+$ | HPLC method |
|---|---|---|---|---|
| A-8aq | 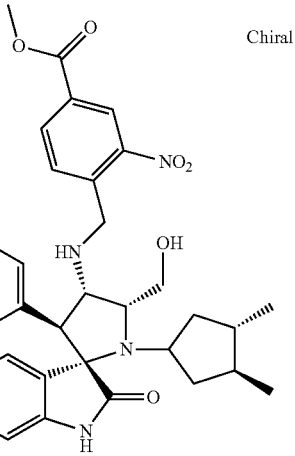 | 0.94 Chiral | 685 | E |
| A-8ar | 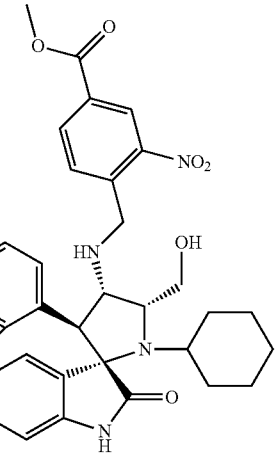 | 0.92 | 671 | E |
| A-8as | 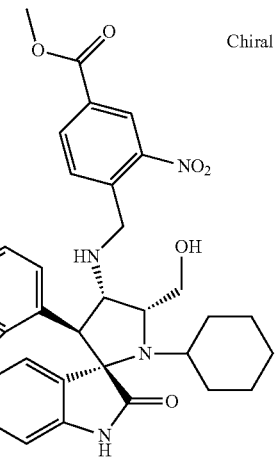 | 0.92 Chiral | 671 | E |

137
TABLE 15-continued
| # | structure | $t_{ret}$ [min] | [M + H]⁺ | HPLC method |
|---|---|---|---|---|
| A-8at | 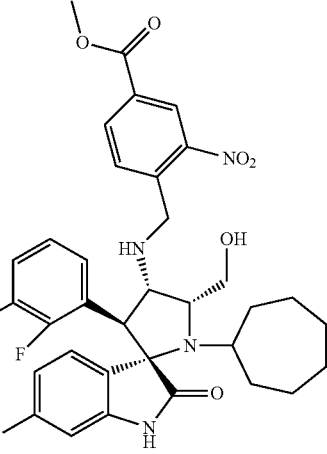 | 0.87 | 683 | F |
| A-8au | 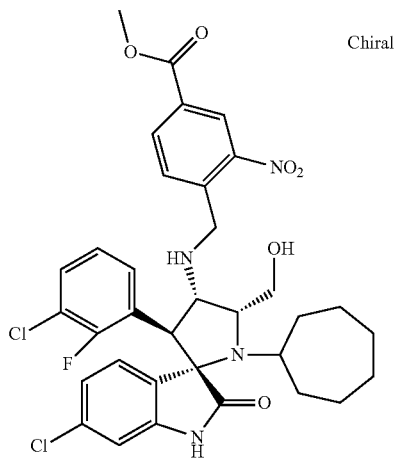 [SMILES: COC(=O)c1ccc(CN[C@@H]2[C@H](CO)N(C3CCCCCC3)[C@@]3(C(=O)Nc4cc(Cl)ccc43)[C@H]2c2cccc(Cl)c2F)c([N+](=O)[O-])c1] Chiral | 0.87 | 683 | F |
| A-8av | 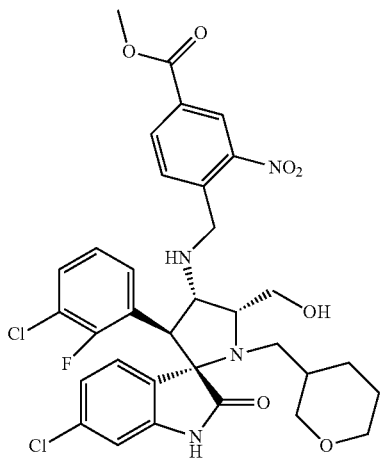 [SMILES: COC(=O)c1ccc(CN[C@@H]2[C@H](CO)N(CC3CCCOC3)[C@@]3(C(=O)Nc4cc(Cl)ccc43)[C@H]2c2cccc(Cl)c2F)c([N+](=O)[O-])c1] | 0.84 | 687 | E |

TABLE 15-continued

| # | structure | $t_{ret}$ [min] | [M + H]$^+$ | HPLC method |
|---|---|---|---|---|
| A-8aw | 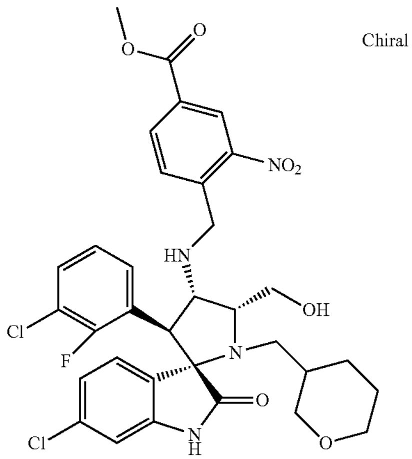 [SMILES: COC(=O)c1ccc(CN[C@@H]2[C@H](CO)N(CC3CCCOC3)[C@@]3(C(=O)Nc4cc(Cl)ccc43)[C@H]2c2cccc(Cl)c2F)c([N+](=O)[O-])c1] | 0.84 Chiral | 687 | E |
| A-8ax | 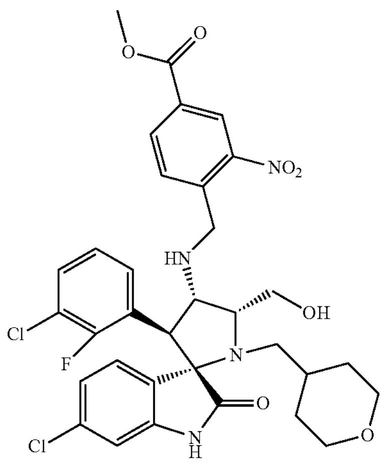 [SMILES: COC(=O)c1ccc(CN[C@@H]2[C@H](CO)N(CC3CCOCC3)[C@@]3(C(=O)Nc4cc(Cl)ccc43)[C@H]2c2cccc(Cl)c2F)c([N+](=O)[O-])c1] | 0.80 | 687 | E |
| A-8ay | 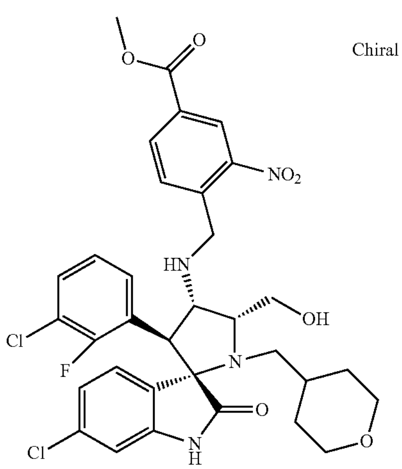 [SMILES: COC(=O)c1ccc(CN[C@@H]2[C@H](CO)N(CC3CCOCC3)[C@@]3(C(=O)Nc4cc(Cl)ccc43)[C@H]2c2cccc(Cl)c2F)c([N+](=O)[O-])c1] | 0.80 Chiral | 687 | E |

TABLE 15-continued

| # | structure | $t_{ret}$ [min] | [M + H]⁺ | HPLC method |
|---|---|---|---|---|
| A-8az | 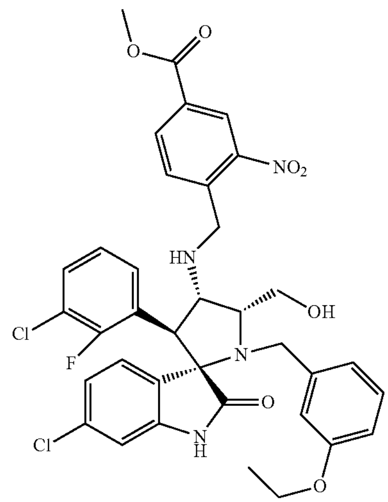 [SMILES: CCOc1cccc(CN2[C@@H](CO)[C@@H](NCc3ccc(C(=O)OC)cc3[N+](=O)[O-])[C@H](c3cccc(Cl)c3F)[C@]23C(=O)Nc2cc(Cl)ccc23)c1] | 1.54 | 723 | A |
| A-8ba | 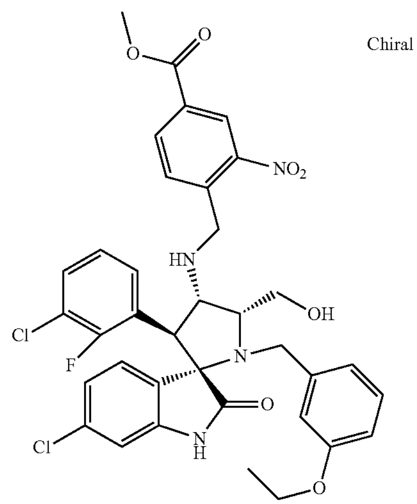 [SMILES: CCOc1cccc(CN2[C@@H](CO)[C@@H](NCc3ccc(C(=O)OC)cc3[N+](=O)[O-])[C@H](c3cccc(Cl)c3F)[C@]23C(=O)Nc2cc(Cl)ccc23)c1] | 1.54 Chiral | 723 | A |
| A-8bb | 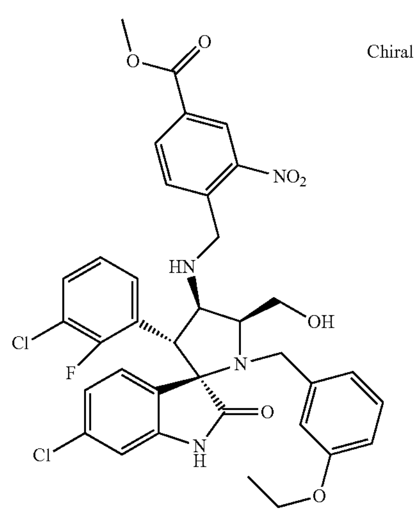 [SMILES: CCOc1cccc(CN2[C@H](CO)[C@H](NCc3ccc(C(=O)OC)cc3[N+](=O)[O-])[C@@H](c3cccc(Cl)c3F)[C@@]23C(=O)Nc2cc(Cl)ccc23)c1] | 1.54 Chiral | 723 | A |

TABLE 15-continued

| # | structure | $t_{ret}$ [min] | $[M + H]^+$ | HPLC method |
|---|---|---|---|---|
| A-8bc | 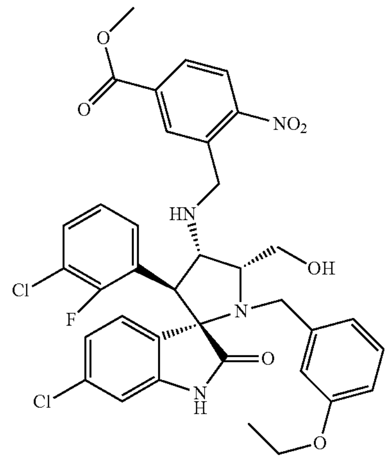 [SMILES: CCOc1cccc(CN2[C@@H](CO)[C@@H](NCc3cc(C(=O)OC)ccc3[N+](=O)[O-])[C@H](c3cccc(Cl)c3F)[C@]23C(=O)Nc2cc(Cl)ccc23)c1] | 1.54 | 723 | A |
| A-8bd | Chiral | 1.54 | 723 | A |
| A-8be | 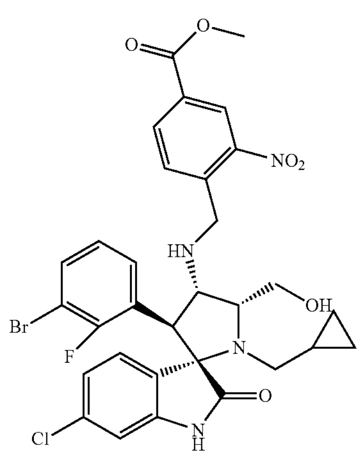 | 1.48 | 687 | A |

TABLE 15-continued
| # | structure | t_ret [min] | [M + H]+ | HPLC method |
|---|---|---|---|---|
| A-8bf | 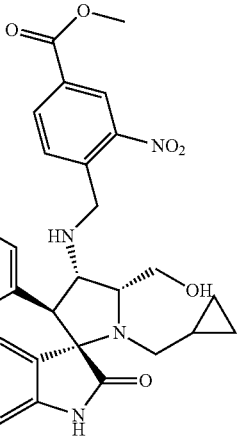 | 1.48 | 687 | A |
| A-8bg | 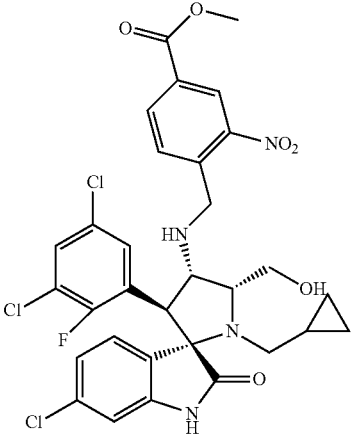 [SMILES: COC(=O)c1ccc(CN[C@@H]2[C@H](CO)N(CC3CC3)[C@@]3(C(=O)Nc4cc(Cl)ccc43)[C@H]2c2cc(Cl)cc(Cl)c2F)c([N+](=O)[O-])c1] | 1.52 | 677 | A |
| A-8bh | Chiral 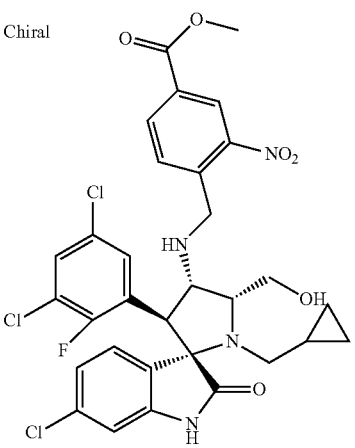 [SMILES: COC(=O)c1ccc(CN[C@@H]2[C@H](CO)N(CC3CC3)[C@@]3(C(=O)Nc4cc(Cl)ccc43)[C@H]2c2cc(Cl)cc(Cl)c2F)c([N+](=O)[O-])c1] | 1.52 | 677 | A |

TABLE 15-continued
| # | structure | $t_{ret}$ [min] | $[M + H]^+$ | HPLC method |
|---|---|---|---|---|
| A-8bi | 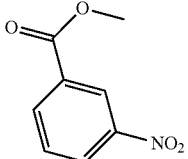 | 0.85 | 661 | E |
| A-8bj | Chiral 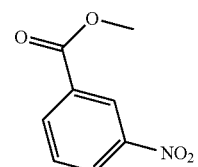 | 0.85 | 661 | E |
| A-8bk | 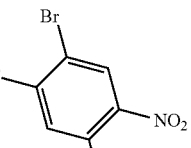 | 0.93 | 683 | E |

TABLE 15-continued
| # | structure | $t_{ret}$ [min] | [M + H]$^+$ | HPLC method |
|---|---|---|---|---|
| A-8bl | Chiral 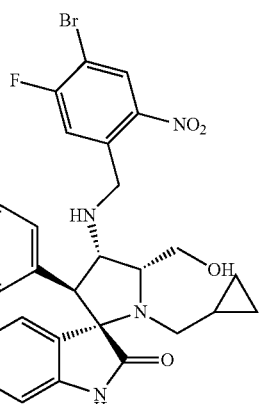 | 0.93 | 683 | E |
| A-8bm | 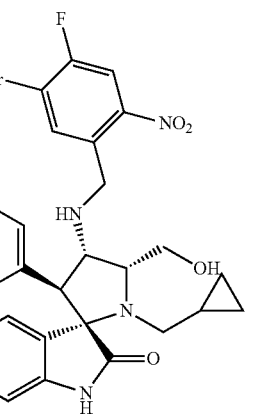 | 0.93 | 683 | E |
| A-8bn | Chiral 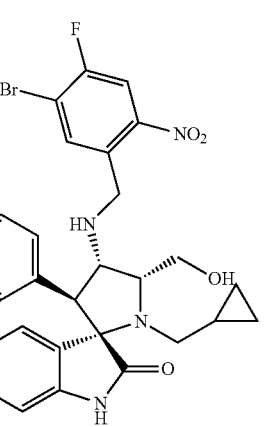 | 0.93 | 683 | E |

TABLE 15-continued

| # | | structure | t_ret [min] | [M + H]+ | HPLC method |
|---|---|---|---|---|---|
| A-8bo | | 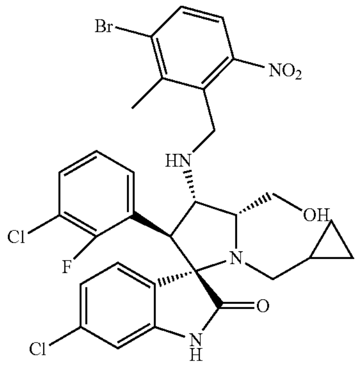 [SMILES: Cc1c(Br)ccc([N+](=O)[O-])c1CN[C@@H]1[C@H](CO)N(CC2CC2)[C@@]2(C(=O)Nc3cc(Cl)ccc32)[C@H]1c1cccc(Cl)c1F] | 1.27 | 642 | K |
| A-8bp | Chiral | 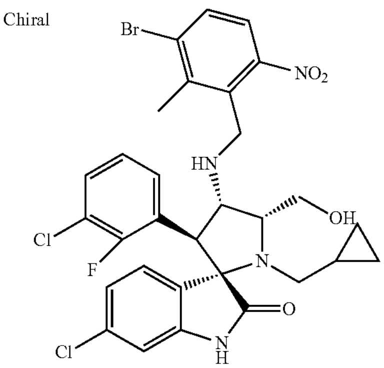 [SMILES: Cc1c(Br)ccc([N+](=O)[O-])c1CN[C@@H]1[C@H](CO)N(CC2CC2)[C@@]2(C(=O)Nc3cc(Cl)ccc32)[C@H]1c1cccc(Cl)c1F] | 1.27 | 642 | K |
| A-8bq | | 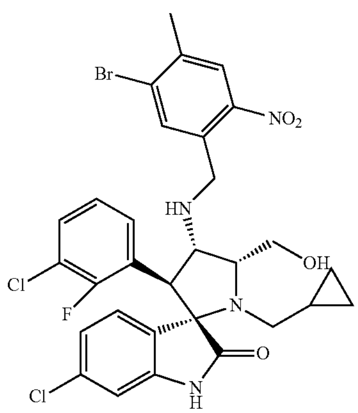 [SMILES: Cc1cc([N+](=O)[O-])c(CN[C@@H]2[C@H](CO)N(CC3CC3)[C@@]3(C(=O)Nc4cc(Cl)ccc43)[C@H]2c2cccc(Cl)c2F)cc1Br] | 1.73 | 643 | A |
| A-8br | Chiral | 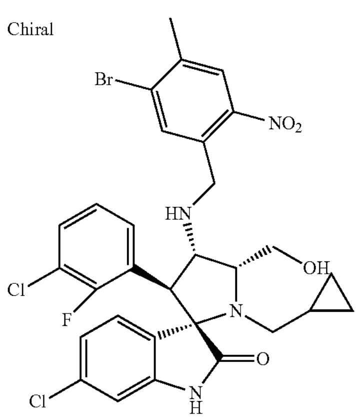 [SMILES: Cc1cc([N+](=O)[O-])c(CN[C@@H]2[C@H](CO)N(CC3CC3)[C@@]3(C(=O)Nc4cc(Cl)ccc43)[C@H]2c2cccc(Cl)c2F)cc1Br] | 1.73 | 643 | A |

TABLE 15-continued

| # | structure | $t_{ret}$ [min] | [M + H]⁺ | HPLC method |
|---|---|---|---|---|
| A-8bs | 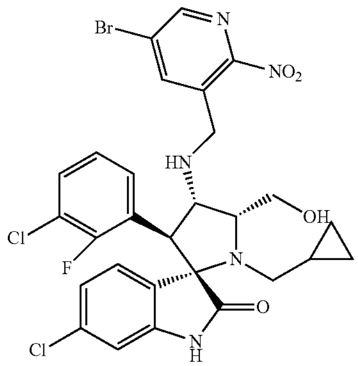 [SMILES: O=C1Nc2cc(Cl)ccc2[C@@]12[C@@H](c1cccc(Cl)c1F)[C@H](NCc1cc(Br)cnc1[N+](=O)[O-])[C@H](CO)N2CC1CC1] | 0.94 | 630 | E |
| A-8bt | Chiral | 0.94 | 630 | E |
| A-8bu | 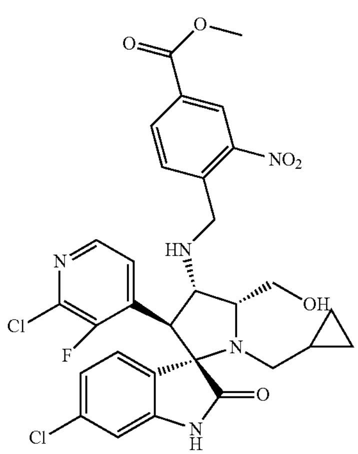 | 0.79 | 644 | E |

TABLE 15-continued
| # | structure | $t_{ret}$ [min] | $[M + H]^+$ | HPLC method |
|---|---|---|---|---|
| A-8bv | Chiral 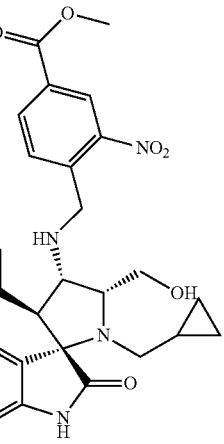 | 0.79 | 644 | E |
| A-8bw | 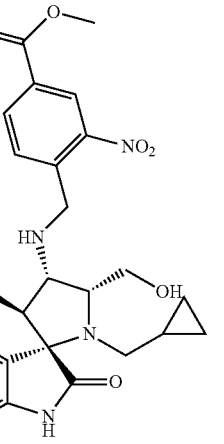 | 0.75 | 688 | F |
| A-8bx | Chiral 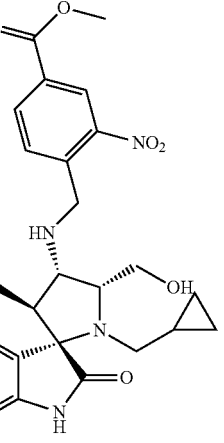 | 0.75 | 688 | F |

TABLE 15-continued

| # | structure | t$_{ret}$ [min] | [M + H]$^+$ | HPLC method |
|---|---|---|---|---|
| A-8by | 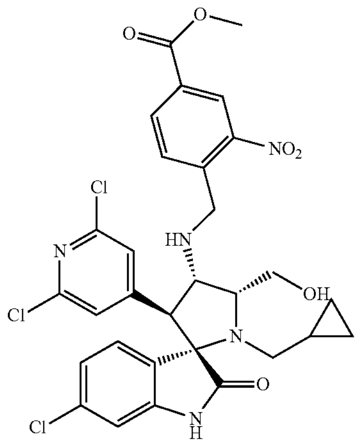 [SMILES: COC(=O)c1ccc(CN[C@@H]2[C@H](CO)N(CC3CC3)[C@@]3(C(=O)Nc4cc(Cl)ccc43)[C@H]2c2cc(Cl)nc(Cl)c2)c([N+](=O)[O-])c1] | 0.81 | 660/662 | F |
| A-8bz | Chiral | 0.81 | 660/662 | F |
| A-8ca | 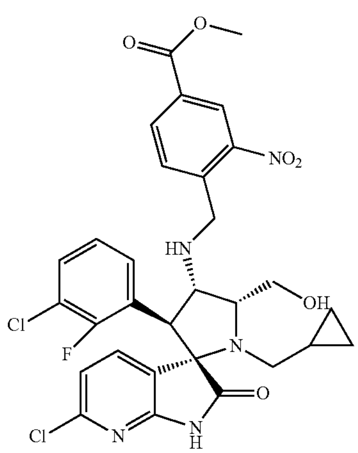 | 0.80 | 644 | E |

TABLE 15-continued
| # | structure | $t_{ret}$ [min] | $[M + H]^+$ | HPLC method |
|---|---|---|---|---|
| A-8cb | Chiral 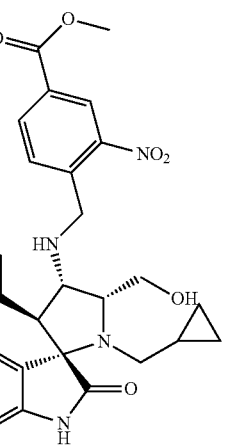 | 0.80 | 644 | E |
| A-8cc | Chiral 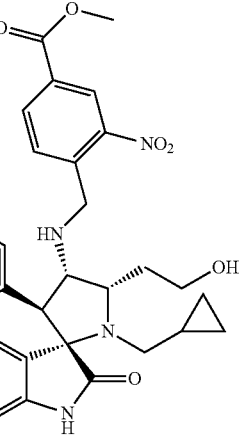 | 0.85 | 657 | E |
| A-8cd | Chiral 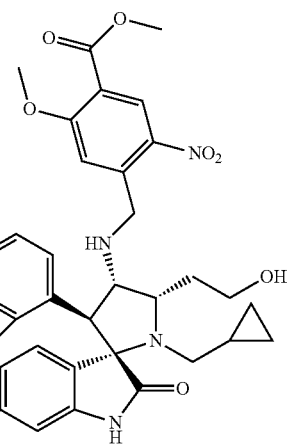 | 1.44 | 687 | A |

TABLE 15-continued

| # | structure | $t_{ret}$ [min] | $[M + H]^+$ | HPLC method |
|---|---|---|---|---|
| A-8ce | Chiral | 0.84 | 657 | E |
| A-8cf | Chiral | 0.92 | 693 | E |

Synthesis of Intermediate A-7 (Method F)

Experimental Procedure for the Synthesis of Intermediate A-8cg

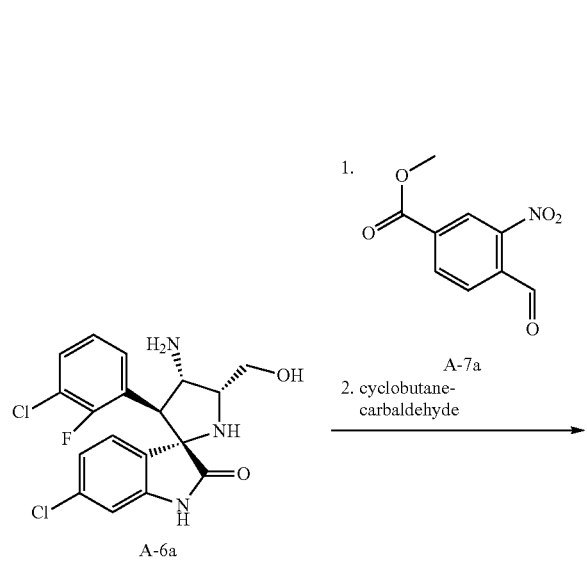

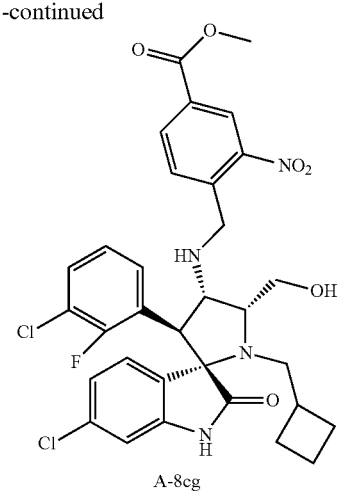

Intermediate A-6a (200 mg, 0.505 mmol) is dissolved in DMF (4 mL) and treated with 4-formyl-3-nitrobenzoic acid methyl ester A-7a (108 mg, 0.501 mmol) and AcOH (60 μL, 1.05 mmol). After 1 h sodium triacetoxyborohydride (250 mg, 1.15 mmol) is slowly added and the mixture is stirred over night. Cyclobutanecarbaldehyde (44.7 mg, 0.505 mmol) is added and the mixture is stirred for 1 h. Sodium triacetoxyborohydride (250 mg, 1.15 mmol) is slowly added and the mixture is stirred over night. Water is added and the mixture is extracted with DCM and the combined organic layer is dried with sodium sulfate. The solvents are removed under reduced pressure to give crude intermediate A-8cg which is purified by chromatography if necessary.

The following compounds A-8 (table 16) are available in an analogous manner starting from different intermediates A-6, A-7 and different aldehydes.

TABLE 16

| # | structure | $t_{ret}$ [min] | $[M + H]^+$ | HPLC method |
|---|---|---|---|---|
| A-8cg | 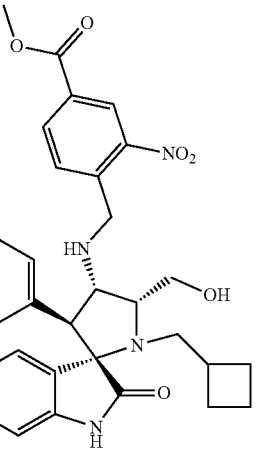 | 0.91 | 657 | E |
| A-8ch | Chiral 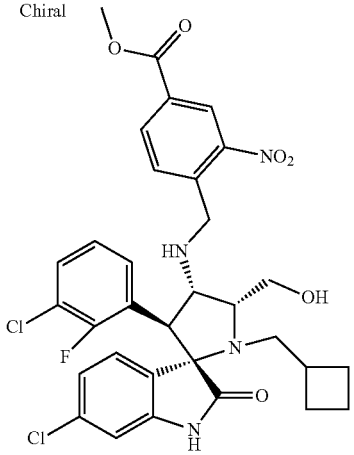 [SMILES: COC(=O)c1ccc(CN[C@@H]2[C@H](CO)N(CC3CCC3)[C@@]3(C(=O)Nc4cc(Cl)ccc43)[C@H]2c2cccc(Cl)c2F)c([N+](=O)[O-])c1] | 0.91 | 657 | E |
| A-8ci | 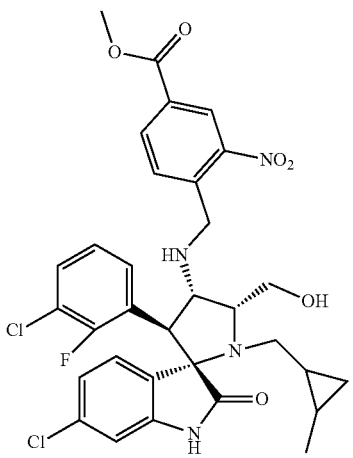 [SMILES: COC(=O)c1ccc(CN[C@@H]2[C@H](CO)N(CC3CC3C)[C@@]3(C(=O)Nc4cc(Cl)ccc43)[C@H]2c2cccc(Cl)c2F)c([N+](=O)[O-])c1] | 0.91 | 657 | E |

TABLE 16-continued
| # | structure | $t_{ret}$ [min] | $[M + H]^+$ | HPLC method |
|---|---|---|---|---|
| A-8cj | 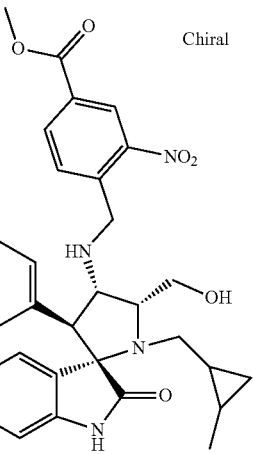 Chiral | 0.91 | 657 | E |
| A-8ck | 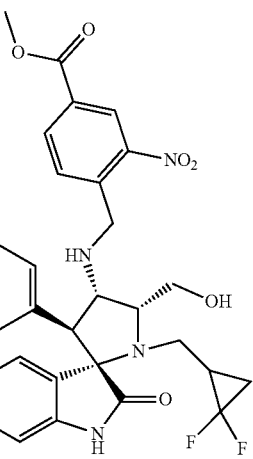 | 0.85 | 679 | E |
| A-8cl | 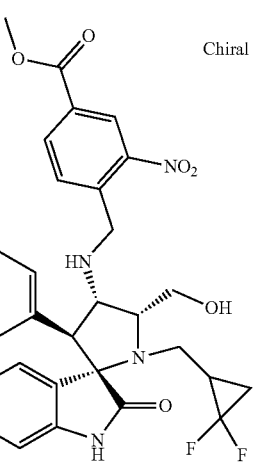 Chiral | 0.85 | 679 | E |

167
Synthesis of Compounds (I) (Method G)

Experimental Procedure for the Synthesis of Compound I-1

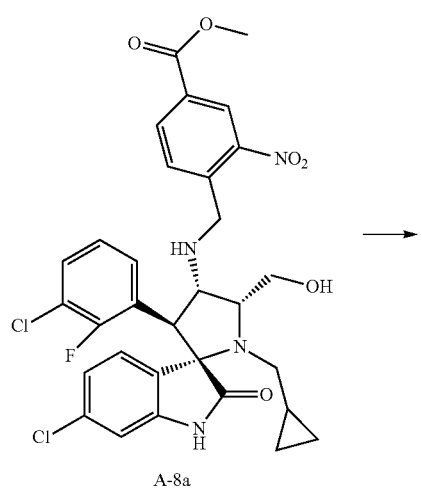
A-8a

168
-continued

I-1

Intermediate A-8a (2.88 g, 4.48 mmol) is dissolved in iPrOH (25 mL) and water (4 mL) and potassium hydroxide (2.35 g, 41.9 mmol) is slowly added. The resulting mixture is stirred for 16 h at rt. The mixture is diluted with EtOAc and treated with a diluted aqueous solution of citric acid. After extraction of the aqueous layer with EtOAc, the organic layers are combined and dried with sodium sulfate. The solvents are removed under reduced pressure to give crude compound I-1 which is purified by chromatography.

The following compounds (I) (table 17) are available in an analogous manner starting from different intermediates A-8.

TABLE 17

| # | structure | $t_{ret}$ [min] | $[M + H]^+$ | HPLC method |
|---|-----------|-----------------|-------------|-------------|
| I-1 | 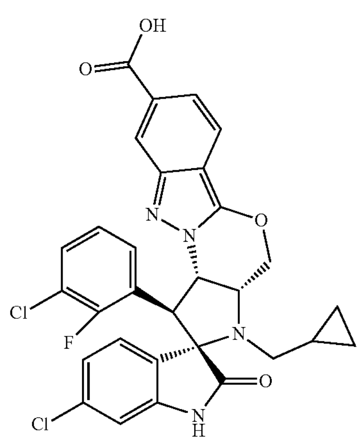 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1cccc(Cl)c1F] | 1.10 | 593 | A |

TABLE 17-continued

| # | structure | $t_{ret}$ [min] | [M + H]⁺ | HPLC method |
|---|---|---|---|---|
| I-2 | Chiral | 1.09 | 593 | A |
| I-3 | Chiral | 1.10 | 593 | A |
| I-4 | 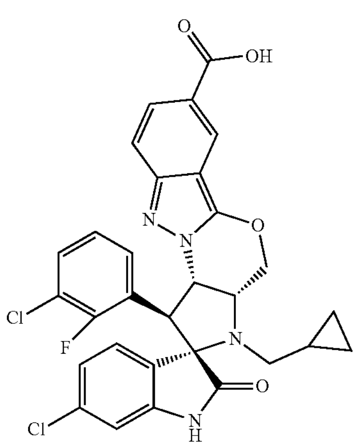 [SMILES: O=C(O)c1ccc2nn3c(c2c1)OC[C@H]1[C@@H]3[C@H](c2cccc(Cl)c2F)[C@]2(C(=O)Nc3cc(Cl)ccc32)N1CC1CC1] | 1.04 | 593 | A |

TABLE 17-continued
| # | structure | $t_{ret}$ [min] | [M + H]$^+$ | HPLC method |
|---|---|---|---|---|
| I-5 | 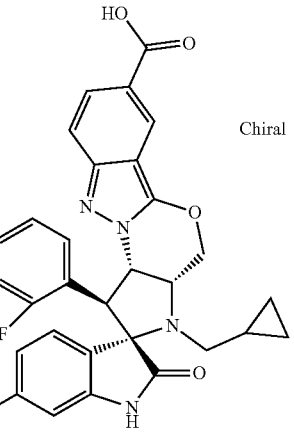 | 1.04 | 593 | A |
| I-6 | 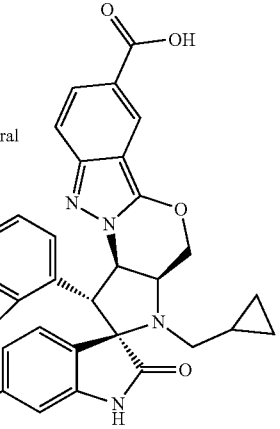 | 1.05 | 593 | A |
| I-7 | 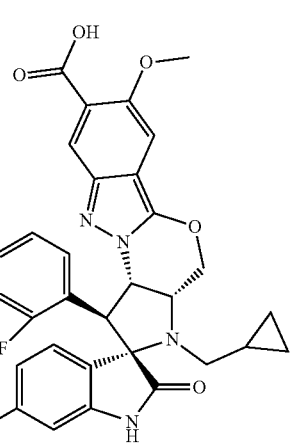 | 1.09 | 623 | A |

TABLE 17-continued
| # | structure | $t_{ret}$ [min] | [M + H]$^+$ | HPLC method |
|---|---|---|---|---|
| I-8 | 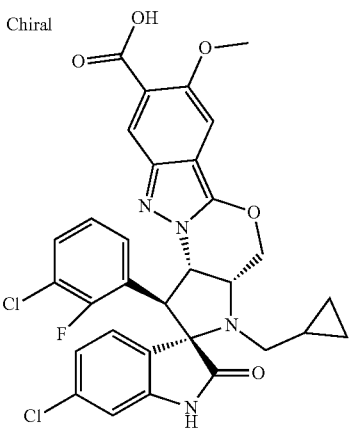 [SMILES: COc1cc2c3n(nc2cc1C(=O)O)[C@@H]1[C@H](CO3)N(CC2CC2)[C@@]2(C(=O)Nc3cc(Cl)ccc32)[C@H]1c1cccc(Cl)c1F] | 1.09 | 623 | A |
| I-9 | 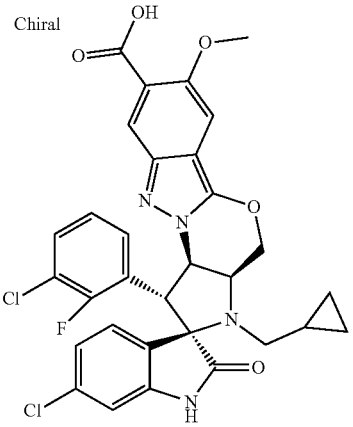 [SMILES: COc1cc2c3n(nc2cc1C(=O)O)[C@H]1[C@@H](CO3)N(CC2CC2)[C@]2(C(=O)Nc3cc(Cl)ccc32)[C@@H]1c1cccc(Cl)c1F] | 1.09 | 623 | A |
| I-10 | 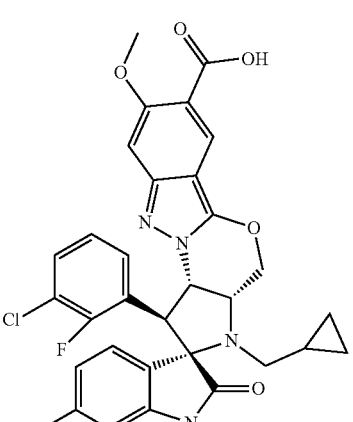 | 1.01 | 623 | A |

TABLE 17-continued

| # | structure | $t_{ret}$ [min] | $[M + H]^+$ | HPLC method |
|---|---|---|---|---|
| I-11 | Chiral | 1.06 | 623 | A |
| I-12 | Chiral | 1.06 | 623 | A |
| I-13 | 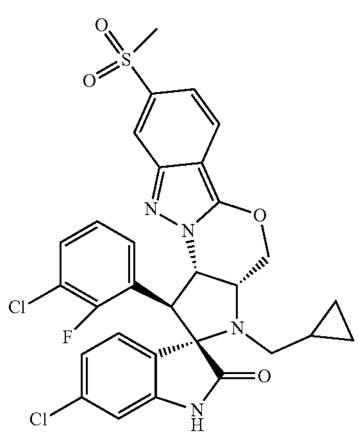 [SMILES: CS(=O)(=O)c1ccc2c3n(nc2c1)[C@@H]1[C@H](CO3)N(CC2CC2)[C@@]2(C(=O)Nc3cc(Cl)ccc32)[C@H]1c1cccc(Cl)c1F] | 1.45 | 627 | A |

TABLE 17-continued
| # | structure | t_ret [min] | [M + H]+ | HPLC method |
|---|---|---|---|---|
| I-14 | 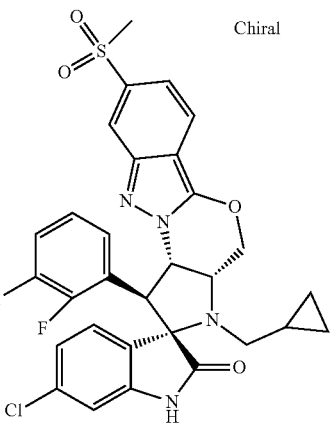 Chiral | 1.45 | 627 | A |
| I-15 | 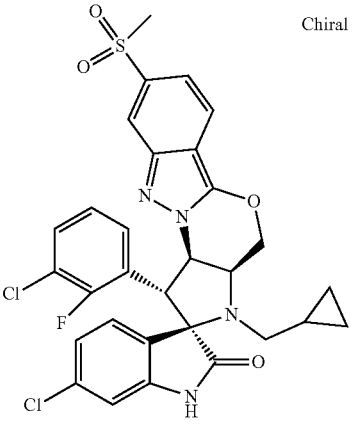 [SMILES: CS(=O)(=O)c1ccc2c3n(nc2c1)[C@H]1[C@@H](CO3)N(CC2CC2)[C@]2(C(=O)Nc3cc(Cl)ccc32)[C@@H]1c1cccc(Cl)c1F] Chiral | 1.45 | 627 | A |
| I-16 | 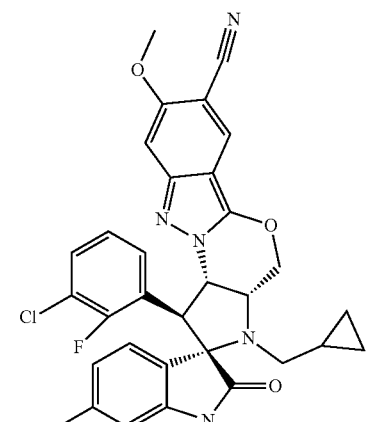 | 1.54 | 604 | A |

TABLE 17-continued

| # | structure | $t_{ret}$ [min] | [M + H]⁺ | HPLC method |
|---|---|---|---|---|
| I-17 | Chiral | 1.54 | 604 | A |
| I-18 | 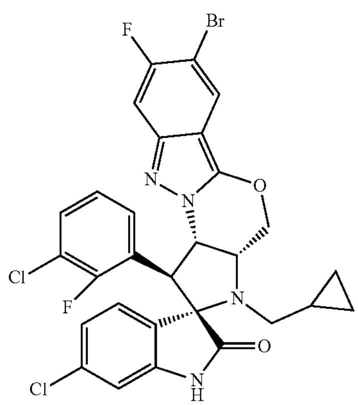 [SMILES: O=C1Nc2cc(Cl)ccc2[C@@]12[C@@H](c1cccc(Cl)c1F)[C@H]1[C@H](COc3c4cc(Br)c(F)cc4nn31)N2CC1CC1] | 1.03 | 647 | E |
| I-19 | Chiral | 1.03 | 647 | E |

TABLE 17-continued

| # | structure | t_ret [min] | [M + H]+ | HPLC method |
|---|---|---|---|---|
| I-20 | 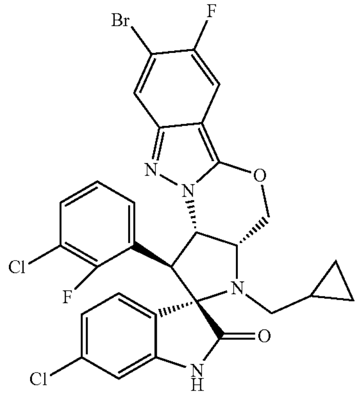 [SMILES: O=C1Nc2cc(Cl)ccc2[C@@]12[C@@H](c1cccc(Cl)c1F)[C@H]1[C@H](COc3c4cc(F)c(Br)cc4nn31)N2CC1CC1] | 1.02 | 647 | E |
| I-21 | 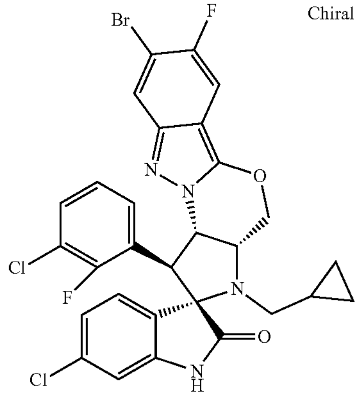 [SMILES: O=C1Nc2cc(Cl)ccc2[C@@]12[C@@H](c1cccc(Cl)c1F)[C@H]1[C@H](COc3c4cc(F)c(Br)cc4nn31)N2CC1CC1] | 1.02 | 647 | E |
| I-22 | 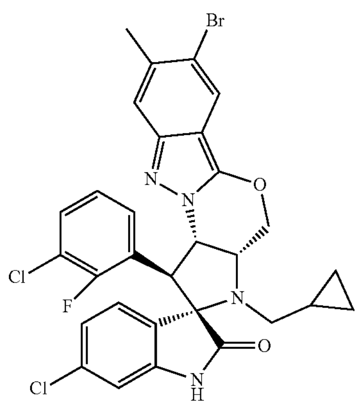 [SMILES: Cc1cc2nn3c(c2cc1Br)OC[C@H]1[C@@H]3[C@H](c2cccc(Cl)c2F)[C@]2(C(=O)Nc3cc(Cl)ccc32)N1CC1CC1] | 643 | 1.73 | A |
| I-23 | 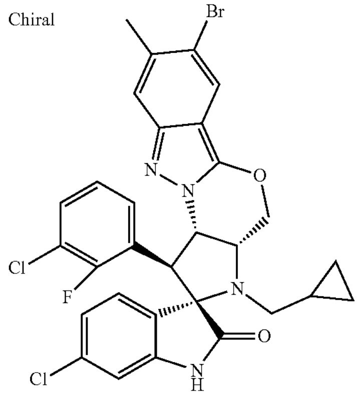 [SMILES: Cc1cc2nn3c(c2cc1Br)OC[C@H]1[C@@H]3[C@H](c2cccc(Cl)c2F)[C@]2(C(=O)Nc3cc(Cl)ccc32)N1CC1CC1] | 643 | 1.73 | A |

TABLE 17-continued

| # | structure | $t_{ret}$ [min] | [M + H]$^+$ | HPLC method |
|---|---|---|---|---|
| I-24 | 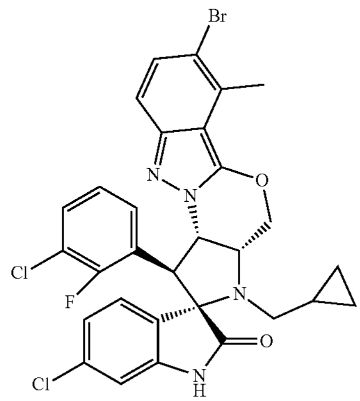 [SMILES: Cc1c(Br)ccc2nn3c(c12)OC[C@H]1[C@@H]3[C@H](c2cccc(Cl)c2F)[C@]2(C(=O)Nc3cc(Cl)ccc32)N1CC1CC1] | 1.27 | 642 | K |
| I-25 | Chiral | 1.27 | 642 | K |
| I-26 | 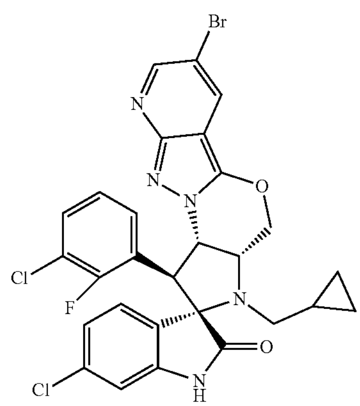 [SMILES: O=C1Nc2cc(Cl)ccc2[C@@]12[C@@H](c1cccc(Cl)c1F)[C@H]1[C@H](COc3c4cc(Br)cnc4nn31)N2CC1CC1] | 628 | 1.53 | A |
| I-27 | Chiral | 628 | 1.53 | A |

TABLE 17-continued
| # | structure | t_ret [min] | [M + H]+ | HPLC method |
|---|---|---|---|---|
| I-28 | 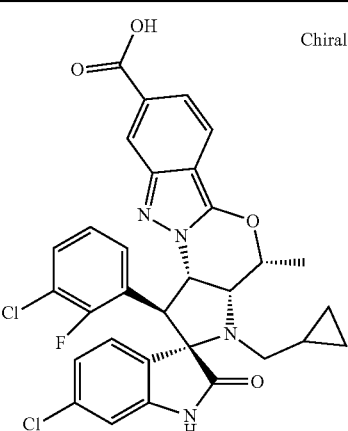 Chiral | 1.10 | 607 | A |
| I-29 | 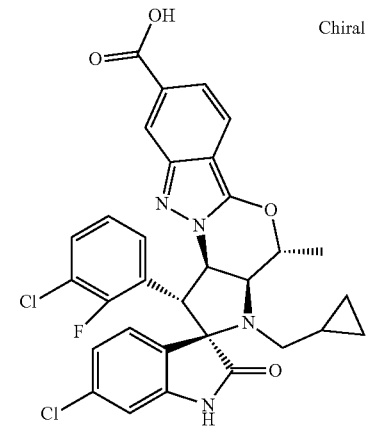 [SMILES: C[C@H]1Oc2c3ccc(C(=O)O)cc3nn2[C@H]2[C@@H]1N(CC1CC1)[C@]1(C(=O)Nc3cc(Cl)ccc31)[C@@H]2c1cccc(Cl)c1F] Chiral | 1.10 | 607 | A |
| I-30 | 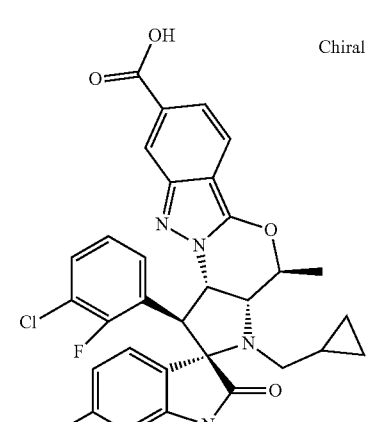 Chiral | 1.09 | 607 | A |

TABLE 17-continued
| # | structure | | $t_{ret}$ [min] | [M + H]$^+$ | HPLC method |
|---|---|---|---|---|---|
| I-31 | 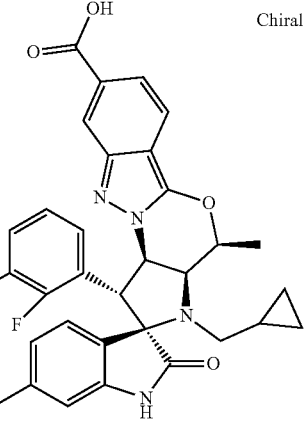 | Chiral | 1.10 | 607 | A |
| I-32 | 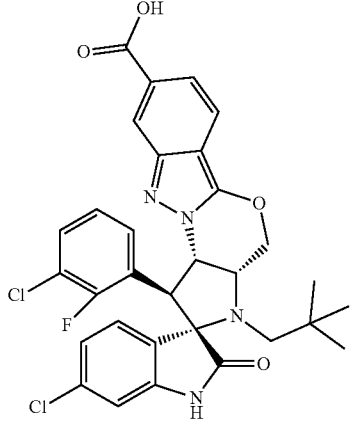 [SMILES: CC(C)(C)CN1[C@H]2COc3c4ccc(C(=O)O)cc4nn3[C@H]2[C@H](c2cccc(Cl)c2F)[C@]12C(=O)Nc1cc(Cl)ccc12] | | 1.16 | 609 | A |
| I-33 | 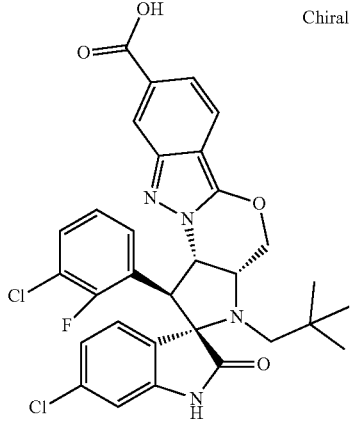 [SMILES: CC(C)(C)CN1[C@H]2COc3c4ccc(C(=O)O)cc4nn3[C@H]2[C@H](c2cccc(Cl)c2F)[C@]12C(=O)Nc1cc(Cl)ccc12] | Chiral | 1.14 | 609 | A |

TABLE 17-continued

| # | structure | $t_{ret}$ [min] | $[M + H]^+$ | HPLC method |
|---|---|---|---|---|
| I-34 | 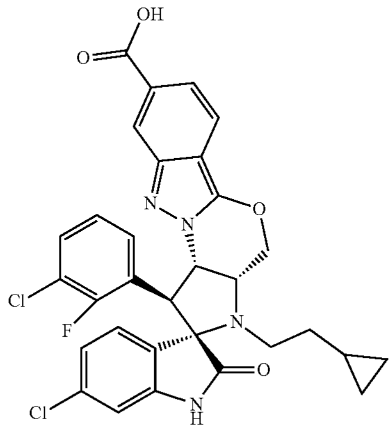 [SMILES: O=C(O)c1ccc2c3n(nc2c1)[C@@H]1[C@H](CO3)N(CCC2CC2)[C@@]2(C(=O)Nc3cc(Cl)ccc32)[C@H]1c1cccc(Cl)c1F] | 1.12 | 607 | A |
| I-35 | Chiral | 1.12 | 607 | A |
| I-36 | 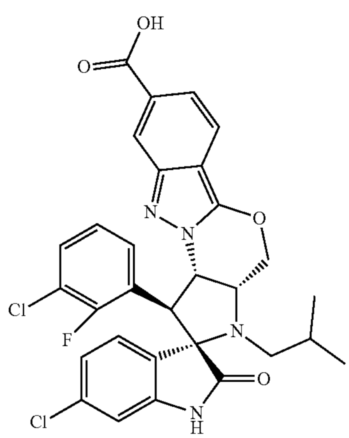 [SMILES: CC(C)CN1[C@H]2COc3c4ccc(C(=O)O)cc4nn3[C@H]2[C@H](c2cccc(Cl)c2F)[C@]12C(=O)Nc1cc(Cl)ccc12] | 1.10 | 595 | A |

TABLE 17-continued
| # | structure | $t_{ret}$ [min] | $[M + H]^+$ | HPLC method |
|---|---|---|---|---|
| I-37 | 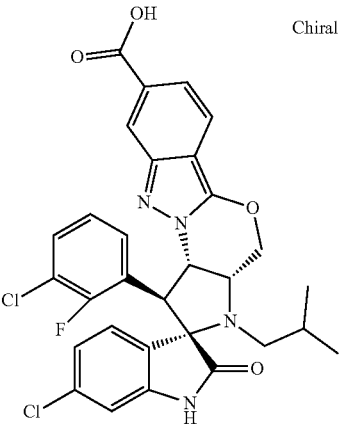 [SMILES: CC(C)CN1[C@H]2COc3c4ccc(C(=O)O)cc4nn3[C@H]2[C@H](c2cccc(Cl)c2F)[C@]12C(=O)Nc1cc(Cl)ccc12] Chiral | 1.10 | 595 | A |
| I-38 | 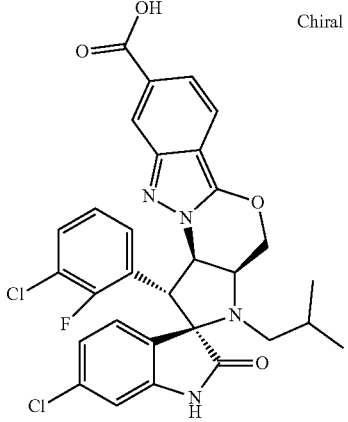 [SMILES: CC(C)CN1[C@@H]2COc3c4ccc(C(=O)O)cc4nn3[C@@H]2[C@@H](c2cccc(Cl)c2F)[C@@]12C(=O)Nc1cc(Cl)ccc12] Chiral | 1.10 | 595 | A |
| I-39 | 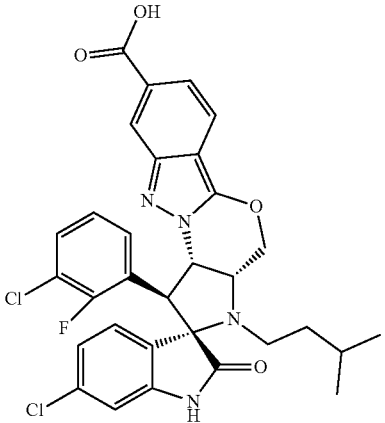 [SMILES: CC(C)CCN1[C@H]2COc3c4ccc(C(=O)O)cc4nn3[C@H]2[C@H](c2cccc(Cl)c2F)[C@]12C(=O)Nc1cc(Cl)ccc12] | 1.14 | 609 | A |

TABLE 17-continued
| # | structure | | $t_{ret}$ [min] | [M + H]$^+$ | HPLC method |
|---|---|---|---|---|---|
| I-40 | 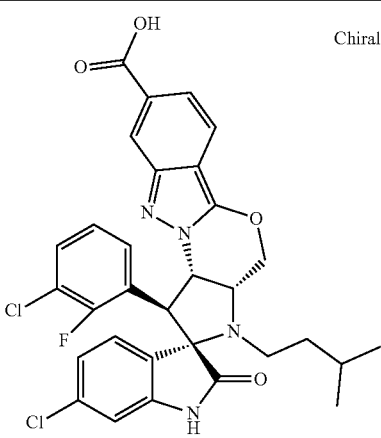 | Chiral | 1.14 | 609 | A |
| I-41 | 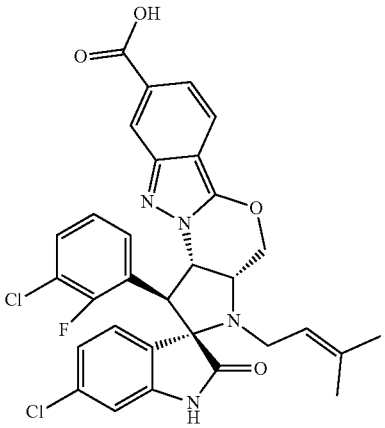 [SMILES: CC(C)=CCN1[C@H]2COc3c4ccc(C(=O)O)cc4nn3[C@H]2[C@H](c2cccc(Cl)c2F)[C@]12C(=O)Nc1cc(Cl)ccc12] | | 1.12 | 607 | A |
| I-42 | 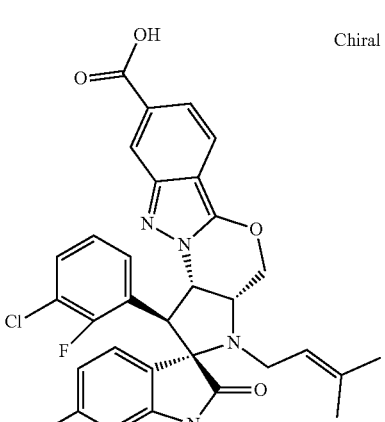 | Chiral | 1.12 | 607 | A |

TABLE 17-continued

| # | structure | $t_{ret}$ [min] | $[M + H]^+$ | HPLC method |
|---|---|---|---|---|
| I-43 | 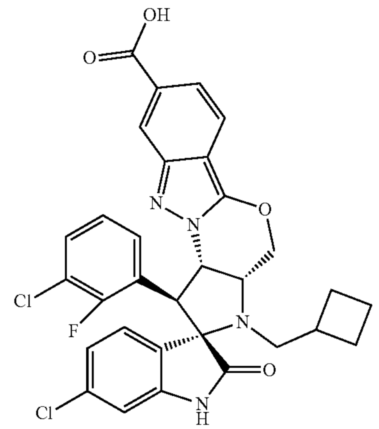 [SMILES: O=C(O)c1ccc2c3n(nc2c1)[C@@H]1[C@H](CO3)N(CC2CCC2)[C@@]2(C(=O)Nc3cc(Cl)ccc32)[C@H]1c1cccc(Cl)c1F] | 1.16 | 607 | A |
| I-44 | Chiral | 1.16 | 607 | A |
| I-45 | 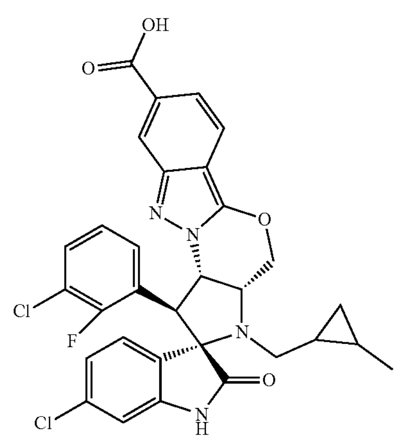 [SMILES: CC1CC1CN1[C@H]2COc3c4ccc(C(=O)O)cc4nn3[C@H]2[C@H](c2cccc(Cl)c2F)[C@]12C(=O)Nc1cc(Cl)ccc12] | 1.15 | 607 | A |

TABLE 17-continued

| # | structure | t_ret [min] | [M + H]+ | HPLC method |
|---|---|---|---|---|
| I-46 | Chiral | 1.15 | 607 | A |
| I-47 | 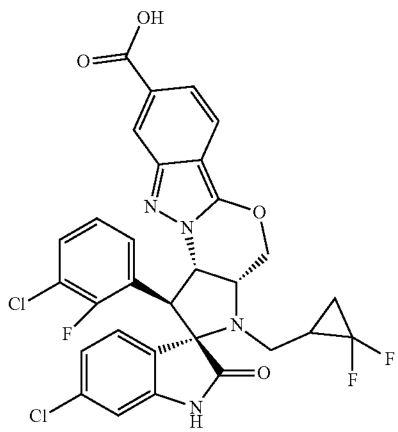 [SMILES: O=C(O)c1ccc2c3n(nc2c1)[C@@H]1[C@H](CO3)N(CC2CC2(F)F)[C@@]2(C(=O)Nc3cc(Cl)ccc32)[C@H]1c1cccc(Cl)c1F] | 1.08 | 629 | A |
| I-48 | Chiral | 1.08 | 629 | A |

TABLE 17-continued

| # | structure | | $t_{ret}$ [min] | $[M + H]^+$ | HPLC method |
|---|---|---|---|---|---|
| I-49 | 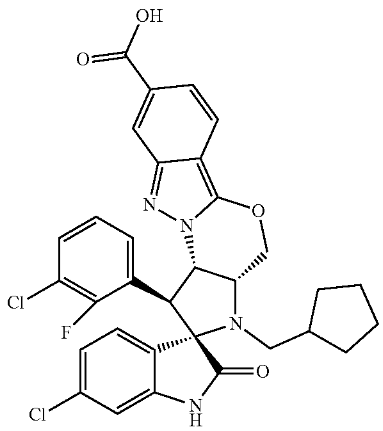 [SMILES: O=C(O)c1ccc2c3n(nc2c1)[C@@H]1[C@H](CO3)N(CC2CCCC2)[C@@]2(C(=O)Nc3cc(Cl)ccc32)[C@H]1c1cccc(Cl)c1F] | | 1.16 | 621 | A |
| I-50 | 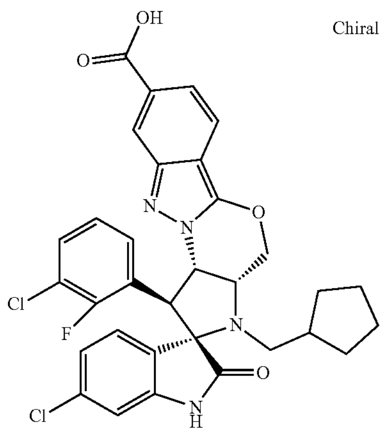 [SMILES: O=C(O)c1ccc2c3n(nc2c1)[C@@H]1[C@H](CO3)N(CC2CCCC2)[C@@]2(C(=O)Nc3cc(Cl)ccc32)[C@H]1c1cccc(Cl)c1F] | Chiral | 1.16 | 621 | A |
| I-51 | 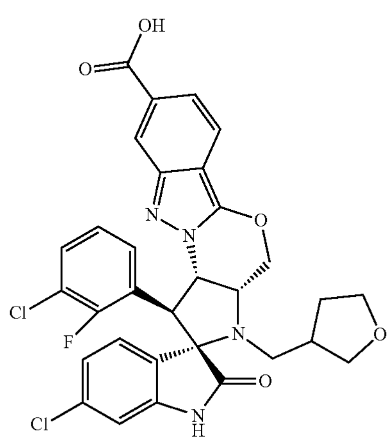 [SMILES: O=C(O)c1ccc2c3n(nc2c1)[C@@H]1[C@H](CO3)N(CC2CCOC2)[C@@]2(C(=O)Nc3cc(Cl)ccc32)[C@H]1c1cccc(Cl)c1F] | | 0.94 | 623 | A |

TABLE 17-continued
| # | structure | $t_{ret}$ [min] | $[M + H]^+$ | HPLC method |
|---|---|---|---|---|
| I-52 | 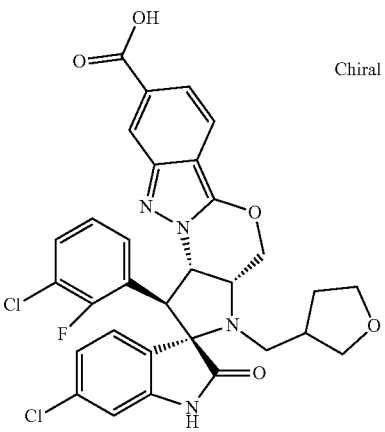 [SMILES: O=C(O)c1ccc2c3n(nc2c1)[C@@H]1[C@H](CO3)N(CC2CCOC2)[C@@]2(C(=O)Nc3cc(Cl)ccc32)[C@H]1c1cccc(Cl)c1F] Chiral | 0.94 | 623 | A |
| I-53 | 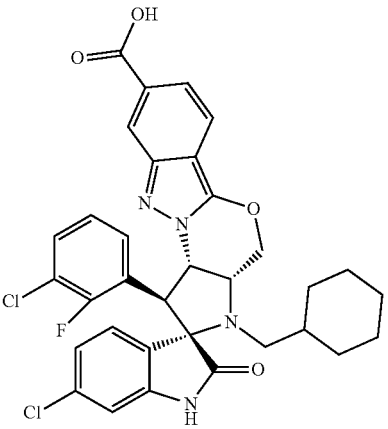 [SMILES: O=C(O)c1ccc2c3n(nc2c1)[C@@H]1[C@H](CO3)N(CC2CCCCC2)[C@@]2(C(=O)Nc3cc(Cl)ccc32)[C@H]1c1cccc(Cl)c1F] | 1.20 | 635 | A |
| I-54 | 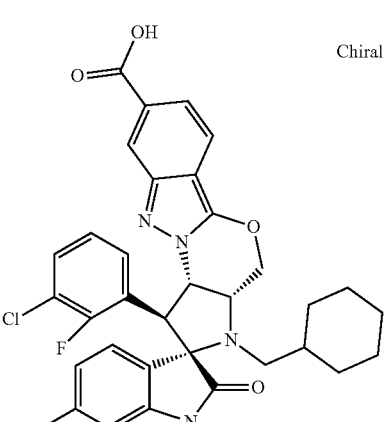 Chiral | 1.20 | 635 | A |

TABLE 17-continued

| # | structure | $t_{ret}$ [min] | $[M + H]^+$ | HPLC method |
|---|---|---|---|---|
| I-55 | 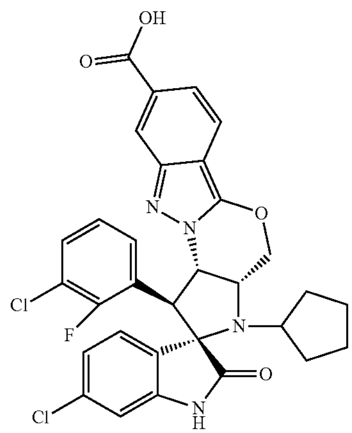 [SMILES: O=C(O)c1ccc2c3n(nc2c1)[C@@H]1[C@H](CO3)N(C2CCCC2)[C@@]2(C(=O)Nc3cc(Cl)ccc32)[C@H]1c1cccc(Cl)c1F] | 1.13 | 607 | A |
| I-56 | Chiral | 1.13 | 607 | A |
| I-57 | 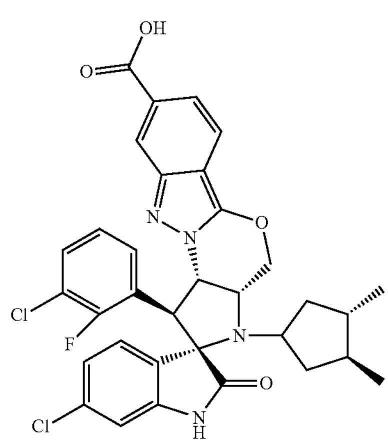 [SMILES: C[C@H]1CC(N2[C@H]3COc4c5ccc(C(=O)O)cc5nn4[C@H]3[C@H](c3cccc(Cl)c3F)[C@]23C(=O)Nc2cc(Cl)ccc23)C[C@@H]1C] | 1.20 | 635 | A |

TABLE 17-continued
| # | structure | $t_{ret}$ [min] | $[M + H]^+$ | HPLC method |
|---|---|---|---|---|
| I-58 | 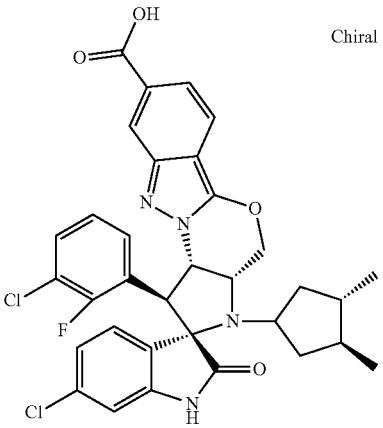 [SMILES: C[C@H]1CC(N2[C@H]3COc4c5ccc(C(=O)O)cc5nn4[C@H]3[C@H](c3cccc(Cl)c3F)[C@]23C(=O)Nc2cc(Cl)ccc23)C[C@@H]1C] Chiral | 1.20 | 635 | A |
| I-59 | 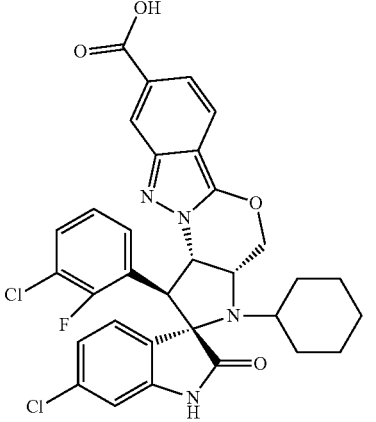 [SMILES: O=C(O)c1ccc2c3n(nc2c1)[C@@H]1[C@H](CO3)N(C2CCCCC2)[C@@]2(C(=O)Nc3cc(Cl)ccc32)[C@H]1c1cccc(Cl)c1F] | 1.16 | 621 | A |
| I-60 | 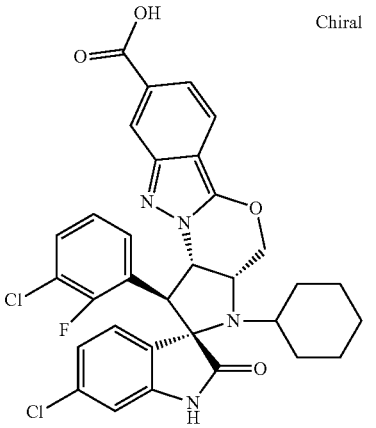 [SMILES: O=C(O)c1ccc2c3n(nc2c1)[C@@H]1[C@H](CO3)N(C2CCCCC2)[C@@]2(C(=O)Nc3cc(Cl)ccc32)[C@H]1c1cccc(Cl)c1F] Chiral | 1.16 | 621 | A |

TABLE 17-continued

| # | structure | t_ret [min] | [M + H]+ | HPLC method |
|---|---|---|---|---|
| I-61 | 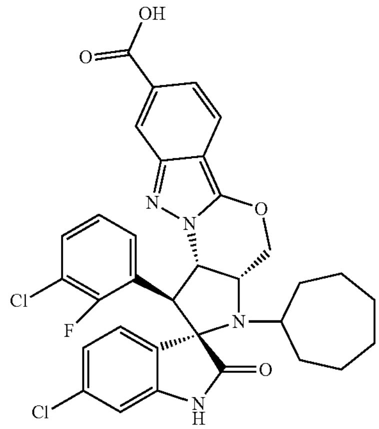 [SMILES: O=C(O)c1ccc2c3n(nc2c1)[C@@H]1[C@H](CO3)N(C2CCCCCC2)[C@@]2(C(=O)Nc3cc(Cl)ccc32)[C@H]1c1cccc(Cl)c1F] | 1.18 | 625 | A |
| I-62 | Chiral | 1.18 | 625 | A |
| I-63 | 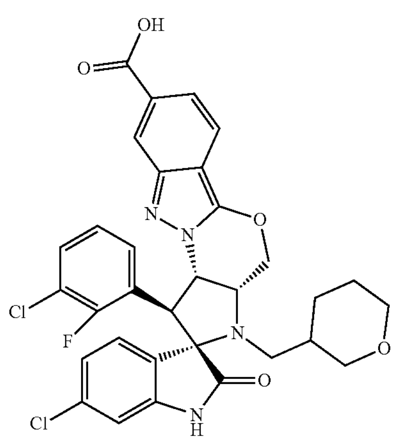 | 1.00 | 637 | A |

TABLE 17-continued
| # | structure | $t_{ret}$ [min] | $[M + H]^+$ | HPLC method |
|---|---|---|---|---|
| I-64 | 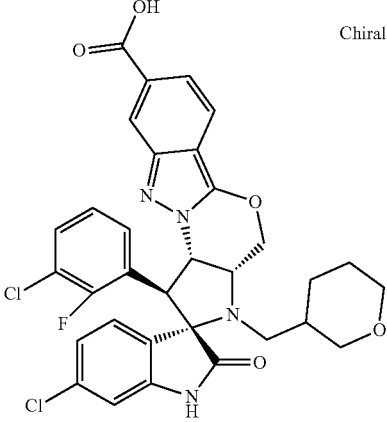 Chiral | 1.00 | 637 | A |
| I-65 | 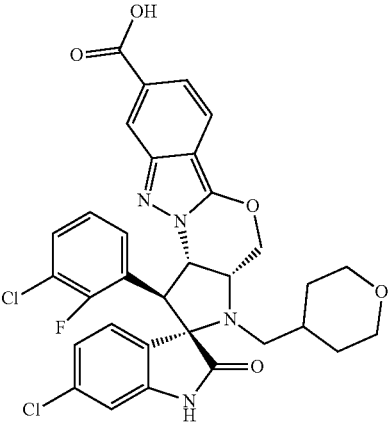 [SMILES: O=C(O)c1ccc2c3n(nc2c1)[C@@H]1[C@H](CO3)N(CC2CCOCC2)[C@@]2(C(=O)Nc3cc(Cl)ccc32)[C@H]1c1cccc(Cl)c1F] | 0.98 | 637 | A |
| I-66 | 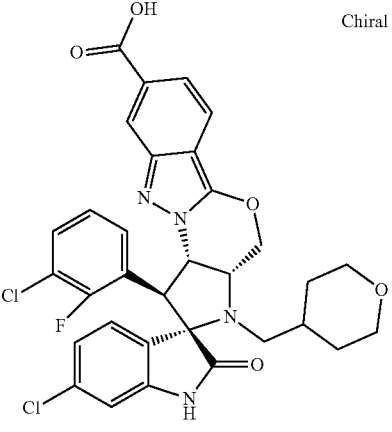 [SMILES: O=C(O)c1ccc2c3n(nc2c1)[C@@H]1[C@H](CO3)N(CC2CCOCC2)[C@@]2(C(=O)Nc3cc(Cl)ccc32)[C@H]1c1cccc(Cl)c1F] Chiral | 0.98 | 637 | A |

TABLE 17-continued

| # | structure | $t_{ret}$ [min] | $[M + H]^+$ | HPLC method |
|---|---|---|---|---|
| I-67 | 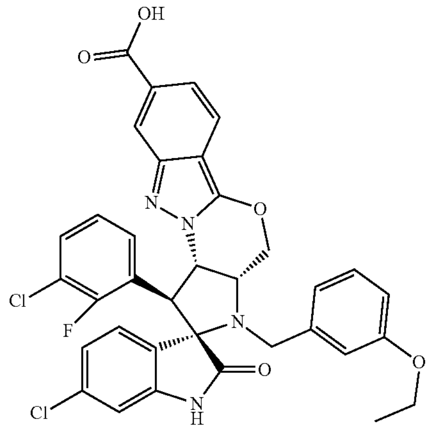 [SMILES: CCOc1cccc(CN2[C@H]3COc4c5ccc(C(=O)O)cc5nn4[C@H]3[C@H](c3cccc(Cl)c3F)[C@]23C(=O)Nc2cc(Cl)ccc23)c1] | 0.98 | 673 | A |
| I-68 | 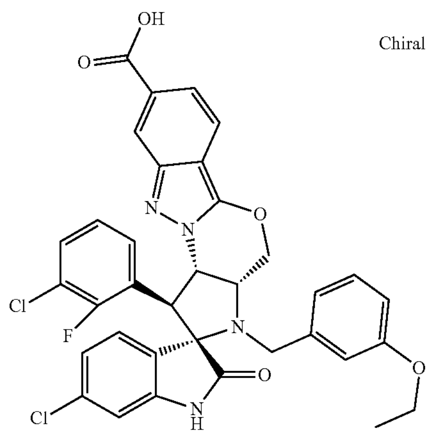 [SMILES: CCOc1cccc(CN2[C@H]3COc4c5ccc(C(=O)O)cc5nn4[C@H]3[C@H](c3cccc(Cl)c3F)[C@]23C(=O)Nc2cc(Cl)ccc23)c1] | 1.00 Chiral | 673 | A |
| I-69 | 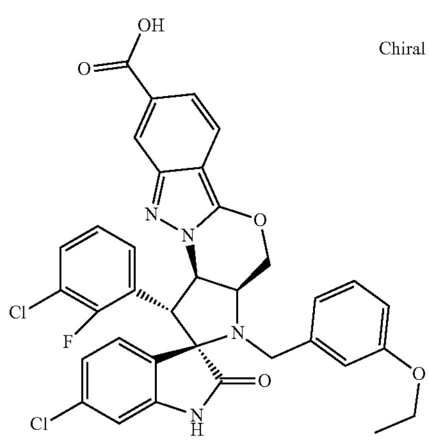 [SMILES: CCOc1cccc(CN2[C@@H]3COc4c5ccc(C(=O)O)cc5nn4[C@@H]3[C@@H](c3cccc(Cl)c3F)[C@@]23C(=O)Nc2cc(Cl)ccc23)c1] | 1.01 Chiral | 673 | A |

TABLE 17-continued

| # | structure | $t_{ret}$ [min] | $[M + H]^+$ | HPLC method |
|---|---|---|---|---|
| I-70 | 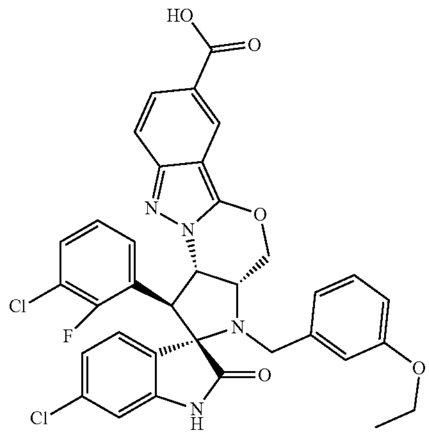 [SMILES: CCOc1cccc(CN2[C@H]3COc4c5cc(C(=O)O)ccc5nn4[C@H]3[C@H](c3cccc(Cl)c3F)[C@]23C(=O)Nc2cc(Cl)ccc23)c1] | 1.05 | 673 | A |
| I-71 Chiral | | 1.05 | 673 | A |
| I-72 | 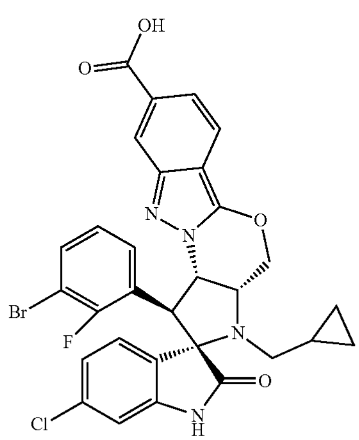 | 1.09 | 637 | A |

TABLE 17-continued
| # | structure | $t_{ret}$ [min] | $[M + H]^+$ | HPLC method |
|---|---|---|---|---|
| I-73 | 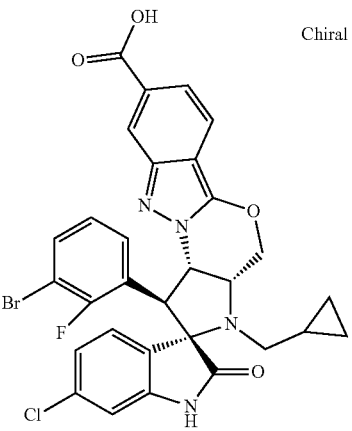 Chiral | 1.09 | 637 | A |
| I-74 | 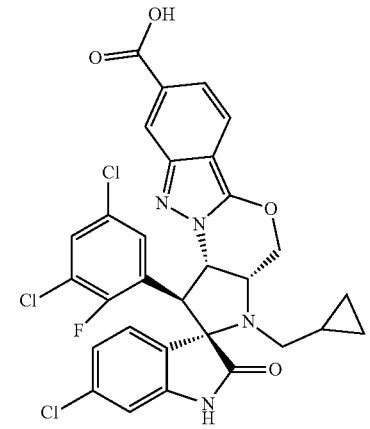 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1cc(Cl)cc(Cl)c1F] | 1.10 | 627 | A |
| I-75 | 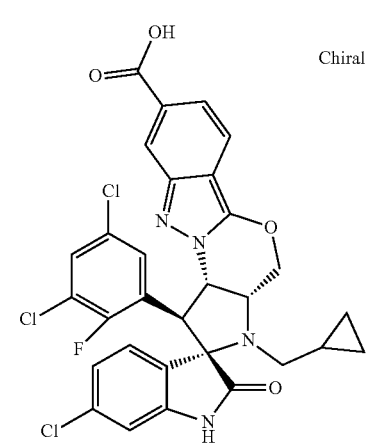 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1cc(Cl)cc(Cl)c1F] Chiral | 1.10 | 627 | A |

TABLE 17-continued

| # | structure | $t_{ret}$ [min] | $[M + H]^+$ | HPLC method |
|---|---|---|---|---|
| I-76 | 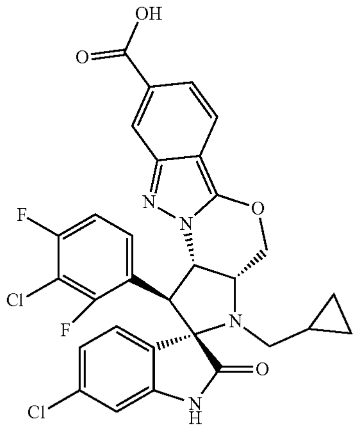 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1ccc(F)c(Cl)c1F] | 1.04 | 611 | A |
| I-77 | Chiral | 1.04 | 611 | A |
| I-78 | 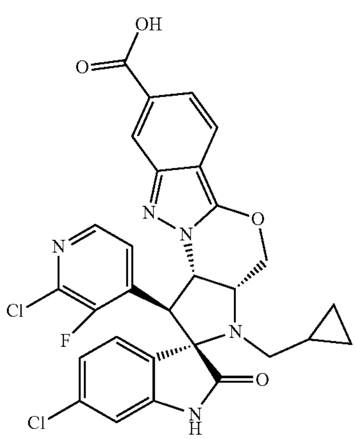 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1ccnc(Cl)c1F] | 1.02 | 594 | A |

TABLE 17-continued
| # | structure | | $t_{ret}$ [min] | $[M + H]^+$ | HPLC method |
|---|---|---|---|---|---|
| I-79 | 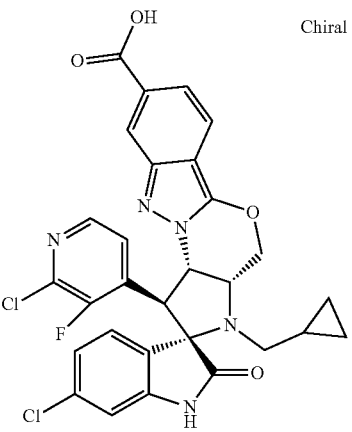 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1ccnc(Cl)c1F] | Chiral | 1.02 | 594 | A |
| I-80 | 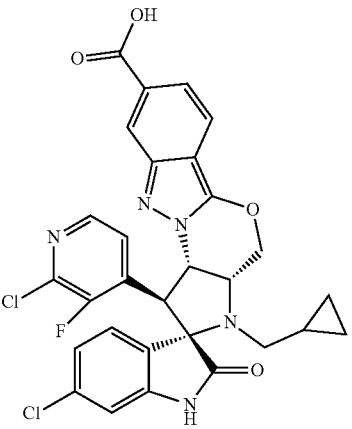 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1ccnc(Cl)c1F] | | 1.04 | 638/640 | A |
| I-81 | Chiral 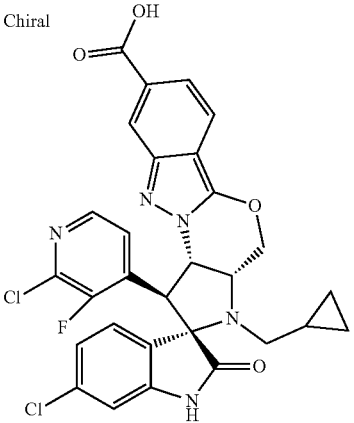 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1ccnc(Cl)c1F] | | 1.04 | 638/640 | A |

TABLE 17-continued

| # | structure | $t_{ret}$ [min] | [M + H]⁺ | HPLC method |
|---|---|---|---|---|
| I-82 | 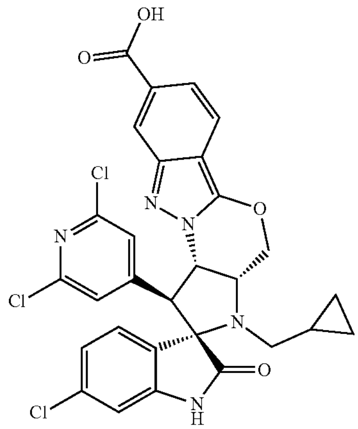 [SMILES: O=C(O)c1ccc2c3n(nc2c1)[C@@H]1[C@H](CO3)N(CC2CC2)[C@@]2(C(=O)Nc3cc(Cl)ccc32)[C@H]1c1cc(Cl)nc(Cl)c1] | 1.06 | 610 | A |
| I-83 | Chiral | 1.06 | 610 | A |
| I-84 | 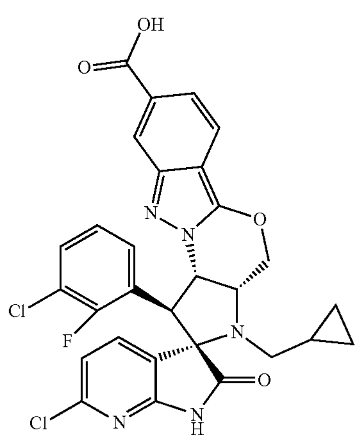 [SMILES: O=C(O)c1ccc2c3n(nc2c1)[C@@H]1[C@H](CO3)N(CC2CC2)[C@@]2(C(=O)Nc3nc(Cl)ccc32)[C@H]1c1cccc(Cl)c1F] | 1.00 | 594 | A |

TABLE 17-continued
| # | structure | $t_{ret}$ [min] | [M + H]⁺ | HPLC method |
|---|---|---|---|---|
| I-85 | 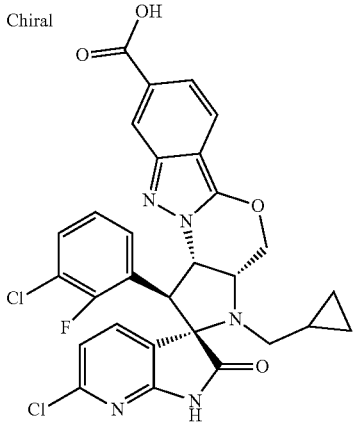 [SMILES: O=C(O)c1ccc2c3n(nc2c1)[C@@H]1[C@H](CO3)N(CC2CC2)[C@@]2(C(=O)Nc3nc(Cl)ccc32)[C@H]1c1cccc(Cl)c1F] | 1.00 | 594 | A |
| I-86 | 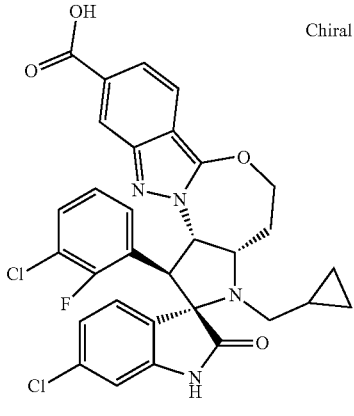 [SMILES: O=C(O)c1ccc2c3n(nc2c1)[C@@H]1[C@H](CCO3)N(CC2CC2)[C@@]2(C(=O)Nc3cc(Cl)ccc32)[C@H]1c1cccc(Cl)c1F] | 1.12 | 607 | A |
| I-87 | 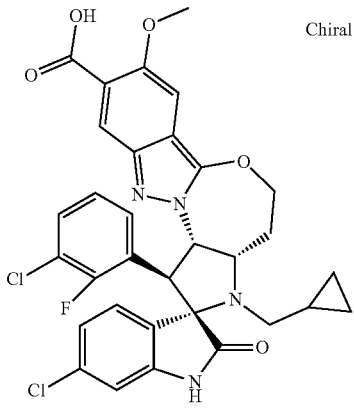 [SMILES: COc1cc2c3n(nc2cc1C(=O)O)[C@@H]1[C@H](CCO3)N(CC2CC2)[C@@]2(C(=O)Nc3cc(Cl)ccc32)[C@H]1c1cccc(Cl)c1F] | 1.10 | 637 | A |

TABLE 17-continued

| # | structure | $t_{ret}$ [min] | $[M + H]^+$ | HPLC method |
|---|---|---|---|---|
| I-88 | 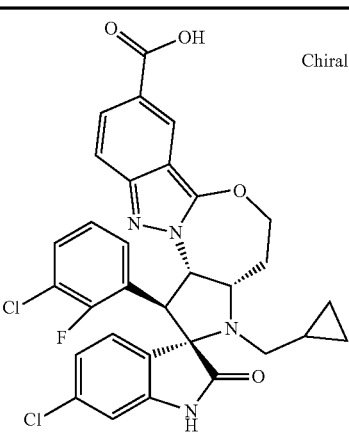 Chiral | 1.03 | 607 | A |
| I-89 | 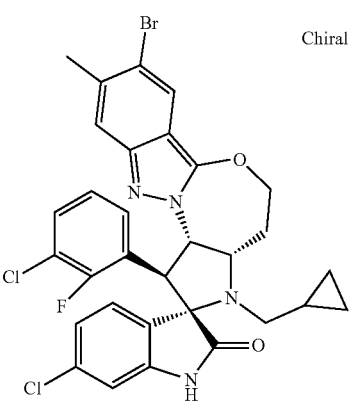 [SMILES: Cc1cc2nn3c(c2cc1Br)OCC[C@H]1[C@@H]3[C@H](c2cccc(Cl)c2F)[C@]2(C(=O)Nc3cc(Cl)ccc32)N1CC1CC1] Chiral | 1.77 | 655 | A |

Synthesis of Further Compounds (I) by Amidation of Initially Obtained Compounds (I)

Experimental Procedure for the Synthesis of Compound I-90

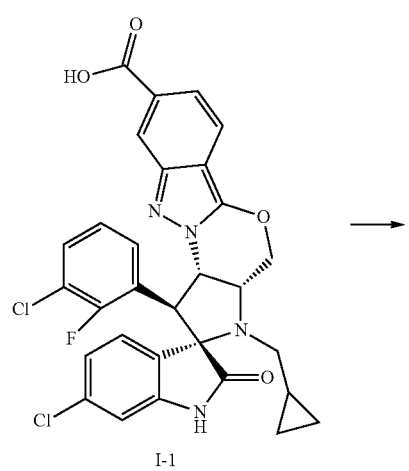

I-1

→

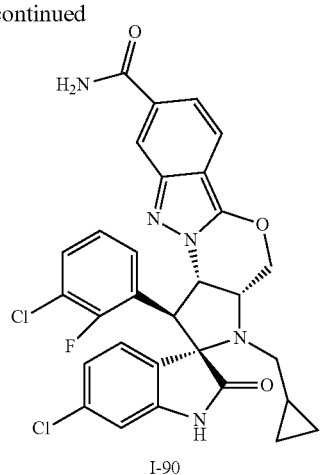

I-90

A solution of compound I-1 (10.0 mg, 0.017 mmol) in DMF (0.5 mL) is cooled to 0° C. and treated with HATU (7.0 mg, 0.019 mmol) and DIPEA (8 µL, 0.051 mmol). After 15 min ammonia (193 µL, 7 N in MeOH, 1.35 mmol) is added and the resulting mixture stirred for 1 h. The mixture is filtrated and the filtrate purified by reversed phase chromatography to yield compound I-90.

The following compounds (I) (table 18) are available in an analogous manner starting from initially obtained compounds (I) and different amines.

TABLE 18

| # | structure | $t_{ret}$ [min] | [M + H]+ | HPLC method |
| --- | --- | --- | --- | --- |
| I-90 | Chiral | 1.28 | 592 | A |
| I-91 | Chiral | 1.54 | 648 | A |

TABLE 18-continued

| # | structure | $t_{ret}$ [min] | $[M + H]^+$ | HPLC method |
|---|---|---|---|---|
| I-92 | 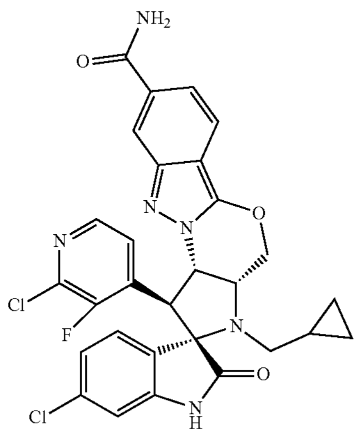 [SMILES: NC(=O)c1ccc2c3n(nc2c1)[C@@H]1[C@H](CO3)N(CC2CC2)[C@@]2(C(=O)Nc3cc(Cl)ccc32)[C@H]1c1ccnc(Cl)c1F] | 1.25 | 593 | A |
| I-93 | Chiral | 1.25 | 593 | A |

Synthesis of Further Compounds (I) by Carboxylation of Initially Obtained Compounds (I)

Experimental Procedure for the Synthesis of Compound I-94

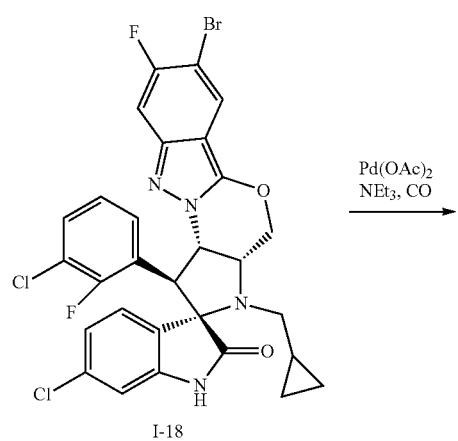

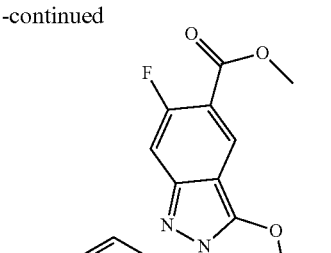

Compound I-18 (45.0 mg, 0.070 mmol) is dissolved in MeOH (40 mL) and treated with 1,1'-bis(diphenylphosphanyl)ferrocene (4.0 mg, 0.007 mmol), palladium diacetate (2.0 mg, 0.009 mmol) and triethylamine (60 μL, 0.427 mmol). The reaction vessel is pressurized with carbonmonoxide (7 bar), the reaction mixture heated to 80° C. and stirred for 16 h. The resulting solution is filtered over Isolute® and the solvent of the filtrate is removed under reduced pressure to provide crude I-94 which is purified by chromatography.

The following compounds (I) (table 19) are available in an analogous manner starting from different compounds (I).

TABLE 19

| # | structure | $t_{ret}$ [min] | [M + H]$^+$ | HPLC method |
|---|---|---|---|---|
| I-94 | 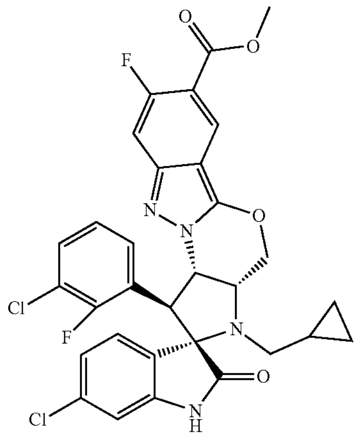 [SMILES: COC(=O)c1cc2c3n(nc2cc1F)[C@@H]1[C@H](CO3)N(CC2CC2)[C@@]2(C(=O)Nc3cc(Cl)ccc32)[C@H]1c1cccc(Cl)c1F] | 0.92 | 625 | E |
| I-95 | Chiral | 0.92 | 625 | E |
| I-96 | 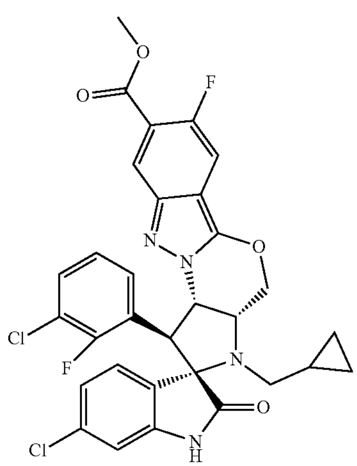 [SMILES: COC(=O)c1cc2nn3c(c2cc1F)OC[C@H]1[C@@H]3[C@H](c2cccc(Cl)c2F)[C@]2(C(=O)Nc3cc(Cl)ccc32)N1CC1CC1] | 0.94 | 625 | E |

TABLE 19-continued
| # | structure | $t_{ret}$ [min] | $[M + H]^+$ | HPLC method |
|---|---|---|---|---|
| I-97 | 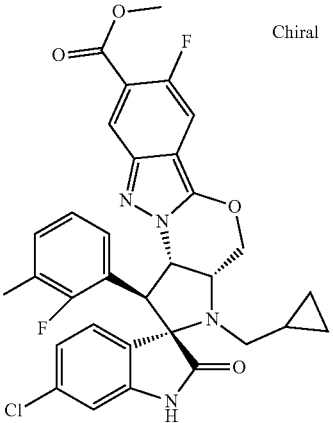 Chiral | 0.94 | 625 | E |
| I-98 | 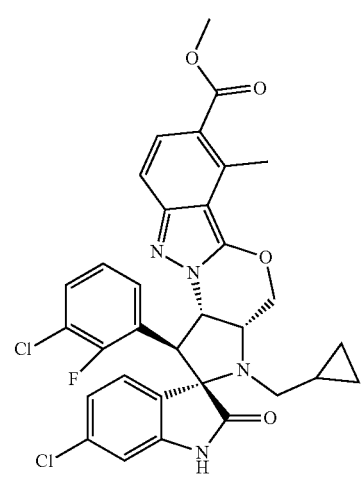 [SMILES: COC(=O)c1ccc2nn3c(c2c1C)OC[C@H]1[C@@H]3[C@H](c2cccc(Cl)c2F)[C@]2(C(=O)Nc3cc(Cl)ccc32)N1CC1CC1] | 0.19 | 621 | J |
| I-99 | Chiral 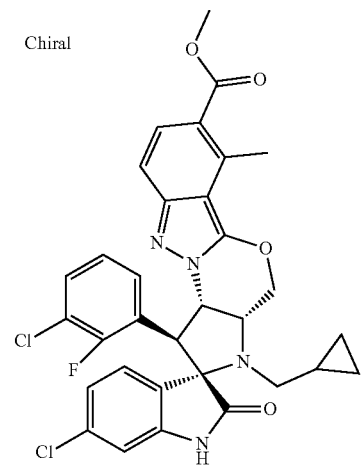 [SMILES: COC(=O)c1ccc2nn3c(c2c1C)OC[C@H]1[C@@H]3[C@H](c2cccc(Cl)c2F)[C@]2(C(=O)Nc3cc(Cl)ccc32)N1CC1CC1] | 0.19 | 621 | J |

TABLE 19-continued

| # | structure | $t_{ret}$ [min] | [M + H]$^+$ | HPLC method |
|---|---|---|---|---|
| I-100 | 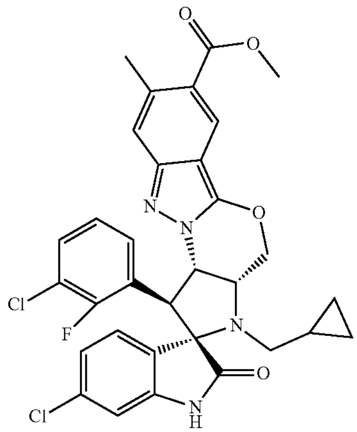 [SMILES: COC(=O)c1cc2c3n(nc2cc1C)[C@@H]1[C@H](CO3)N(CC2CC2)[C@@]2(C(=O)Nc3cc(Cl)ccc32)[C@H]1c1cccc(Cl)c1F] | 1.04 | 621 | A |
| I-101 | 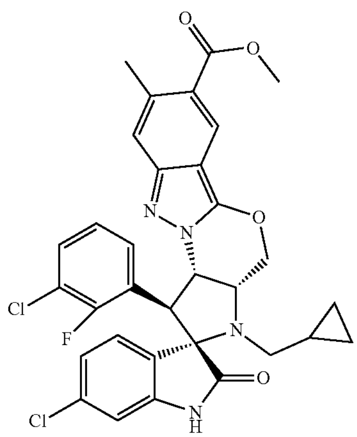 [SMILES: COC(=O)c1cc2c3n(nc2cc1C)[C@@H]1[C@H](CO3)N(CC2CC2)[C@@]2(C(=O)Nc3cc(Cl)ccc32)[C@H]1c1cccc(Cl)c1F] | 1.04 | 621 | A |
| I-102 | 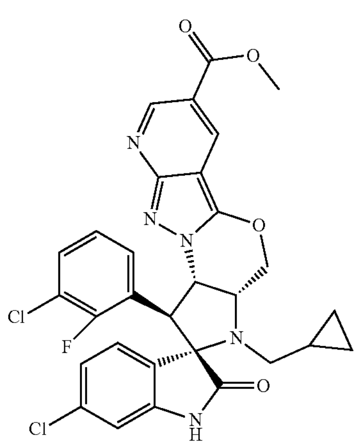 [SMILES: COC(=O)c1cnc2nn3c(c2c1)OC[C@H]1[C@@H]3[C@H](c2cccc(Cl)c2F)[C@]2(C(=O)Nc3cc(Cl)ccc32)N1CC1CC1] | 0.86 | 608 | E |

TABLE 19-continued

| # | structure | $t_{ret}$ [min] | $[M + H]^+$ | HPLC method |
|---|-----------|-----------------|-------------|-------------|
| I-103 | 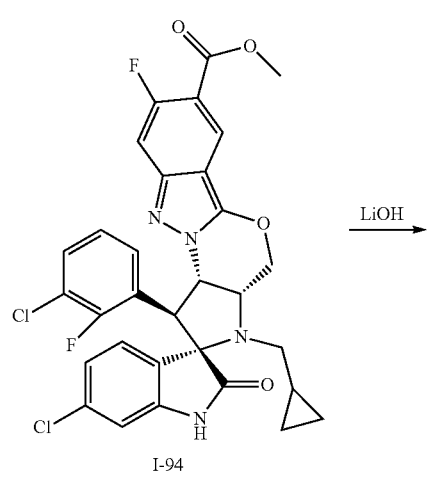 Chiral | 0.86 | 608 | E |
| I-104 | Chiral | 1.61 | 635 | A |

Synthesis of Further Compounds (I) by Saponification of Initially Obtained Compounds (I)

Experimental Procedure for the Synthesis of Compound I-105

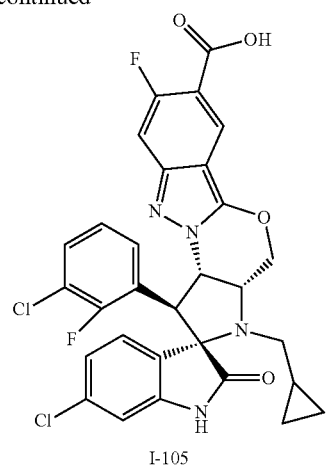

Compound I-94 (40.0 mg, 0.064 mmol) is dissolved in THF (2 mL) and water (1 mL) and treated with lithium hydroxide (10 mg, 0.418 mmol). After stirring for 16 h the resulting solution is acidified with diluted citric acid and the aqueous layer extracted with DCM. The combined organic layers are dried with sodium sulfate and the solvent evaporated. Purification by reversed phase column chromatography furnishes compound I-105.

The following compounds (I) (Table 20) are available in an analogous manner starting from initially obtained compounds (I).

TABLE 20

| # | structure | $t_{ret}$ [min] | [M + H]$^+$ | HPLC method |
|---|---|---|---|---|
| I-105 | 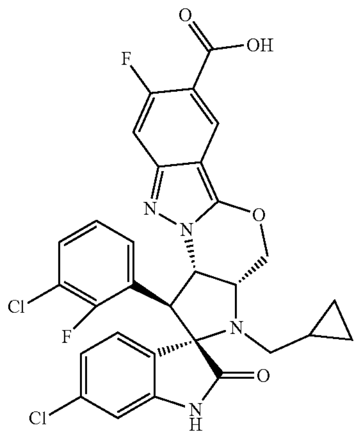 | 1.04 | 611 | A |
| I-106 Chiral | | 1.04 | 611 | A |
| I-107 | 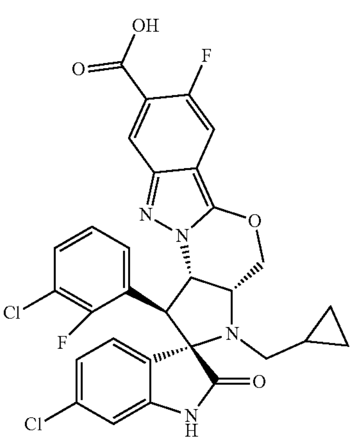 [SMILES: O=C(O)c1cc2nn3c(c2cc1F)OC[C@H]1[C@@H]3[C@H](c2cccc(Cl)c2F)[C@]2(C(=O)Nc3cc(Cl)ccc32)N1CC1CC1] | 1.06 | 611 | A |

TABLE 20-continued
| # | structure | $t_{ret}$ [min] | [M + H]⁺ | HPLC method |
|---|---|---|---|---|
| I-108 | 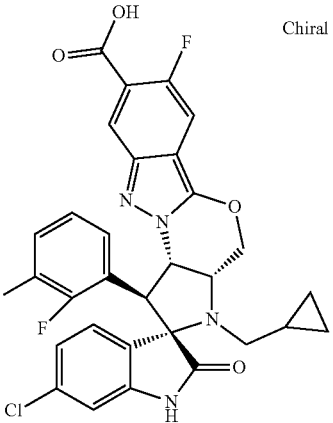 Chiral | 1.06 | 611 | A |
| I-109 | 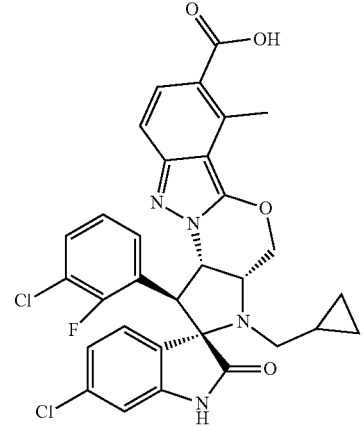 [SMILES: Cc1c(C(=O)O)ccc2nn3c(c12)OC[C@H]1[C@@H]3[C@H](c2cccc(Cl)c2F)[C@]2(C(=O)Nc3cc(Cl)ccc32)N1CC1CC1] | 1.05 | 607 | A |
| I-110 | Chiral 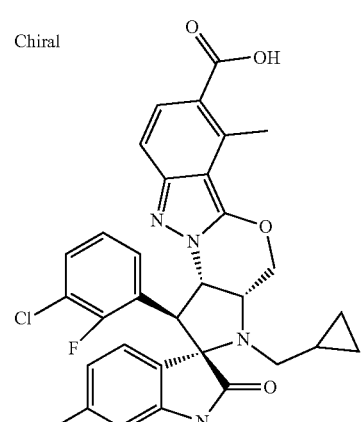 | 1.04 | 607 | A |

TABLE 20-continued

| # | structure | $t_{ret}$ [min] | [M + H]⁺ | HPLC method |
|---|---|---|---|---|
| I-111 | Chiral | 1.03 | 607 | A |
| I-112 | 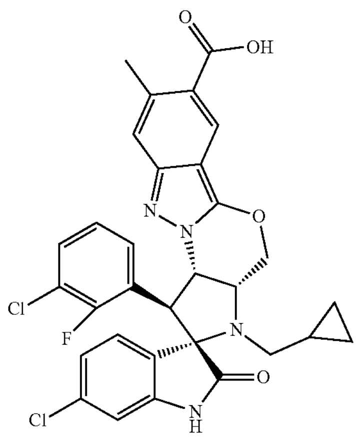 [SMILES: Cc1cc2nn3c(c2cc1C(=O)O)OC[C@H]1[C@@H]3[C@H](c2cccc(Cl)c2F)[C@]2(C(=O)Nc3cc(Cl)ccc32)N1CC1CC1] | 1.02 | 607 | A |
| I-113 | Chiral | 1.02 | 607 | A |

TABLE 20-continued

| # | structure | t_ret [min] | [M + H]+ | HPLC method |
|---|---|---|---|---|
| I-114 | | 1.00 | 594 | A |
| I-115 Chiral | | 1.03 | 594 | A |
| I-116 Chiral | | 1.03 | 594 | A |

TABLE 20-continued

| # | structure | $t_{ret}$ [min] | $[M + H]^+$ | HPLC method |
|---|---|---|---|---|
| I-117 | 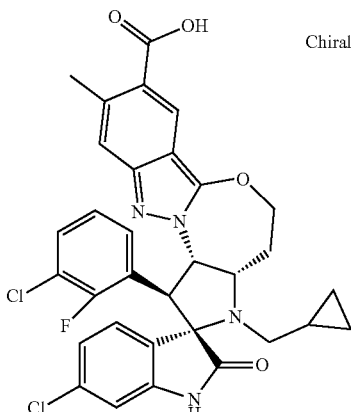 Chiral | 1.02 | 621 | A |

The following Examples describe the biological activity of the compounds according to the invention, without restricting the invention to these Examples.

Compounds of formulae (I), (Ia) and (Ib) are characterised by their many possible applications in the therapeutic field. Particular mention should be made of those applications in which the inhibiting effect on the proliferation of cultivated human tumour cells but also on the proliferation of other cells such as endothelial cells, for example, are involved.

Mdm2-p53 Inhibition AlphaScreen

This assay is used to determine whether the compounds inhibit the p53-MDM2 interaction and thus restore p53 function.

15 µL of compound in 20% DMSO (serial pre-dilutions of compound are done in 100% DMSO) is pipetted to the wells of a white OptiPlate-96 (PerkinElmer). A mix consisting of 20 nM GST-MDM2 protein (aa 23-117) and 20 nM biotinylated p53 wt peptide (encompassing aa 16-27 of wt human p53, amino acid sequence QETFSDLWKLLP-Ttds-Lys-Biotin, molecular weight 2132.56 g/mol) is prepared in assay buffer (50 mM Tris/HCl pH 7.2; 120 mM NaCl; 0.1% bovine serum albumin (BSA); 5 mM dithiothreitol (DTT); 1 mM ethylenediaminetetraacetic acid (EDTA); 0.01% Tween 20). 30 µL of the mix is added to the compound dilutions and incubated for 15 min at rt while gently shaking the plate at 300 rounds per minute (rpm). Subsequently, 15 µL of premixed AlphaLISA Glutathione Acceptor Beads and AlphaScreen Streptavidin Donor Beads from PerkinElmer (in assay buffer at a concentration of 10 µg/mL each) are added and the samples are incubated for 30 min at rt in the dark (shaking 300 rpm). Afterwards, the signal is measured in a PerkinElmer Envision HTS Multilabel Reader using the AlphaScreen protocol from PerkinElmer.

Each plate contains negative controls where biotinylated p53-peptide and GST-MDM2 are left out and replaced by assay buffer. Negative control values are entered as low basis value when using the software GraphPad Prism for calculations. Furthermore, a positive control (5% DMSO instead of test compound; with protein/peptide mix) is pipetted. Determination of $IC_{50}$ values are carried out using GraphPad Prism 3.03 software (or updates thereof).

Table 21 shows the $IC_{50}$ values of example compounds determined using the above assay.

TABLE 21

| # | $IC_{50}$ MDM2 [nM] |
|---|---|
| I-1 | 9 |
| I-2 | 5 |
| I-3 | 557 |
| I-4 | 8 |
| I-5 | 7 |
| I-6 | 619 |
| I-7 | 9 |
| I-8 | 5 |
| I-9 | 818 |
| I-10 | 18 |
| I-11 | 10 |
| I-12 | 986 |
| I-13 | 87 |
| I-14 | 51 |
| I-15 | 261 |
| I-16 | 331 |
| I-28 | 51 |
| I-29 | 520 |
| I-30 | 10 |
| I-31 | 100 |
| I-32 | 19 |
| I-33 | 9 |
| I-34 | 80 |
| I-36 | 16 |
| I-37 | 12 |
| I-38 | 797 |
| I-39 | 48 |
| I-41 | 40 |
| I-43 | 20 |
| I-45 | 97 |
| I-47 | 19 |
| I-49 | 37 |
| I-51 | 41 |
| I-53 | 49 |
| I-55 | 32 |
| I-57 | 76 |
| I-59 | 36 |
| I-61 | 32 |
| I-63 | 15 |
| I-65 | 31 |
| I-67 | 7 |
| I-68 | 3 |
| I-69 | 2144 |
| I-70 | 4 |
| I-72 | 12 |
| I-74 | 13 |
| I-76 | 13 |
| I-78 | 7 |
| I-80 | 6 |
| I-82 | 8 |

TABLE 21-continued

| # | IC$_{50}$ MDM2 [nM] |
|---|---|
| I-84 | 33 |
| I-86 | 35 |
| I-87 | 37 |
| I-88 | 10 |
| I-90 | 26 |
| I-91 | 95 |
| I-92 | 13 |
| I-105 | 13 |
| I-107 | 18 |
| I-109 | 11 |
| I-110 | 7 |
| I-111 | 617 |
| I-112 | 15 |
| I-114 | 9 |
| I-115 | 4 |
| I-116 | 144 |
| I-117 | 6 |

Cell Proliferation Assays
Cell Titer Glo Assay for e.g. SJSA-1, SKOV-3, RS4-11 and KG-1 Cells:

SJSA-1 cells (Osteosarcoma, wildtype p53, ATCC CRL-2098™) are seeded in duplicates at day 1 in flat bottom 96 well microtiter plates (white Packard View Plate 96 well Cat. No. 6005181) in 90 µL RPMI medium, 10% fetal calf serum (FCS, from e.g. JRH Biosciences #12103-500M, Lot.: 3N0207) at a density of 2500 cells/well. Any other luminescence compatible plate format is possible.

Similarly, p53 mutant SKOV-3 cells (ovarian adenocarcinoma, ATCC HTB-77™) are seeded in duplicates in flat bottom 96 well microtiter plates in 90 µL McCoy medium, 10% FCS at a density of 3000 cells/well.

At day 2, 5 µL dilutions of the test compounds covering a concentration range between app. 0.6 and 50000 nM are added to the cells. Cells are incubated for three days in a humidified, CO$_2$-controlled incubator at 37° C.

Wildtype p53 RS4-11 Cells (Acute Lymphoblastic Leukemia, ATCC CRL-1873™):
Day 1: RS4-11 cells are seeded in flat bottom 96 well microtiter plates (white Packard View Plate 96 well Cat. No. 6005181) in 90 µL RPMI medium, 10% fetal calf serum (FCS, from e.g. JRH Biosciences #12103-500M, Lot.: 3N0207) at a density of 5000 cells/well. Any other luminescence compatible plate format is possible.
Day 2: 5 µL dilutions of the test compounds covering a concentration range between app. 0.3 and 25000 nM (alternative dilution schemes are possible) are added to the cells. Cells are incubated for three days in a humidified, CO$_2$ controlled incubator at 37° C. The final DMSO-concentration is 0.5%.

p53 Mutant KG-1 Cells (Acute Myelogenous Leukemia, ATCC CCL-246):
Day 1: KG-1 cells harboring a p53 mutation at the exon 6/intron 6 splice donor site are seeded in flat bottom 96 well microtiter plates (white Packard View Plate 96 well Cat. No. 6005181) in 90 µL IMDM medium, 10% FCS (JRH Biosciences #12103-500M, Lot.: 3N0207) at a density of 10000 cells/well. Any other luminescence compatible plate format is possible.
Day 2: 5 µL dilutions of the test compounds covering a concentration range between app. 0.3 and 25000 nM (alternative dilution schemes are possible) are added to the cells. Cells are incubated for three days in a humidified, CO$_2$ controlled incubator at 37° C. The final DMSO-concentration is 0.5%.

Evaluation of all Cell Titer Glo assays is done at day 5 after seeding. At day 5, 95 µL of Cell Titer Glo reagent (Cell titer Glo Luminescent Cat. No. G7571, Promega) are added to each well and incubated for additional 10 min at rt (with agitation). Luminescence is measured on a Wallac Victor using standard luminescence read out. IC$_{50}$ values are calculated using standard Levenburg Marquard algorithms (GraphPad Prism).

In addition, several other cancer cell lines from diverse tissue origins are sensitive to compounds (I), (Ia) and (Ib). Examples include NCI-H460 (lung), Molp-8 (myeloma) and MV4-11 (AML).

On the basis of their biological properties the compounds of formula (I), (Ia) and (Ib) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers/proliferative diseases may be treated with compounds according to the invention, without being restricted thereto:
brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, glioma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder and other urothelial cancers; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma, hormone receptor positive breast cancer (estrogen receptor positive breast cancer, progesterone receptor positive breast cancer), Her2 positive breast cancer, triple negative breast cancer; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma, multiple myeloma (MM), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, soft tissue sarcoma, liposarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); myelodysplastic syndromes (MDS); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer (e.g. castration-resistant prostate cancer); throat cancer or carcinomas of the pharynx such as for example nasopharynx carcinomas, oropharynx carcinomas and hypopharynx carcinomas; retinoblastoma, vaginal cancer or vaginal carcinoma, mesothelioma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra, cervical cancer, adenoid cystic carcinoma (AdCC), adrenocortical carcinoma and cancer of the vulva.

Preferably, the proliferative diseases/cancers to be treated have by p53 wild-type status.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, antiangiogenic substances, steroids or antibodies.

The compounds of formula (I), (Ia) and (Ib) may be used on their own or in combination with other active substances according to the invention, optionally also in combination with other pharmacologically active substances.

Therapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib, bosutinib and trastuzumab); antimetabolites (e.g. antifolates such as methotrexate, raltitrexed, pyrimidine analogues such as 5-fluorouracil (5-FU), capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors (e.g. sapacitabine), PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitros, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors (e.g. pimasertib), ERK inhibitors, FLT3 inhibitors (e.g. quizartinib), BRD4 inhibitors, IGF-1R inhibitors, TRAILR2 agonists, Bcl-xL inhibitors, Bcl-2 inhibitors (e.g. venetoclax), Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors (e.g. abiraterone, TAK-700), androgen receptor inhibitors (e.g. enzalutamide, ARN-509), immunotherapy (e.g. sipuleucel-T), DNMT inhibitors (e.g. SGI 110, temozolomide, vosaroxin), HDAC inhibitors (e.g. vorinostat, entinostat, pracinostat, panobinostat), ANG1/2 inhibitors (e.g. trebananib), CYP17 inhibitors (e.g. galeterone), radiopharmaceuticals (e.g. radium-223, alpharadin), immunotherapeutic agents (e.g. poxvirus-based vaccine, ipilimumab, immune checkpoint inhibitors) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other possible combination partners are 2-chlorodesoxyadenosine, 2-fluorodesoxy-cytidine, 2-methoxyoestradiol, 2C4, 3-alethine, 131-I-TM-601, 3CPA, 7-ethyl-10-hydroxycamptothecin, 16-aza-epothilone B, ABT-199, ABT-263/navitoclax, ABT-737, A 105972, A 204197, aldesleukin, alisertib/MLN8237, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), AMG-232, AMG-511, AMG 2520765, AMG 2112819, ARRY 162, ARRY 438162, ARRY-300, ARRY-142886/AZD-6244 (selumetinib), ARRY-704/AZD-8330, ATSP-7041, AR-12, AR-42, AS-703988, AXL-1717, AZD-1480, AZD-4547, AZD-8055, AZD-5363, AZD-6244, AZD-7762, ARQ-736, ARQ 680, AS-703026 (primasertib), avastin, AZD-2014, azacitidine (5-aza), azaepothilone B, azonafide, barasertib/AZD1152, BAY-43-9006, BAY 80-6946, BBR-3464, BBR-3576, bevacizumab, BEZ-235/dactolisib, biricodar dicitrate, birinapant, BCX-1777, BKM-120/buparlisib, bleocin, BLP-25, BMS-184476, BMS-247550, BMS-188797, BMS-275291, BMS-663513, BMS-754807, BNP-1350, BNP-7787, BIBW 2992/afatinib, BIBF 1120/nintedanib, BI 836845, BI 2536, BI 6727/volasertib, BI 836845, BI 847325, BI 853520, BIIB-022, bleomycinic acid, bleomycin A, bleomycin B, brivanib, bryostatin-1, bortezomib, brostallicin, busulphan, BYL-719/alpelisib, CA-4 prodrug, CA-4, cabazitaxel, cabozantinib, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CGM-097, CH4987655/RO-4987655, chlorotrianisene, cilengitide, ciclosporin, CD20 antibodies, CDA-II, CDC-394, CKD-602, CKI-27, clofarabine, colchicin, combretastatin A4, COT inhibitors, CHS-828, CH-5132799, CLL-Thera, CMT-3 cryptophycin 52, CPI-613, CTP-37, CTLA-4 monoclonal antibodies (e.g. ipilimumab), CP-461, crizotinib, CV-247, cyanomorpholinodoxorubicin, cytarabine, D 24851, dasatinib, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, DS-3032, E7010, E-6201, edatrexat, edotreotide, efaproxiral, eflornithine, EGFR inhibitors, EKB-569, EKB-509, enzastaurin, elesclomol, elsamitrucin, epothilone B, epratuzumab, EPZ-004777, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fostamatinib, fotemustine, galarubicin, gallium maltolate, ganetespib, gefinitib, gemtuzumab, gemtuzumab ozogamicin, gimatecan, glufosfamide, GCS-IOO, GDC-0623, GDC-0941 (pictrelisib), GDC-0980, GDC-0032, GDC-0068, GDC-0349, GDC-0879, G17DT immunogen, GMK, GMX-1778, GPX-100, gp100-peptide vaccines, GSK-5126766, GSK-690693, GSK-1120212 (trametinib), GSK-1995010, GSK-2118436 (dabrafenib), GSK-2126458, GSK-2132231A, GSK-2334470, GSK-2110183, GSK-2141795, GSK-2636771, GSK-525762A/I-BET-762, GW2016, granisetron, herceptine, hexamethylmelamine, histamine, homoharringtonine, hyaluronic acid, hydroxyurea, hydroxyprogesterone caproate, HDM-201, ibandronate, ibritumomab, ibrutinib/PCI-32765, idasanutlin, idatrexate, idelalisib/CAL-101, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, iproplatin, irofulven, isohomohalichondrin-B, isoflavone, isotretinoin, ixabepilone, JRX-2, JSF-154, JQ-1, J-107088, conjugated oestrogens, kahalid F, ketoconazole, KW-2170, KW-2450, KU-55933, LCL-161, lobaplatin, leflunomide, lenalidomide, lenograstim, leuprolide, leuporelin, lexidronam, LGD-1550, linezolid, lovastatin, lutetium texaphyrin, lometrexol, lonidamine, losoxantrone, LU 223651, lurbinectedin, lurtotecan, LY-S6AKT1, LY-2780301, LY-2109761/galunisertib, mafosfamide, marimastat, masoprocol, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, MLN-0128, MLN-2480, motexafin gadolinium, MS-209, MS-275, MX6, neridronate, neratinib, Nexavar, neovastat, nilotinib, nimesulide, nitroglycerin, nolatrexed, norelin, N-acetylcysteine, NU-7441 06-benzylguanine, oblimersen, omeprazole, olaparib, oncophage, oncoVEX$^{GM-CSF}$, ormiplatin, ortataxel, OX44 antibodies, OSI-027, OSI-906 (linsitinib), 4-1BB antibodies, oxantrazole, oestrogen, onapristone, palbociclib/PD-0332991, panitumumab, panobinostat, patupilone, pazopanib, pegfilgrastim, PCK-3145, pegfilgrastim, PBI-1402, PBI-05204, PD0325901, PD-1 antibodies, PD-616, PEG-paclitaxel, albumin-stabilized paclitaxel, PEP-005, PF-05197281, PF-05212384, PF-04691502, PF-3758309, PHA-665752, PHT-427, P-04, PKC412, P54, PI-88, pelitinib, pemetrexed, pentrix, perifosine, perillylalcohol, pertuzumab, pevonedistat, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, ponatinib, porfiromycin, posaconazole, prednisone, prednisolone, PRT-062607, quinamed, quinupristin, quizartinib/AC220, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7112, RG-7304, RG-7421, RG-7321, RG-7356, RG 7440, RG-7775, rhizoxin, rhu-MAb, rigosertib rinfabate, risedronate, rituximab, robatumumab, rofecoxib, romidepsin, RO-4929097, RO-31-7453, RO-5126766, RO-5068760, RPR 109881A, rubidazone, rubitecan, R-flurbiprofen, RX-0201, ruxolitinib, S-9788, sabarubicin, SAHA, sapacitabine, SAR-405838, sargramostim, satraplatin, SB-408075, SB-431542, Se-015/Ve-015, SU5416, SU6668, SDX-101, selinexor, semustin, seocalcitol, SM-11355, SN-38, SN-4071, SR-27897, SR-31747, SR-13668, SRL-172, sorafenib, spiroplatin, squalamine, STF-31, suberanilohydroxamic acid, sutent, T 900607, T 138067, TAE-684, TAK-733, TAS-103, tacedinaline, talaporfin, tanespimycin, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, tosedostat. trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valproic acid, valrubicin, vandetanib, vatalanib, vincristine, vinflunine, virulizin, vismodegib, vosaroxin, WX-UK1, WX-554, vectibix, XAV-939, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZDI839, ZSTK-474, zoledronat and zosuquidar.

Suitable preparations include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc, agents for delaying release, such as carboxymethyl cellulose, cellulose acetate phthalate, or polyvinyl acetate, carriers, adjuvants, surfactants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I), (Ia) and (Ib) applicable per day is usually from 1 mg to 2000 mg, preferably from 50 to 1000 mg, more preferably from 100 to 500 mg.

The dosage for intravenous use is from 1 mg to 1000 mg per hour, preferably between 5 mg and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:
Examples of Pharmaceutical Formulations

| A) Tablets | per tablet |
|---|---|
| active substance according to formulae (I) or (Ia) or (Ib) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formulae (I) or (Ia) or (Ib) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Tablets | per tablet |
|---|---|
| active substance according to formulae (I) or (Ia) or (Ib) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directely final blend with the magnesium stearate and compressed to tablets of suitable shape and size. When wet-granulated, additional lactose or cellulose and magnesium stearate is added and the mixture is compressed to produce tablets of suitable shape and size.

| D) Ampoule solution | |
|---|---|
| active substance according to formulae (I) or (Ia) or (Ib) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of formula (I)

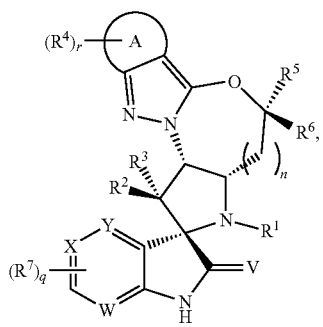

wherein
  $R^1$ is a group, optionally substituted by one or more, identical or different $R^{b1}$ and/or
  $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
    each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$ and —$N(C_{1-4}alkyl)C(O)R^{c1}$;
    each $R^{c1}$ independently of one another denotes hydrogen or a group, optionally substituted by one or more, identical or different $R^{d1}$ and/or $R^{e1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
    each $R^{d1}$ is independently selected from among —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —$NHC(O)R^{e1}$ and —$N(C_{1-4}alkyl)C(O)R^{e1}$;
    each $R^{e1}$ independently of one another denotes hydrogen or a group, optionally substituted by one or more, identical or different $R^{f1}$ and/or $R^{g1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
    each $R^{f1}$ is independently selected from among —$OR^{g1}$, —$NR^{g1}R^{g1}$, halogen, —CN, —$C(O)R^{g1}$, —$C(O)OR^{g1}$, —$C(O)NR^{g1}R^{g1}$, —$S(O)_2R^{g1}$, —$S(O)_2NR^{g1}R^{g1}$, —$NHC(O)R^{g1}$ and —$N(C_{1-4}alkyl)C(O)R^{g1}$;
    each $R^{g1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  $R^2$ and $R^3$, each independently, is selected from among hydrogen, $C_{6-10}$aryl, 5-10 membered heteroaryl and 3-10 membered heterocyclyl, wherein this $C_{6-10}$aryl, 5-10 membered heteroaryl and 3-10 membered heterocyclyl is optionally substituted by one or more, identical or different $R^{b2}$ and/or $R^{c2}$;
    each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;
    each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;
    each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;
    each $R^{e2}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;
  A is selected from among phenyl and 5-6 membered heteroaryl;
  each $R^4$ is independently selected from among $R^{a4}$ and $R^{b4}$;
    each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b4}$ is independently selected from among —$OR^{c4}$, —$NR^{c4}R^{c4}$, halogen, —CN, —$C(O)R^{c4}$, —$C(O)OR^{c4}$, —$C(O)NR^{c4}R^{c4}$, —$C(O)NR^{g4}OR^{c4}$, —$S(O)_2R^{c4}$, —$S(O)_2NR^{c4}R^{c4}$, —$NHSO_2R^{c4}$, —$N(C_{1-4}$alkyl$)SO_2R^{c4}$, —$NHC(O)R^{c4}$ and —$N(C_{1-4}$alkyl$)C(O)R^{c4}$;

each $R^{c4}$ independently of one another denotes hydrogen or a group, optionally substituted by one or more, identical or different $R^{d4}$ and/or $R^{e4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d4}$ is independently selected from among —$OR^{e4}$, —$NR^{e4}R^{e4}$, halogen, —CN, —$C(O)R^{e4}$, —$C(O)OR^{e4}$, —$C(O)NR^{e4}R^{e4}$, —$C(O)NR^{g4}OR^{e4}$, —$S(O)_2R^{e4}$, —$S(O)_2NR^{e4}R^{e4}$, —$NHC(O)R^{e4}$ and —$N(C_{1-4}$alkyl$)C(O)R^{e4}$;

each $R^{e4}$ independently of one another denotes hydrogen or a group, optionally substituted by one or more, identical or different $R^{f4}$ and/or $R^{g4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{f4}$ is independently selected from among —$OR^{g4}$, —$NR^{g4}R^{g4}$, halogen, —CN, —$C(O)R^{g4}$, —$C(O)OR^{g4}$, —$C(O)NR^{g4}R^{g4}$, —$C(O)NR^{g4}OR^{g4}$, —$S(O)_2R^{g4}$, —$S(O)_2NR^{g4}R^{g4}$, —$NHC(O)R^{g4}$ and —$N(C_{1-4}$alkyl$)C(O)R^{g4}$;

each $R^{g4}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

r denotes the number 0, 1, 2 or 3

$R^5$ and $R^6$, each independently, is selected from among hydrogen, $C_{1-4}$alkyl and $C_{1-4}$haloalkyl;

n denotes the number 1;

each $R^7$ is independently selected from among halogen, $C_{1-4}$alkyl, —CN, $C_{1-4}$haloalkyl, —$OC_{1-4}$alkyl and —$OC_{1-4}$haloalkyl;

q denotes the number 0, 1, 2 or 3;

W, X and Y is each independently selected from —N= and —CH= with the proviso that the hydrogen in each —CH= may be replaced by a substituent $R^7$ if present and that a maximum of two of W, X and Y can be —N=;

V is oxygen or sulfur;

or a salt thereof.

2. The compound according to claim 1 of formula (Ia)

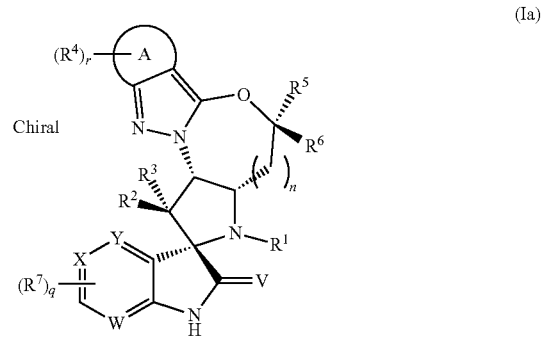

(Ia)

or a salt thereof.

3. The compound according to claim 1, wherein
$R^1$ is a group, optionally substituted by one or more, identical or different $R^{b1}$ and/or $R^{c1}$, selected from among $C_{1-6}$alkyl, $C_{2-6}$alkenyl, $C_{1-6}$haloalkyl and $C_{3-7}$cycloalkyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2 NR^{c1}R^{c1}$, —$NHC(O)R^{c1}$ and —$N(C_{1-4}$alkyl$)C(O)R^{c1}$;

each $R^{c1}$ independently of one another denotes hydrogen or a group, optionally substituted by one or more, identical or different $R^{d1}$ and/or $R^{e1}$, selected from among $C_{1-6}$alkyl, $C_{3-7}$cycloalkyl, $C_{6-10}$aryl, 5-10 membered heteroaryl and 3-10 membered heterocyclyl;

each $R^{d1}$ is independently selected from among —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2 NR^{e1}R^{e1}$, —$NHC(O)R^{e1}$ and —$N(C_{1-4}$alkyl$)C(O)R^{e1}$;

each $R^{e1}$ independently of one another is selected from among hydrogen, $C_{1-6}$alkyl, $C_{3-7}$cycloalkyl, $C_{6-10}$aryl, 5-10 membered heteroaryl and 3-10 membered heterocyclyl;

or a salt thereof.

4. The compound according to claim 1, wherein
one of $R^2$ and $R^3$ is hydrogen and the other is selected from among phenyl and 5-6 membered heteroaryl, wherein this phenyl and 5-6 membered heteroaryl is optionally substituted by one or more, identical or different $R^{b2}$ and/or $R^{c2}$;

each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2 NR^{c2}R^{c2}$, —$NHC(O)R^{c2}$ and —$N(C_{1-4}$alkyl$)C(O)R^{c2}$;

each $R^{c2}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

or a salt thereof.

5. The compound according to claim 4, wherein
one of $R^2$ and $R^3$ is hydrogen and the other is selected from among phenyl and pyridyl, wherein this phenyl and pyridyl is optionally substituted by one or more, identical or different substituents selected from among —$OC_{1-6}$alkyl, halogen, $C_{1-6}$alkyl and $C_{1-6}$haloalkyl;

or a salt thereof.

6. The compound according to claim 1, wherein $R^3$ is hydrogen;

or a salt thereof.

7. The compound according to claim 1, wherein

A is selected from among phenyl and 5-6 membered heteroaryl;

each $R^4$ is independently selected from among $R^{a4}$ and $R^{b4}$;

each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b4}$ is independently selected from among —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}OR^{c4}$, —S(O)$_2R^{c4}$, —S(O)$_2$N$R^{c4}R^{c4}$, —NHSO$_2R^{c4}$, —N($C_{1-4}$alkyl)SO$_2R^{c4}$, —NHC(O)$R^{c4}$ and —N($C_{1-4}$alkyl)C(O)$R^{c4}$;

each $R^{c4}$ independently of one another is selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

r denotes the number 0, 1, 2 or 3;

or a salt thereof.

8. The compound according to claim 7, wherein

A is selected from among phenyl and pyridyl;

each $R^4$ is independently selected from among $R^{a4}$ and $R^{b4}$;

each $R^{a4}$ independently of one another is $C_{1-6}$alkyl optionally substituted by one or more, identical or different $R^{b4}$;

each $R^{b4}$ is independently selected from among —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}OR^{c4}$, —S(O)$_2R^{c4}$, —S(O)$_2$N$R^{c4}R^{c4}$, —NHSO$_2R^{c4}$, —N($C_{1-4}$alkyl)SO$_2R^{c4}$, —NHC(O)$R^{c4}$ and —N($C_{1-4}$alkyl)C(O)$R^{c4}$;

each $R^{c4}$ independently of one another is selected from among hydrogen and $C_{1-6}$alkyl;

r denotes the number 0, 1, 2 or 3;

or a salt thereof.

9. The compound according to claim 1, wherein $R^5$ and $R^6$ is hydrogen;

n denotes the number 1;

or a salt thereof.

10. The compound according to claim 1, wherein each $R^7$ independently is halogen and q is 1 or 2;

or a salt thereof.

11. The compound according to claim 1, wherein

V is oxygen;

or a salt thereof.

12. A compound selected from the group consisting of

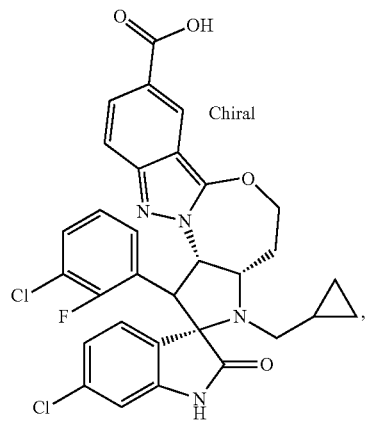

I-88

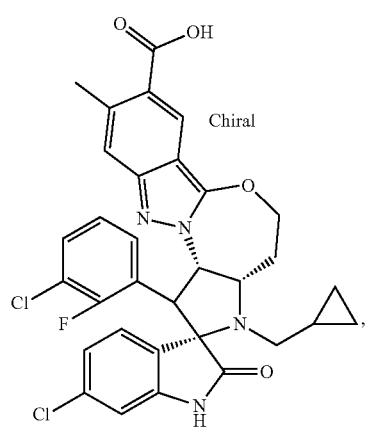

I-117 or a salt thereof.

13. A method for the treatment of acute myeloid leukemia or prostate cancer comprising administering a therapeutically effective amount of a compound according to claim 1, or a pharmaceutically acceptable salt thereof, to a human being.

14. A pharmaceutical composition comprising at least one compound according to claim 1, or a pharmaceutically acceptable salt thereof, and a pharmaceutically acceptable carrier.

15. A pharmaceutical preparation comprising a compound according to claim 1, or a pharmaceutically acceptable salt thereof, and at least one antimitotic agent selected from the group consisting of Vinca alkaloids and taxanes.

16. A method for the chiral separation of compounds (I) according to claim 1 comprising precipitating a salt of one enantiomer formed with a chiral base, from a solution or suspension of compounds (I) in a solvent.

17. The method of claim 16, wherein the chiral base is selected from the group consisting of (R)- and (S)-1,2,3,4-tetrahydronaphthyl-1-amine and the solvent is iso-propyl acetate.

18. The pharmaceutical preparation according to claim 15, wherein the animitotic agent is either a Vinca alkaloid selected from the group consisting of vinblastine, vindesin, vinorelbin and vincristine or a taxane selected from the group consisting of paclitaxel and docetaxel.

* * * * *